(12) United States Patent
Miller

(10) Patent No.: US 10,850,442 B1
(45) Date of Patent: *Dec. 1, 2020

(54) MEDICAL DEVICES AND METHODS FOR PRODUCING THE SAME

(71) Applicant: Additive Device, Inc., Durham, NC (US)

(72) Inventor: Andrew Todd Miller, Morrisville, NC (US)

(73) Assignee: RESTOR3D, INC., Durham, NC (US)

( * ) Notice: Subject to any disclaimer, the term of this patent is extended or adjusted under 35 U.S.C. 154(b) by 62 days.

This patent is subject to a terminal disclaimer.

(21) Appl. No.: 16/209,158

(22) Filed: Dec. 4, 2018

Related U.S. Application Data

(63) Continuation of application No. 15/910,549, filed on Mar. 2, 2018, now Pat. No. 10,183,442.

(51) Int. Cl.
*B29C 64/118* (2017.01)
*A61F 2/02* (2006.01)
(Continued)

(52) U.S. Cl.
CPC .......... *B29C 64/118* (2017.08); *A61F 2/0077* (2013.01); *A61F 2/02* (2013.01); *A61L 31/06* (2013.01); *B29C 64/209* (2017.08); *B29C 64/245* (2017.08); *B29C 64/295* (2017.08); *B29C 64/314* (2017.08);
(Continued)

(58) Field of Classification Search
CPC ... B29C 64/118; B29C 64/314; B29C 64/393; B29C 64/321; B29C 64/295; B29C 64/245; B29C 64/209; A61L 31/06; A61L 31/04; B33Y 50/02; B33Y 70/00; B33Y 30/00; B33Y 40/00; B33Y 10/00; B33Y 80/00; B29L 2031/7532; B29L 2023/186; B29K 2075/00; B29K 2069/00; A61F 2210/0071; A61F 2230/0091; A61F 2230/0019; A61F 2230/0023; A61F 2240/004; A61F 2/02; A61F 2/0077; A61F 2230/0008; A61F 2230/0006; A61F 2210/0076; A61F 2002/0081; A61F 2/82; A61F 2/848;
(Continued)

(56) References Cited

U.S. PATENT DOCUMENTS 4,440,835 A 4/1984 Vignaud
4,588,574 A 5/1986 Felder et al.
(Continued)

OTHER PUBLICATIONS

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).
(Continued)

*Primary Examiner* — Jeffrey M Wollschlager
(74) *Attorney, Agent, or Firm* — Morris, Manning & Martin, LLP; Bryan D. Stewart; Joseph Wallace, Jr.

(57) ABSTRACT

The present disclosure relates generally to medical devices, including airway stents, and additive manufacturing (3D printing) processes for producing the same. Using certain materials and novel printing techniques, the present systems and methods can directly print nearly any size or shape medical device in a few hours. For example, in certain embodiments, the present systems and methods leverage fused deposition modeling ("FDM") and polycarbonate urethane ("PCU") to produce custom medical devices, including airway stents.

30 Claims, 46 Drawing Sheets

(51) Int. Cl.
    *B33Y 30/00*             (2015.01)
    *B33Y 40/00*             (2020.01)
    *B33Y 10/00*             (2015.01)
    *B29C 64/321*           (2017.01)
    *B29C 64/314*           (2017.01)
    *B29C 64/295*           (2017.01)
    *B29C 64/245*           (2017.01)
    *B29C 64/209*           (2017.01)
    *A61L 31/06*            (2006.01)
    *A61F 2/00*              (2006.01)
    *B33Y 80/00*             (2015.01)
    *B33Y 50/02*             (2015.01)
    *B29L 31/00*             (2006.01)
    *B29L 23/18*             (2006.01)
    *B29K 75/00*             (2006.01)
    *B29K 69/00*             (2006.01)
    *B29C 64/393*           (2017.01)
    *B33Y 70/00*             (2020.01)

(52) U.S. Cl.
    CPC ............ *B29C 64/321* (2017.08); *B33Y 10/00* (2014.12); *B33Y 30/00* (2014.12); *B33Y 40/00* (2014.12); *A61F 2002/0081* (2013.01); *A61F 2210/0071* (2013.01); *A61F 2210/0076* (2013.01); *A61F 2230/0006* (2013.01); *A61F 2230/0008* (2013.01); *A61F 2230/0019* (2013.01); *A61F 2230/0023* (2013.01); *A61F 2230/0091* (2013.01); *A61F 2240/004* (2013.01); *B29C 64/393* (2017.08); *B29K 2069/00* (2013.01); *B29K 2075/00* (2013.01); *B29L 2023/186* (2013.01); *B29L 2031/7532* (2013.01); *B33Y 50/02* (2014.12); *B33Y 70/00* (2014.12); *B33Y 80/00* (2014.12)

(58) Field of Classification Search
    CPC . A61F 2/04; A61F 2002/046; A61M 16/0465; A61M 16/0475
    See application file for complete search history.

(56) References Cited

U.S. PATENT DOCUMENTS

| | | |
|---|---|---|
| 5,248,456 A | 9/1993 | Evans, Jr. et al. |
| 7,001,672 B2 | 2/2006 | Justin et al. |
| 7,632,575 B2 | 12/2009 | Justin et al. |
| 7,666,522 B2 | 2/2010 | Justin et al. |
| 8,142,886 B2 | 3/2012 | Noble et al. |
| 8,430,930 B2 | 4/2013 | Hunt |
| 8,457,930 B2 | 6/2013 | Schroeder |
| 8,485,820 B1 | 7/2013 | Ali |
| 8,551,173 B2 | 10/2013 | Lechmann et al. |
| 8,775,133 B2 | 7/2014 | Schroeder |
| 8,828,311 B2 | 9/2014 | Medina et al. |
| 8,843,229 B2 | 9/2014 | Vanasse et al. |
| 8,888,485 B2 | 11/2014 | Ali |
| 9,034,237 B2 | 5/2015 | Sperry et al. |
| 9,180,029 B2 | 11/2015 | Hollister et al. |
| 9,186,257 B2 | 11/2015 | Geisler et al. |
| 9,271,845 B2 | 3/2016 | Hunt et al. |
| 9,295,562 B2 | 3/2016 | Lechmann et al. |
| 9,308,060 B2 | 4/2016 | Ali |
| 9,339,279 B2 | 5/2016 | Dubois et al. |
| 9,364,896 B2 | 6/2016 | Christensen et al. |
| 9,370,426 B2 | 6/2016 | Gabbrielli et al. |
| 9,421,108 B2 | 8/2016 | Hunt |
| 9,433,510 B2 | 9/2016 | Lechmann et al. |
| 9,433,707 B2 | 9/2016 | Swords et al. |
| 9,545,317 B2 | 1/2017 | Hunt |
| 9,549,823 B2 | 1/2017 | Hunt et al. |
| 9,561,115 B2 | 2/2017 | Elahinia et al. |
| 9,572,669 B2 | 2/2017 | Hunt et al. |
| 9,597,197 B2 | 3/2017 | Lechmann et al. |
| 9,636,226 B2 | 5/2017 | Hunt |
| 9,649,178 B2 | 5/2017 | Ali |
| 9,662,157 B2 | 5/2017 | Schneider et al. |
| 9,662,226 B2 | 5/2017 | Wickham |
| 9,668,863 B2 | 6/2017 | Sharp et al. |
| 9,675,465 B2 | 6/2017 | Padovani et al. |
| 9,688,026 B2 | 6/2017 | Ho et al. |
| 9,694,541 B2 | 7/2017 | Pruett et al. |
| 9,715,563 B1 | 7/2017 | Schroeder |
| 9,757,235 B2 | 9/2017 | Hunt et al. |
| 9,757,245 B2 | 9/2017 | O'Neil et al. |
| 9,782,270 B2 | 10/2017 | Wickham |
| 9,788,972 B2 | 10/2017 | Flickinger et al. |
| 9,907,670 B2 | 3/2018 | Deridder et al. |
| 9,910,935 B2 | 3/2018 | Golway et al. |
| 9,918,849 B2 | 3/2018 | Morris et al. |
| 9,943,627 B2 | 4/2018 | Zhou et al. |
| 10,183,442 B1 | 1/2019 | Miller |
| 10,245,152 B2 | 4/2019 | Kloss |
| 10,624,746 B2 | 4/2020 | Jones et al. |
| 2004/0148032 A1 | 7/2004 | Rutter et al. |
| 2007/0118243 A1 | 5/2007 | Schroeder et al. |
| 2008/0206297 A1 | 8/2008 | Roeder et al. |
| 2009/0093668 A1 | 4/2009 | Marten et al. |
| 2010/0137990 A1 | 6/2010 | Apatsidis et al. |
| 2010/0286791 A1 | 11/2010 | Goldsmith |
| 2011/0144752 A1 | 6/2011 | Defelice et al. |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0215310 A1 | 8/2012 | Sharp et al. |
| 2013/0123935 A1 | 5/2013 | Hunt et al. |
| 2013/0158651 A1 | 6/2013 | Hollister et al. |
| 2013/0197657 A1 | 8/2013 | Anca et al. |
| 2013/0218282 A1 | 8/2013 | Hunt |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0288650 A1 | 9/2014 | Hunt |
| 2014/0336680 A1 | 11/2014 | Medina et al. |
| 2014/0371863 A1 | 12/2014 | Vanasse et al. |
| 2015/0105858 A1 | 4/2015 | Papay et al. |
| 2015/0282945 A1 | 10/2015 | Hunt |
| 2015/0282946 A1 | 10/2015 | Hunt |
| 2015/0320461 A1 | 11/2015 | Ehmke |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2016/0051371 A1 | 2/2016 | Defelice et al. |
| 2016/0089138 A1 | 3/2016 | Early et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0256279 A1 | 9/2016 | Sanders et al. |
| 2016/0256610 A1 | 9/2016 | Zhou et al. |
| 2016/0270931 A1 | 9/2016 | Trieu |
| 2016/0287388 A1 | 10/2016 | Hunt et al. |
| 2016/0303793 A1 | 10/2016 | Ermoshkin et al. |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0020685 A1 | 1/2017 | Geisler et al. |
| 2017/0036403 A1 | 2/2017 | Ruff et al. |
| 2017/0042697 A1 | 2/2017 | McShane, III et al. |
| 2017/0056178 A1 | 3/2017 | Sharp et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0156880 A1 | 6/2017 | Halverson et al. |
| 2017/0165085 A1 | 6/2017 | Lechmann et al. |
| 2017/0165790 A1 | 6/2017 | McCarthy et al. |
| 2017/0172758 A1 | 6/2017 | Field et al. |
| 2017/0182222 A1 | 6/2017 | Paddock et al. |

(56) References Cited

U.S. PATENT DOCUMENTS

| | | |
|---|---|---|
| 2017/0209274 A1 | 7/2017 | Beerens et al. |
| 2017/0216035 A1 | 8/2017 | Hunt |
| 2017/0216036 A1 | 8/2017 | Cordaro |
| 2017/0239054 A1 | 8/2017 | Engstrand et al. |
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | Defelice et al. |
| 2017/0296244 A1 | 10/2017 | Schneider et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0022017 A1 | 1/2018 | Fukumoto et al. |
| 2018/0064540 A1 | 3/2018 | Hunt |
| 2018/0085230 A1 | 3/2018 | Hunt |
| 2018/0104063 A1 | 4/2018 | Asaad |
| 2018/0110593 A1 | 4/2018 | Khalil |
| 2018/0110626 A1 | 4/2018 | McShane, III et al. |
| 2018/0110627 A1 | 4/2018 | Sack |
| 2018/0117219 A1 | 5/2018 | Yang et al. |
| 2018/0147319 A1 | 5/2018 | Colucci-Mizenko et al. |
| 2018/0289515 A1 | 10/2018 | Nemes et al. |
| 2019/0262101 A1 | 8/2019 | Shanjani et al. |
| 2019/0343652 A1 | 11/2019 | Petersheim et al. |
| 2020/0030102 A1 | 1/2020 | Mullens et al. |
| 2020/0046512 A1 | 2/2020 | Newman et al. |

OTHER PUBLICATIONS

Rozema et al., The effects of different steam-sterilization programs on material properties of poly(l-lactide), Journal of Applied Biomaterials, vol. 2, 23-28 (1991) (Year: 1991).

Alt, Sami. "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 30 Printed Polycarbonate Urethane in Solution, 108 Polymer 121 (2017).

Andrew T. Miller et al., Deformation and Fatigue of Tough 30 Printed Elastomer Scaffolds Processed by Fused 3 Deposition Modeling and Continuous Liquid Interface Production, 75 J. Mechanical Behavior Biomedical Materials 1 (2017).

MEDICAL DEVICES AND METHODS FOR PRODUCING THE SAME

CROSS REFERENCE TO RELATED APPLICATIONS

This application is a continuation of U.S. patent application Ser. No. 15/910,549, filed on Mar. 2, 2018, and entitled "MEDICAL DEVICES AND METHODS FOR PRODUCING THE SAME;" and is incorporated herein by reference in its entirety.

This application also incorporates by reference the following U.S. patent applications:

U.S. Design patent application No. 29/638,990, entitled "Accordion Airway Stent", filed on Mar. 2, 2018;

U.S. Design patent application No. 29/638,992, entitled "Cutout Airway Stent", filed on Mar. 2, 2018;

U.S. Design patent application No. 29/638,995, entitled "Spiral Airway Stent", filed on Mar. 2, 2018;

U.S. Design patent application No. 29/638,998, entitled "Studded Airway Stent", filed on Mar. 2, 2018; and U.S. Design patent application No. 29/639,000, entitled "Tapered Airway Stent", filed on Mar. 2, 2018;

the disclosures of each of the above applications are incorporated by reference as if the same were fully set forth herein.

TECHNICAL FIELD

The present disclosure relates generally to medical devices, including airway stents, and additive manufacturing (3D printing) processes for producing the same.

BACKGROUND

Stents (and other medical devices) typically come in stock sizes and shapes, which may not necessarily be a good fit for every patient. Stock medical devices may not fit a patient well and, in the case of airway stents, can migrate, irritate a patient's airway, and block the flow of mucus out of their lungs. Each of these potential issues can be problematic.

Patient specific/custom fit silicone stents can be ordered by a surgeon, which may alleviate some of the issues with stock size stents. However, producing customized silicon stents can be laborious, time-intensive, and expensive. To create silicone stents, first a mold of the custom stent is created. Then, the mold is injected with liquid silicone resin. Finally, the liquid silicone resin is allowed to cure and is removed from the mold. This process may take as long as three weeks. As will be understood, this process is economically efficient for stock silicone stents, because only one mold needs to be created for each size and the molds are reusable. However, for patient specific/custom fit silicone stents, three weeks is too long of a wait time and often the molds are too expensive to justify use for a single procedure. Unfortunately, silicone cannot be 3D printed through any conventional 3D printing processes due to its inherent material properties.

As such, there is a long-felt, but unsolved need for a system and/or method of creating customizable medical devices, such as airway stents.

BRIEF SUMMARY OF THE DISCLOSURE

The present disclosure relates generally to medical devices, including airway stents, and additive manufacturing (3D printing) processes for producing the same. Using certain materials and novel printing techniques, the present systems and methods can directly print nearly any size or shape medical device in a few hours.

In certain embodiments, the present systems and methods leverage fused deposition modeling ("FDM") and polycarbonate urethane ("PCU") to produce custom medical devices, including airway stents. FDM has traditionally been overlooked for medical device (and other complex devices/parts) applications because this process is somewhat limited on the complexity of shapes it can print. However, high-quality devices and parts can be printed by FDM techniques by leveraging the novel methods described herein.

According to various embodiments, the present systems and methods relate to a method for producing a seamless polycarbonate urethane airway stent including the steps of: A) heating a nozzle operatively connected to a print bed to approximately 225 degrees Celsius, the nozzle capable of moving along an x-axis, y-axis, and z-axis and including a diameter of approximately 0.5 millimeters; B) heating the print bed to approximately 65 degrees Celsius; C) drying polycarbonate urethane (PCU) filament via a vacuum oven at a temperature of at least 99 degrees Celsius for a minimum of 30 minutes, thereby substantially drying the PCU filament; D) feeding the substantially dry PCU filament through the nozzle, wherein the nozzle melts the substantially dry PCU filament; E) creating a first layer of a seamless medical device by: 1) starting the nozzle at a first point on a first x-y plane and extruding melted PCU filament along a first path at a first speed, creating an outer perimeter of the first layer; 2) extruding melted PCU filament along a second path, creating an inner perimeter of the first layer; and 3) extruding melted PCU in a first rectilinear infill pattern along the first x-y plane between the inner and outer perimeters of the first layer, wherein the distance between an exterior of the outer perimeter and an interior of the inner perimeter is about 0.75 mm to 0.85 mm; F) moving the nozzle along the z-axis; and G) creating a second layer of the medical device by: 1) starting the nozzle at a second point on a second x-y plane and extruding melted PCU filament along a third path at a second speed approximately double the first speed, creating an outer perimeter of the second layer; 2) extruding melted PCU filament along a fourth path creating an inner perimeter of the second layer; and 3) extruding melted PCU in a second rectilinear infill pattern along the second x-y plane between the inner and outer perimeters of the second layer, wherein the first point and the second point are different points, thereby creating a seamless PCU airway stent.

In at least one embodiment, the systems and methods herein relate to a method for producing a seamless polycarbonate urethane stent including the steps of: A) heating a nozzle to a predetermined temperature, the nozzle capable of moving along an x-y plane and z-axis; B) feeding a polycarbonate urethane (PCU) filament through the nozzle, wherein the nozzle melts the PCU filament; C) creating a first layer of a seamless medical device by: 1) starting the nozzle at a first point on the x-y plane and extruding melted PCU filament along a first path, creating an outer perimeter of the first layer; 2) extruding melted PCU in a first rectilinear pattern along the x-y plane to fill in the first layer; D) moving the nozzle along the z-axis; and E) creating a second layer of the medical device by: 1) starting the nozzle at a second point on the x-y plane and extruding melted PCU filament along a second path, creating an outer perimeter of the second layer; and 2) extruding melted PCU in a second rectilinear pattern along the x-y plane to fill in the second layer, wherein the first point and the second point on the x-y plane are different points, thereby creating a seamless medical device.

In various embodiments the systems and methods herein relate to a method for producing a polycarbonate urethane stent including the steps of: A) heating a nozzle operatively connected to a bed to approximately 225 degrees Celsius, the nozzle capable of moving along a x-axis, a y-axis, and a z-axis and including a diameter of approximately 0.5 millimeters; B) drying polycarbonate urethane (PCU) filament via a vacuum oven at a temperature of at least 99 degrees Celsius for a minimum of 30 minutes, thereby substantially drying the PCU filament; C) heating the bed to approximately 65 degrees Celsius; D) feeding the substantially dry PCU filament through the nozzle, wherein the nozzle melts the substantially dry PCU filament; and E) extruding melted PCU filament in discrete vertical layers, wherein each discrete vertical layer is created by: a) extruding melted PCU filament along an outer perimeter of the medical device in an x-y plane, and b) extruding melted PCU in a rectilinear infill pattern along the x-y plane to fill-in the discrete vertical layer of the medical device from the outer perimeter to an inner perimeter, thereby creating a PCU airway stent including an exterior width of between 0.75 mm and 0.85 mm thick with a radial stiffness of between 8 to 20 N/mm tested at about 37 degrees Celsius.

In one or more embodiments, the systems and methods herein relate to an airway stent, including: A) a custom tubular-shaped body including a plurality of 3D-printed polycarbonate urethane layers that form: 1) an exterior surface between 0.75 mm and 0.85 mm thick with a radial stiffness of between 8 to 20 N/mm tested at about 37 degrees Celsius, the exterior surface shaped to fit compatibly against the interior surface of a particular airway; and 2) a plurality of frustum-shaped protrusions that are shaped and located to hold the exterior surface compatibly against the interior surface of the particular airway and that include a sloping surface that extends away from the exterior surface at an acute angle and a flat, circular surface substantially parallel to the exterior surface, wherein the sloping surface extends between the exterior surface and the flat, circular surface, wherein the custom tubular-shaped body defines a lumen that permits the flow of fluids through the airway when the exterior surface is placed against the interior surface of the particular airway and wherein the exterior surface and interior surface are substantially seamless.

According to a first aspect, the present systems and methods relate to an airway stent, comprising a 3D-printed body that comprises: A) an exterior surface, wherein the exterior surface is placed against the interior surface of an airway; and B) a lumen, wherein the lumen permits the flow of liquids through the airway when the exterior surface is placed against the interior surface of the airway. According to some embodiments, the present systems and methods relate to: 1) an airway stent wherein the 3D-printed body comprises a bioinert material; 2) an airway stent wherein the exterior surface and lumen are seamless; 3) an airway stent wherein the 3D-printed body is generally tubular-shaped; 4) an airway stent wherein the exterior surface comprises a plurality of protrusions that extend away from the exterior surface at an acute angle; 5) an airway stent wherein the plurality of protrusions are generally frustum-shaped; 6) an airway stent wherein the plurality of protrusions comprise juxtaposed frustums; 7) an airway stent wherein the plurality of protrusions comprise helical ridges; 8) an airway stent wherein the exterior surface defines a plurality of cutouts that extend from the exterior surface through the 3D-printed body to the lumen; 9) an airway stent wherein the cutouts are generally diamond-shaped; and/or 10) an airway stent wherein the exterior surface is custom-shaped according to the dimensions of a patient airway.

These and other aspects, features, and benefits of the claimed systems and methods will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1A:
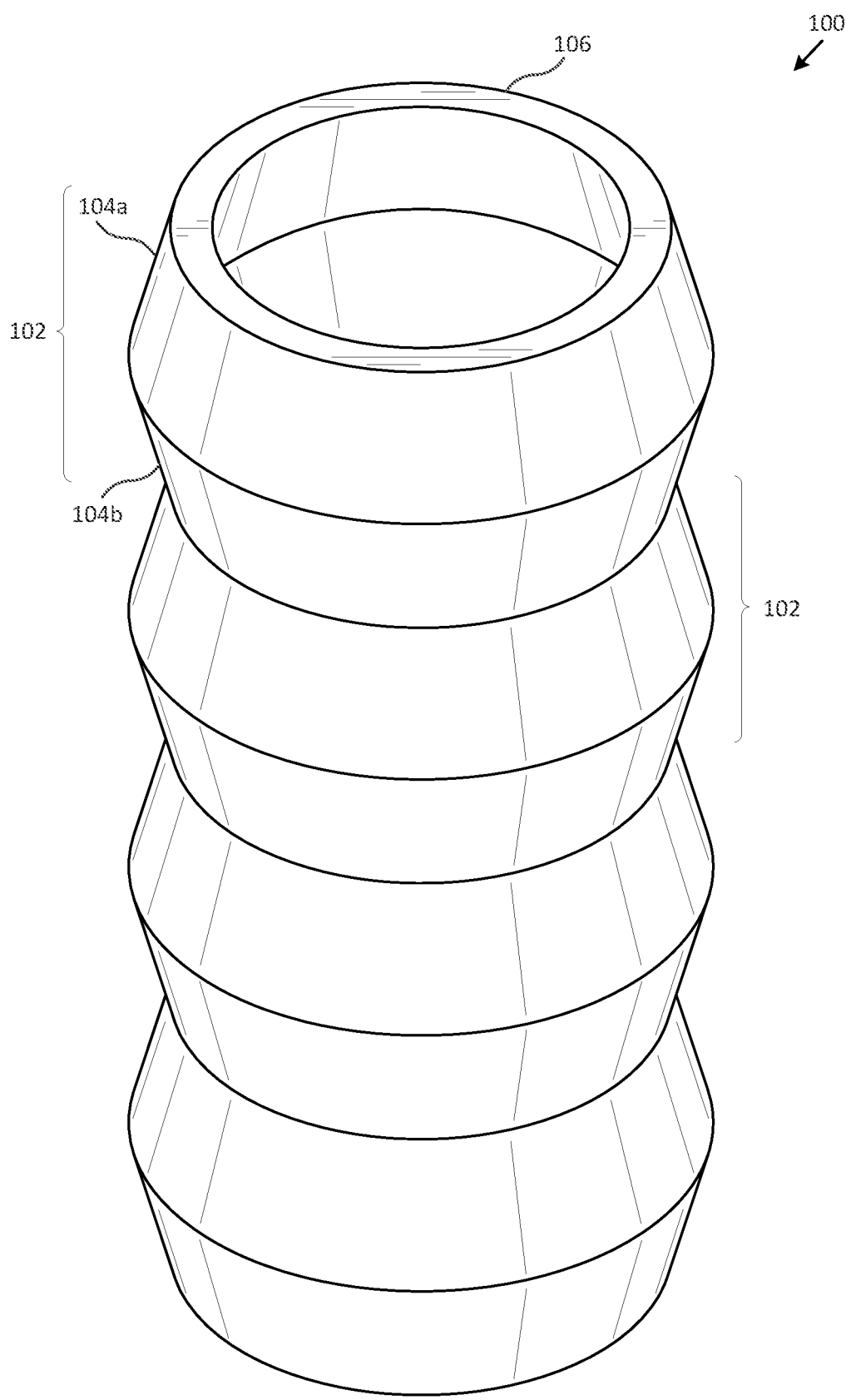
FIG. 1 (including FIGS. 1A-1G) illustrates an exemplary accordion stent, according to one embodiment of the present disclosure.
Figure 1B:
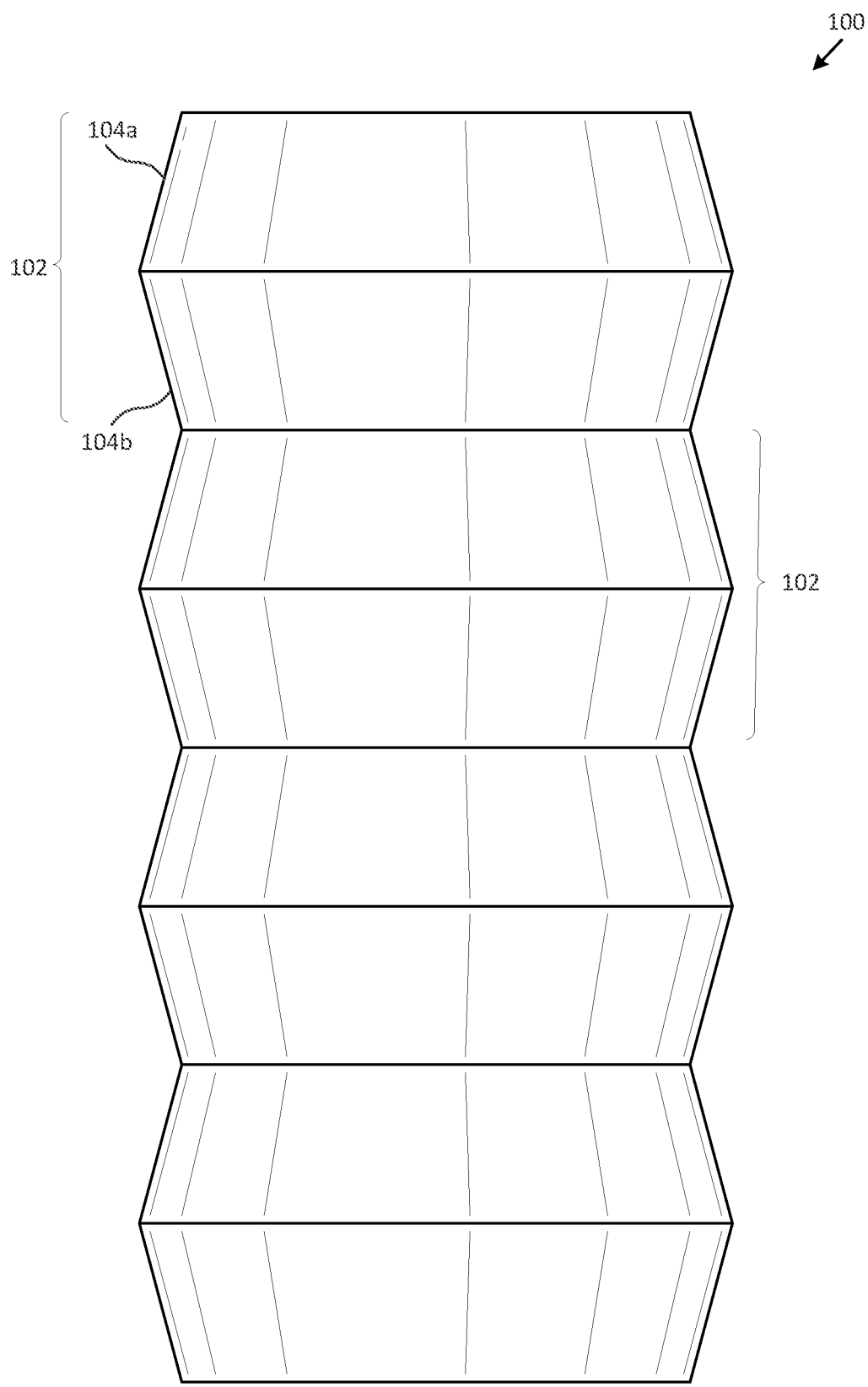
Figure 1C:
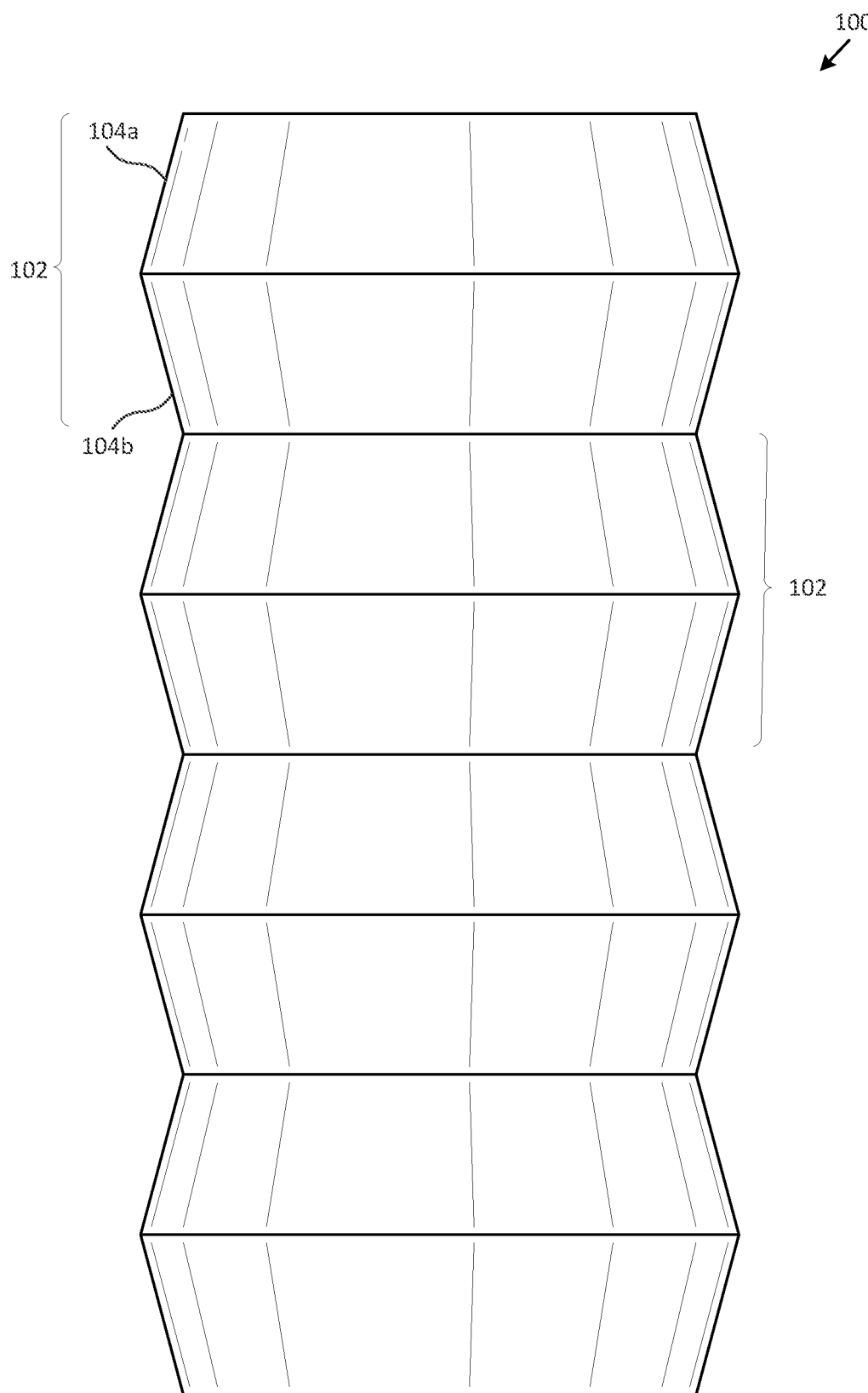
Figure 1D:
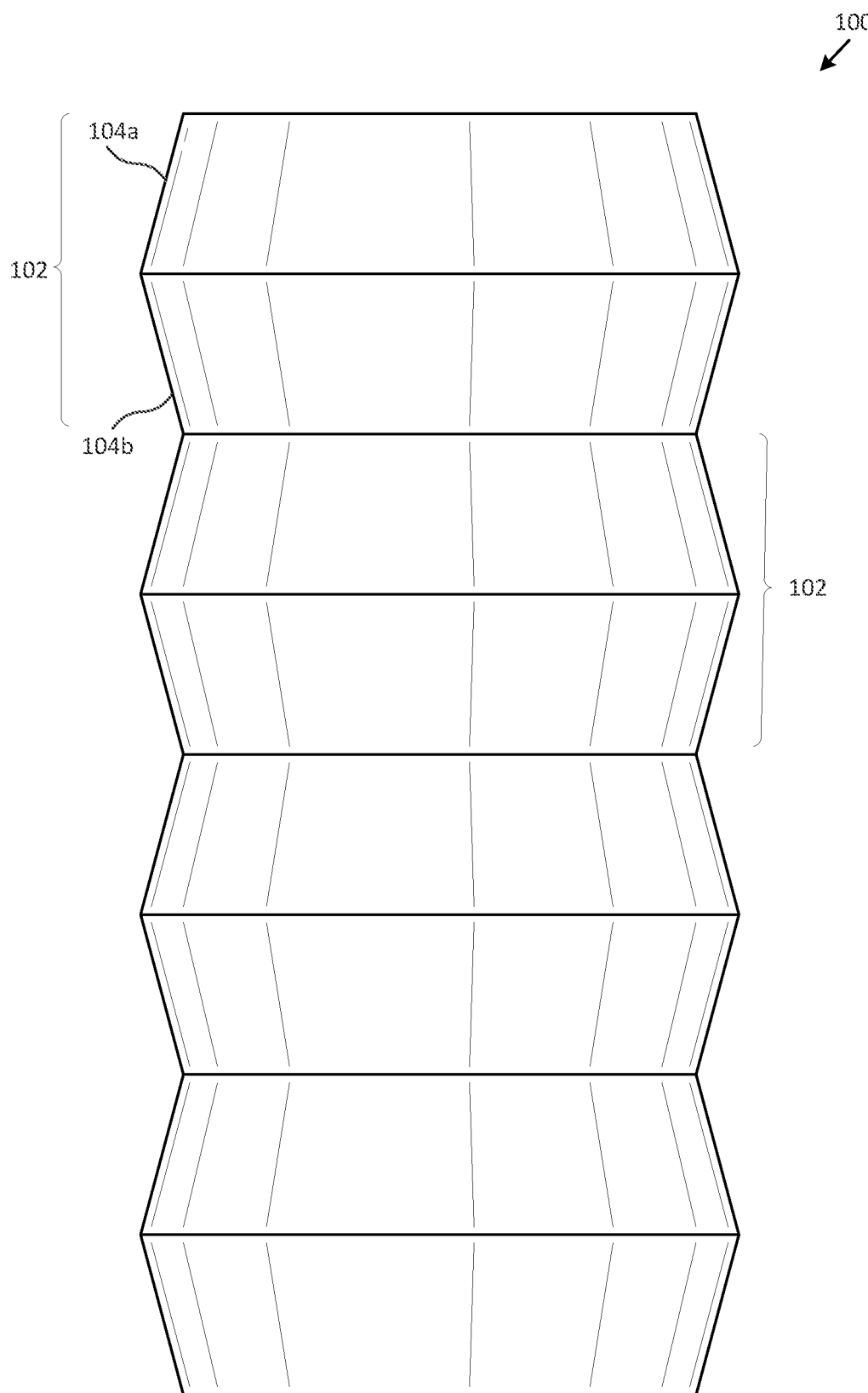
Figure 1E:
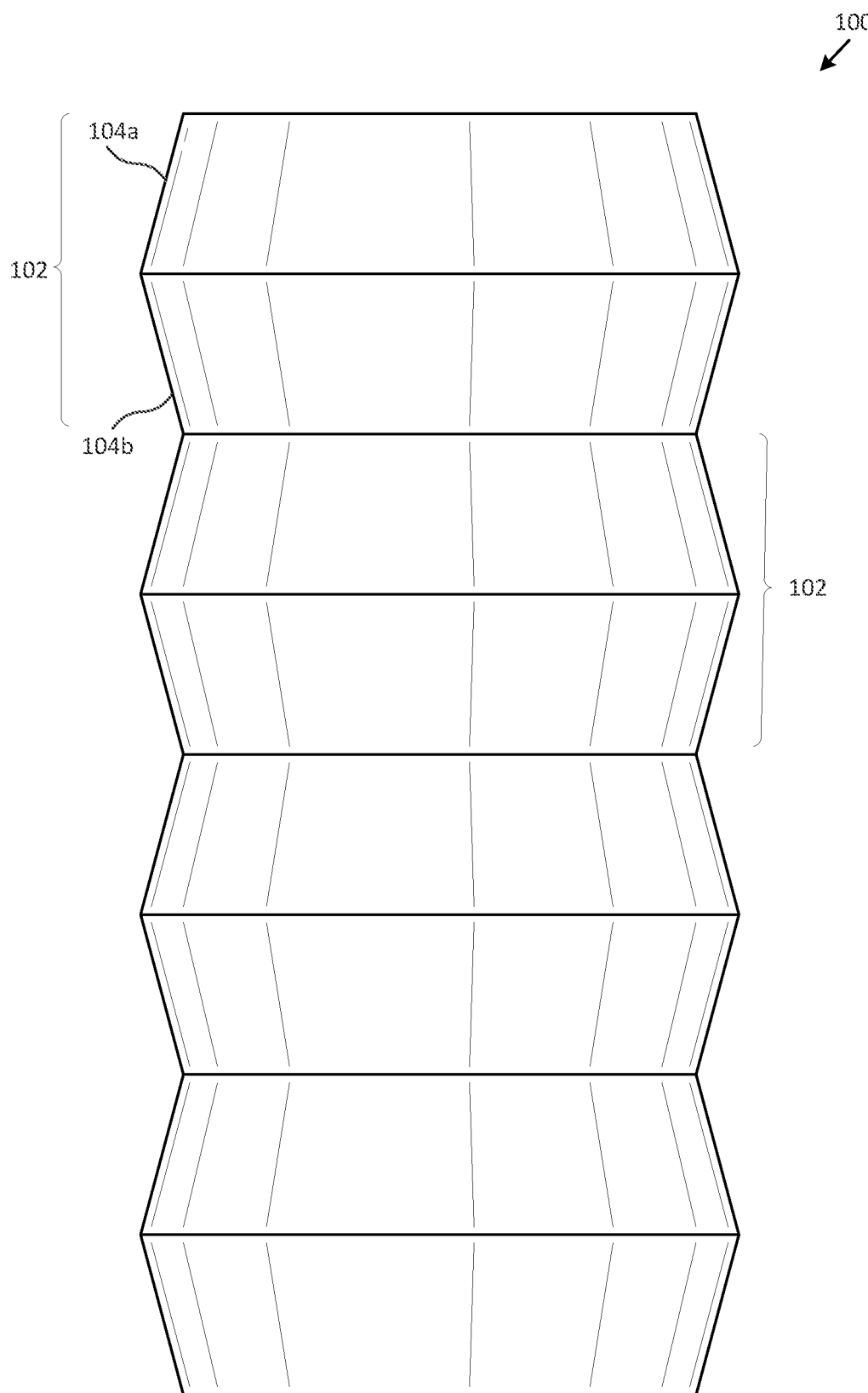
Figure 1F:
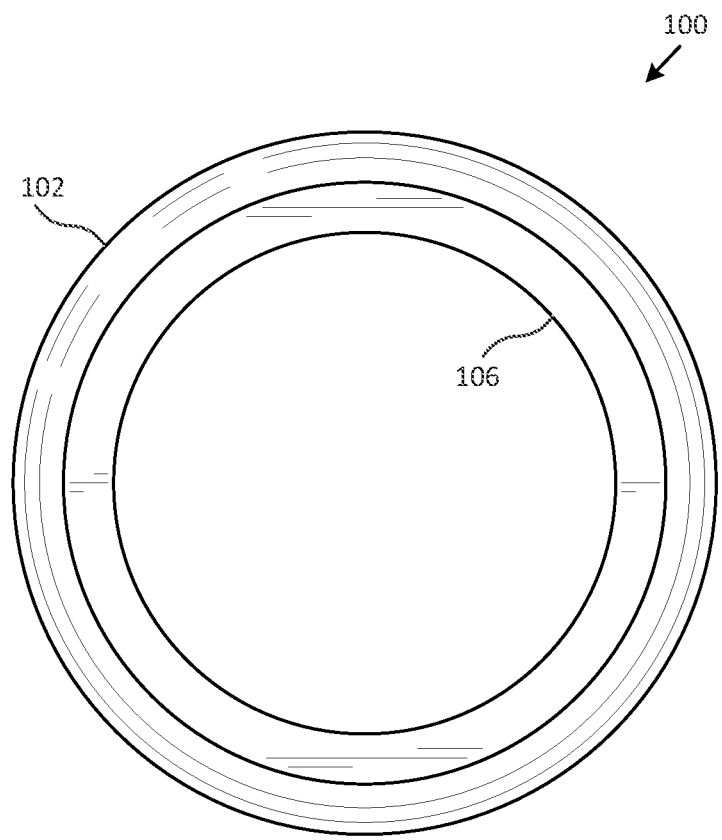
Figure 1G:
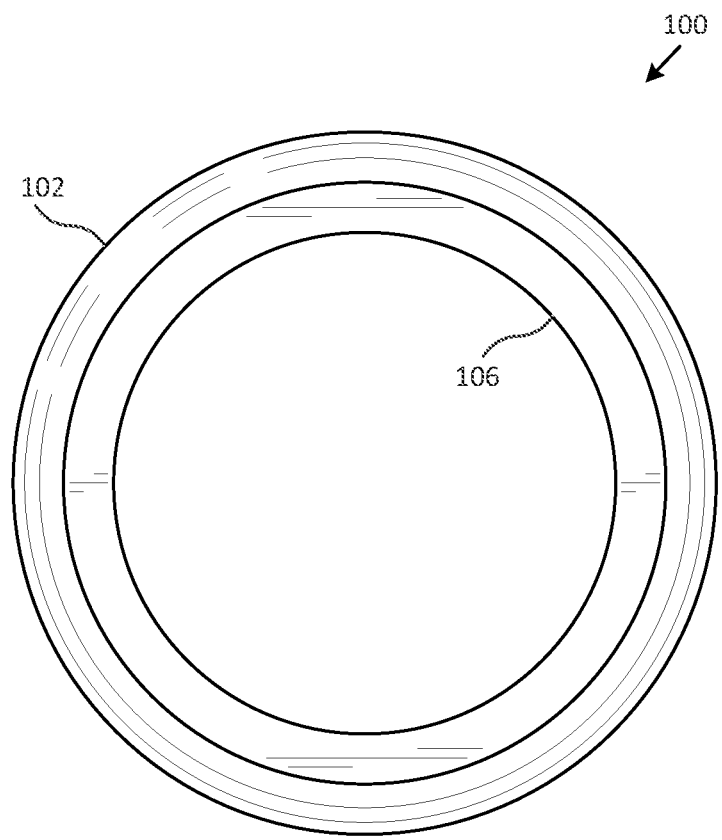
Figure 2A:
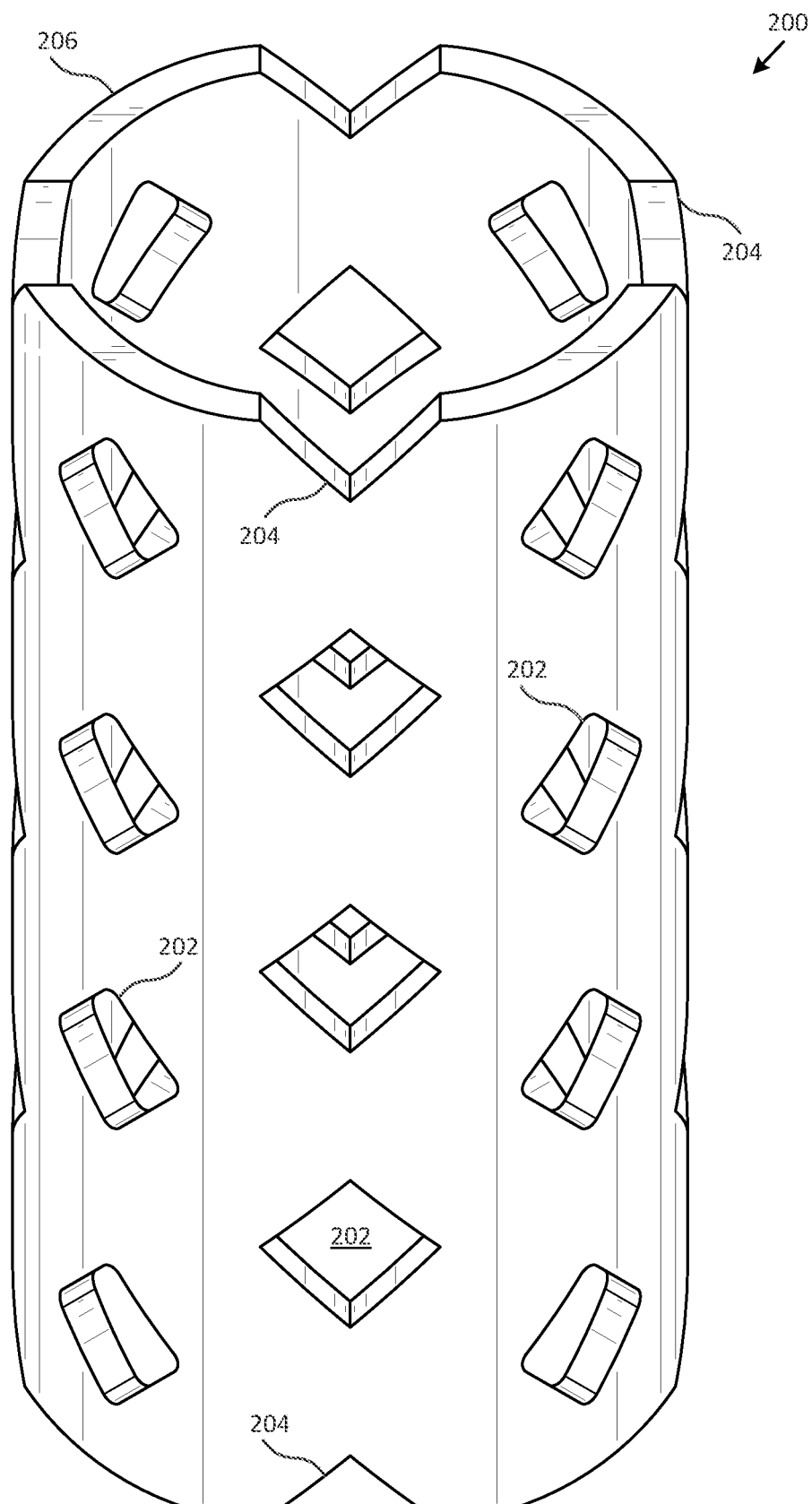
FIG. 2 (including FIGS. 2A-2G) illustrates an exemplary cutout stent, according to one embodiment of the present disclosure.
Figure 2B:
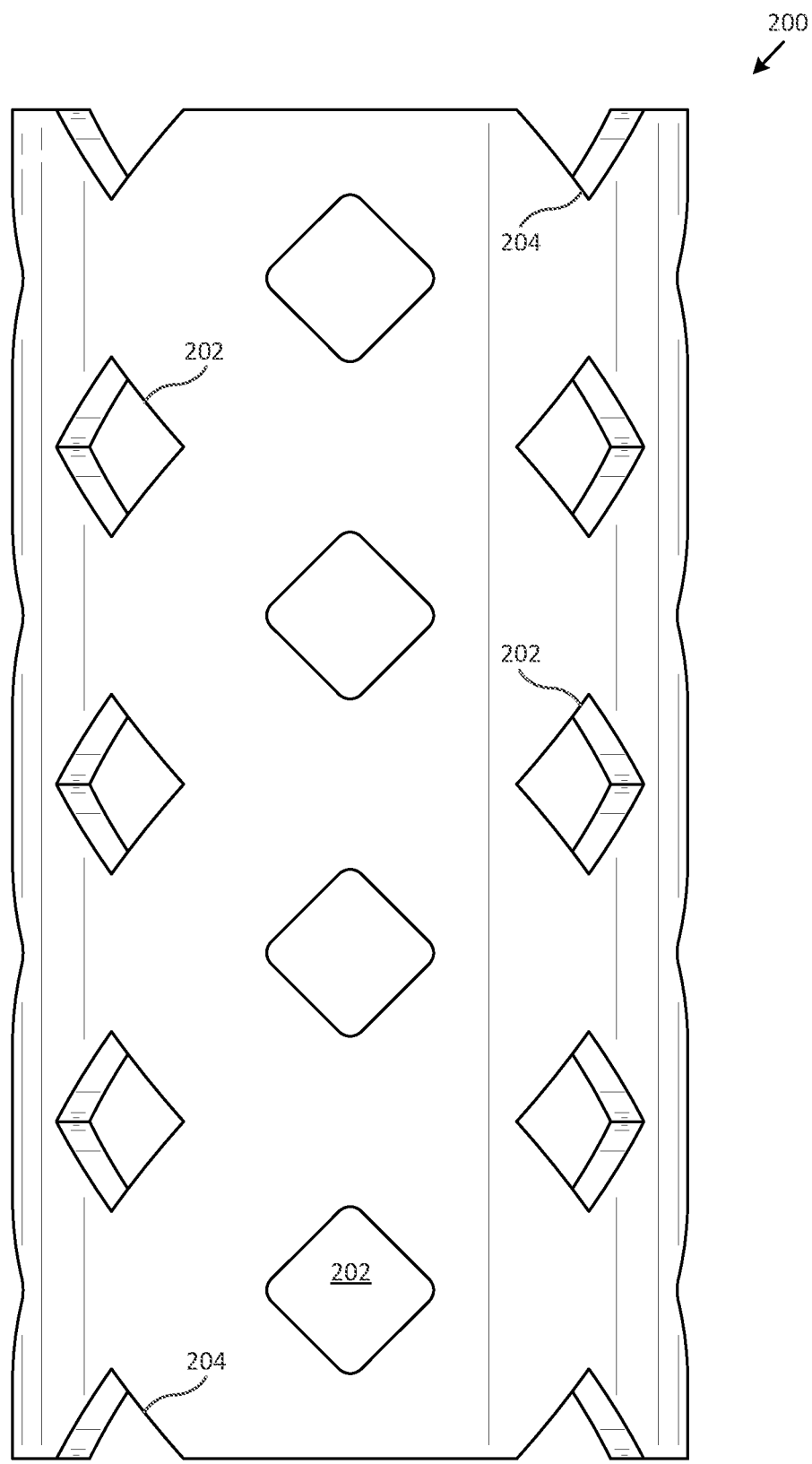
Figure 2C:
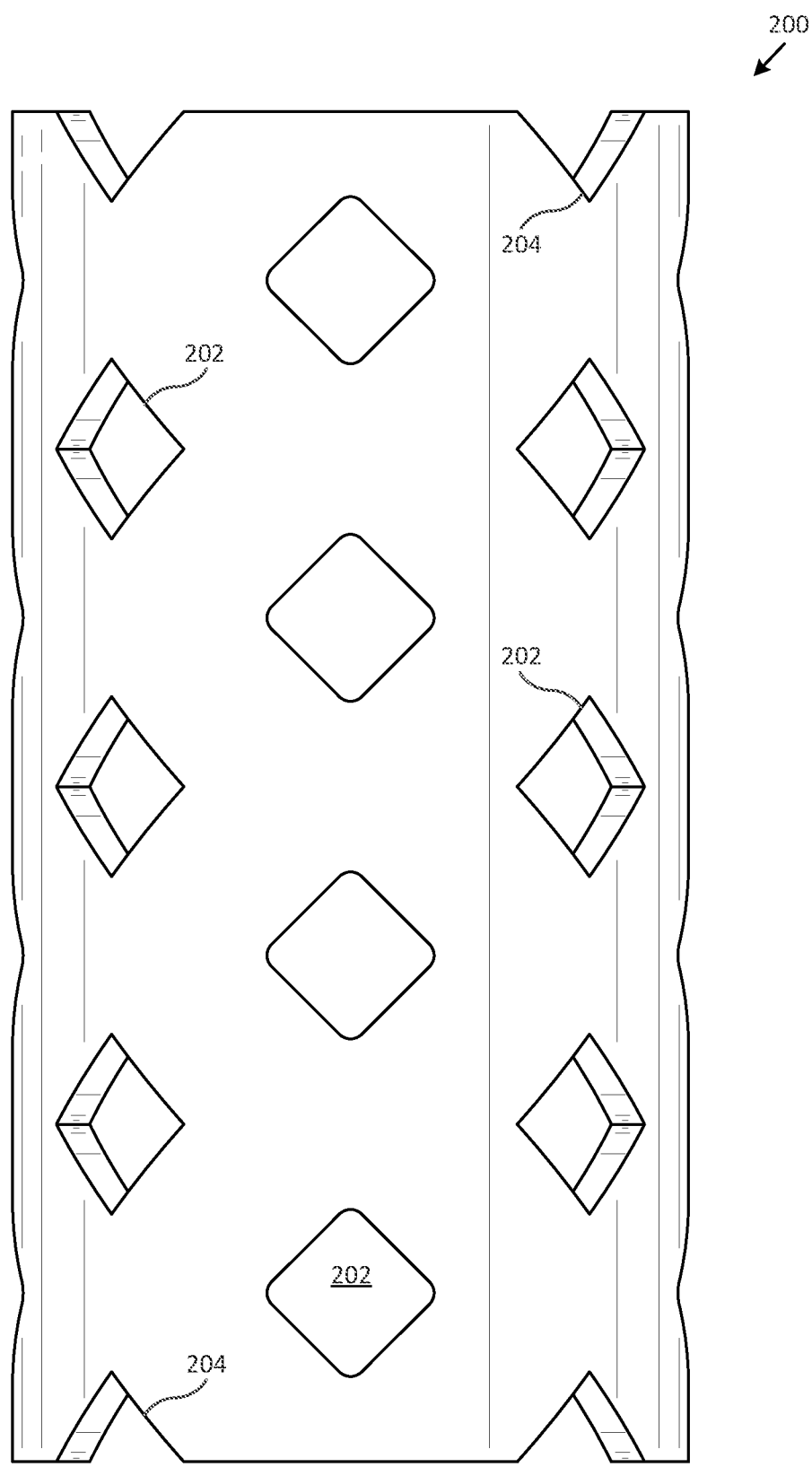
Figure 2D:
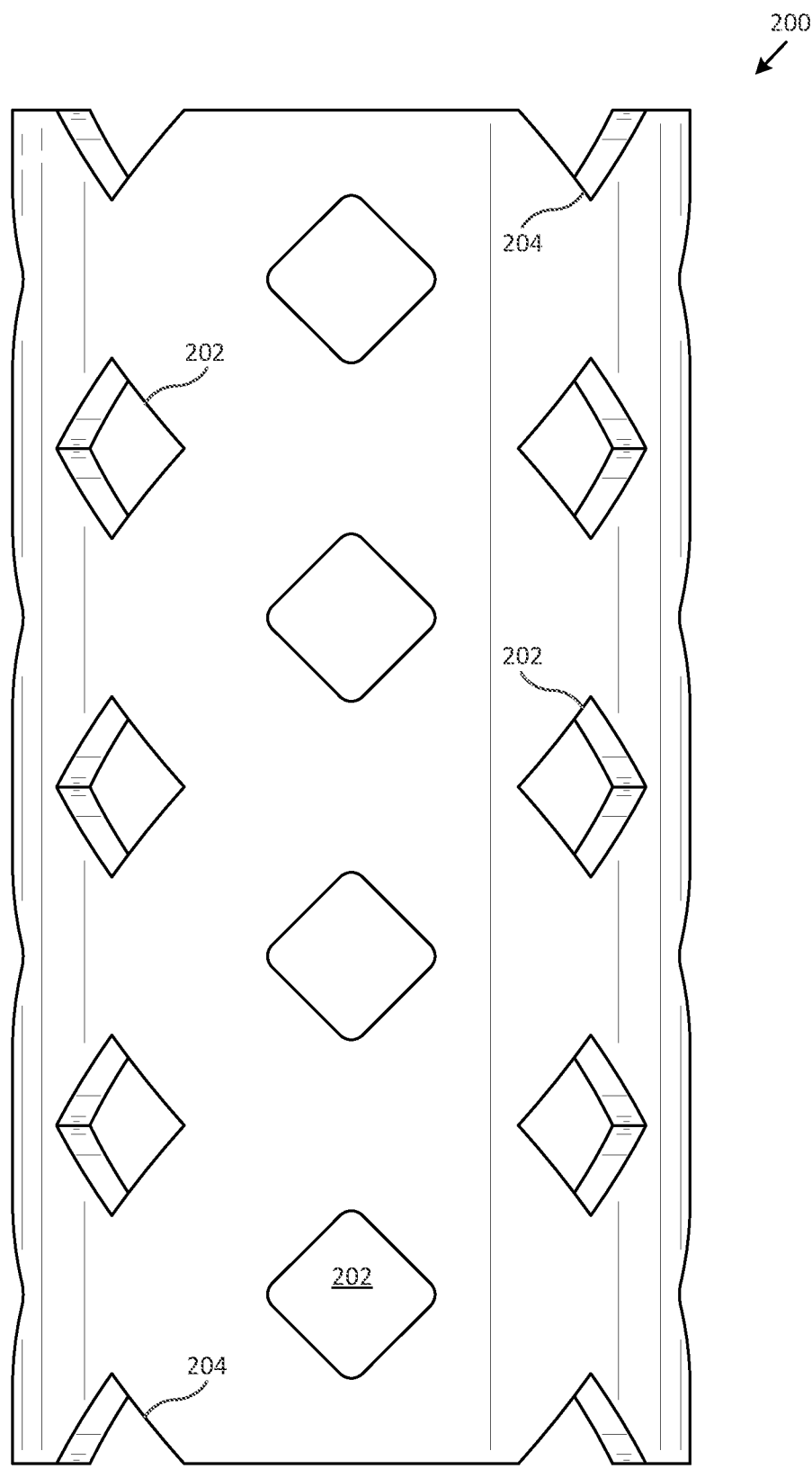
Figure 2E:
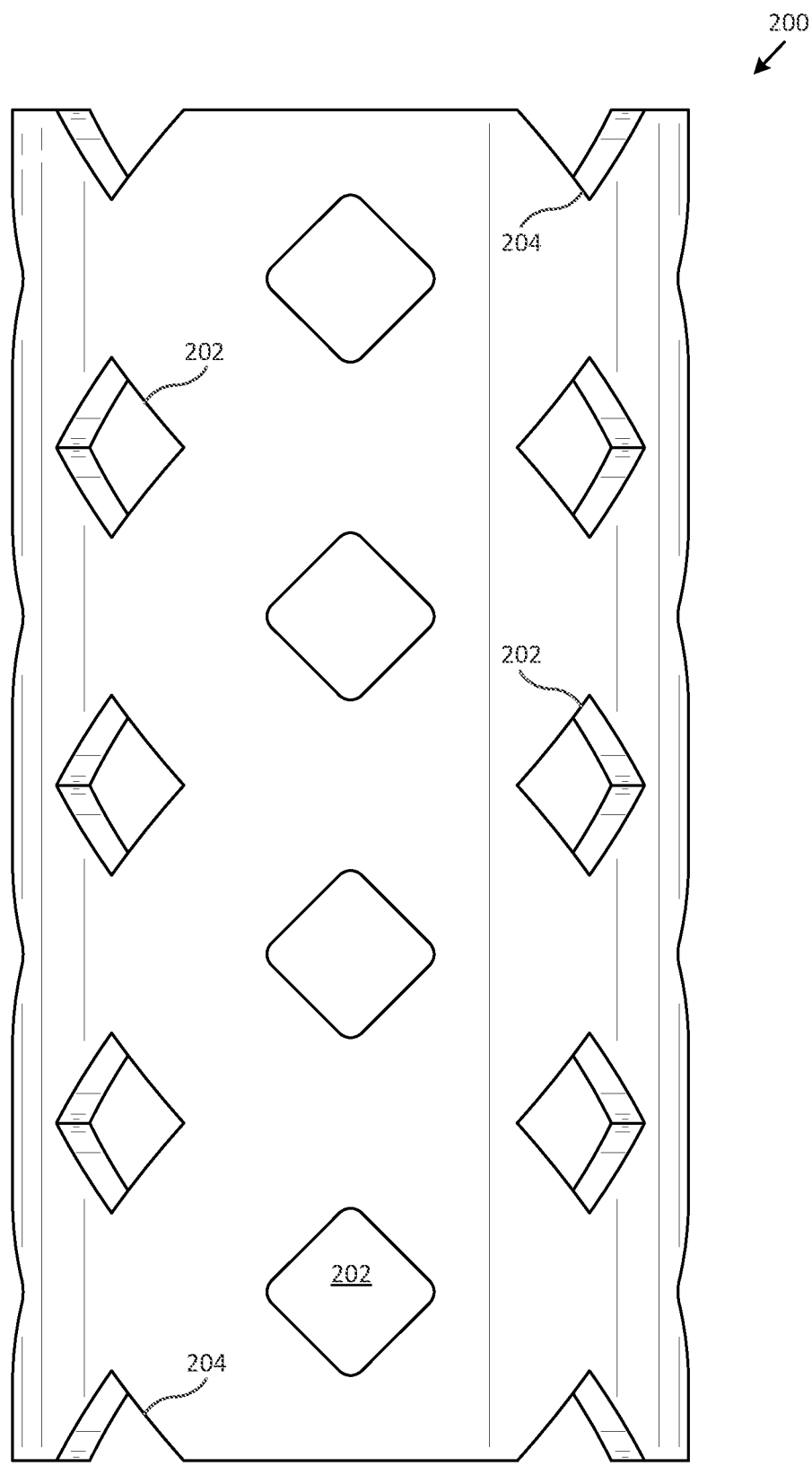
Figure 2F:
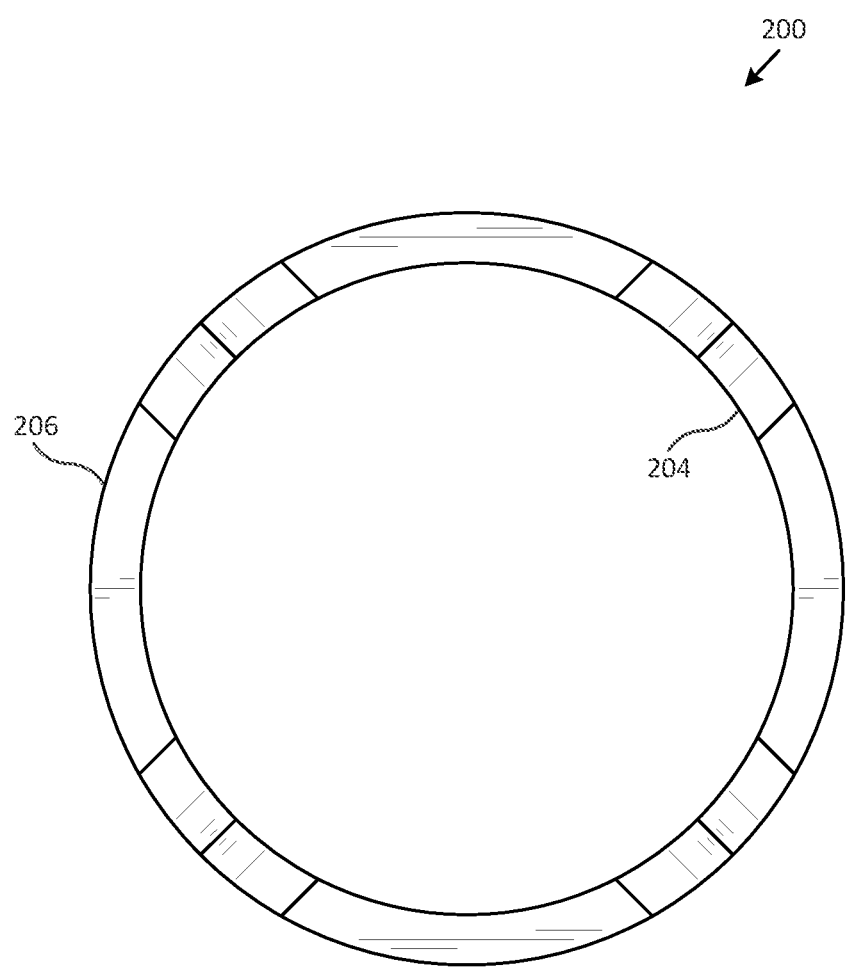
Figure 2G:
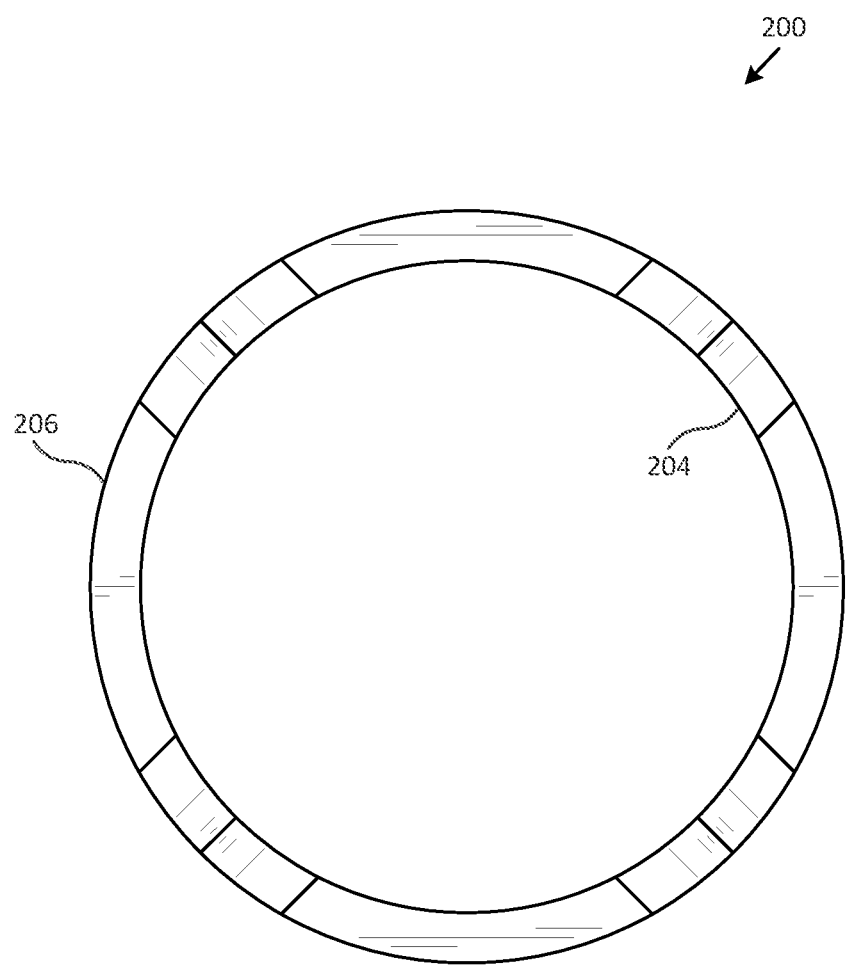
Figure 3A:
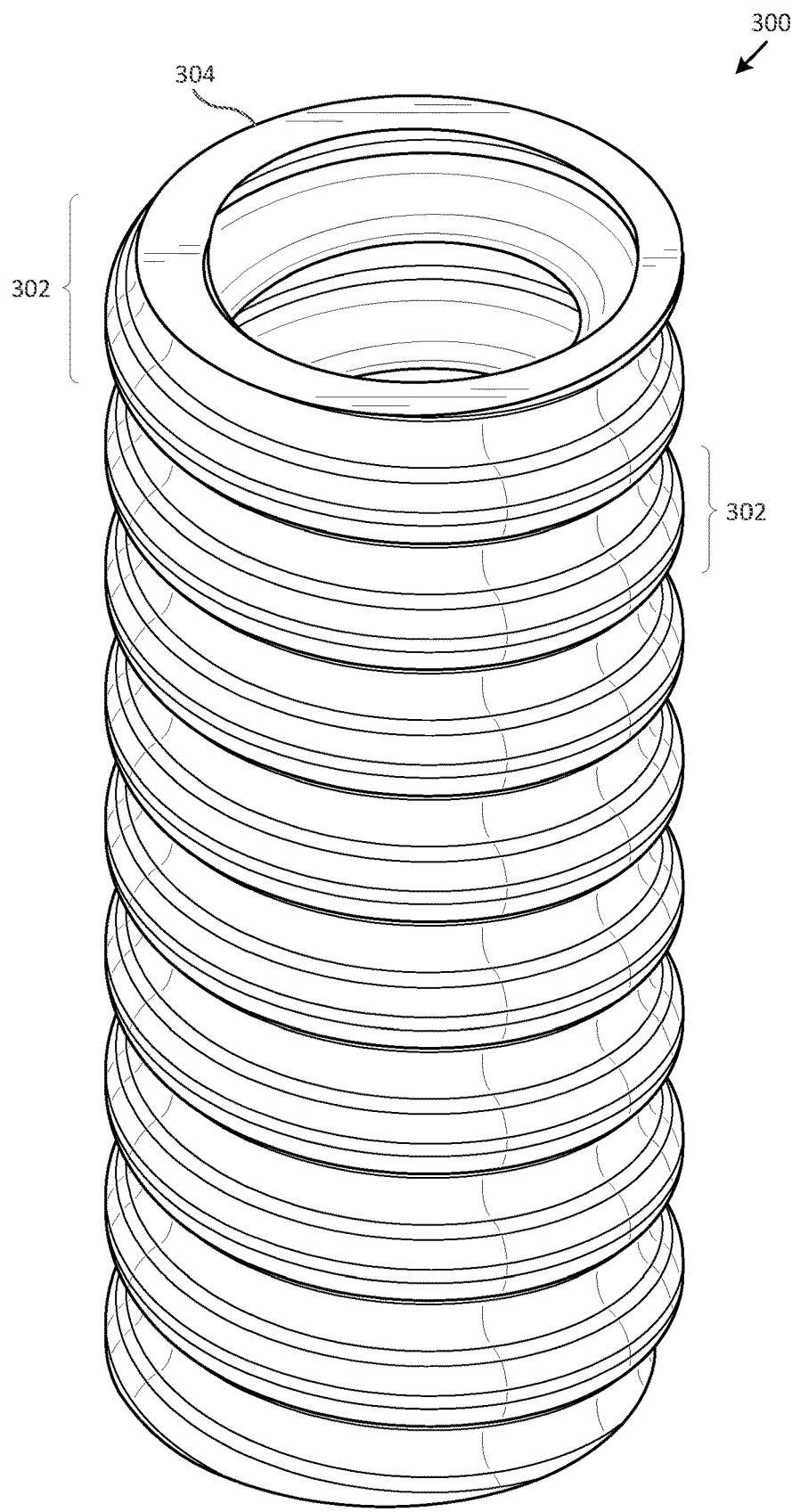
FIG. 3 (including FIGS. 3A-3G) illustrates an exemplary spiral stent, according to one embodiment of the present disclosure.
Figure 3B:
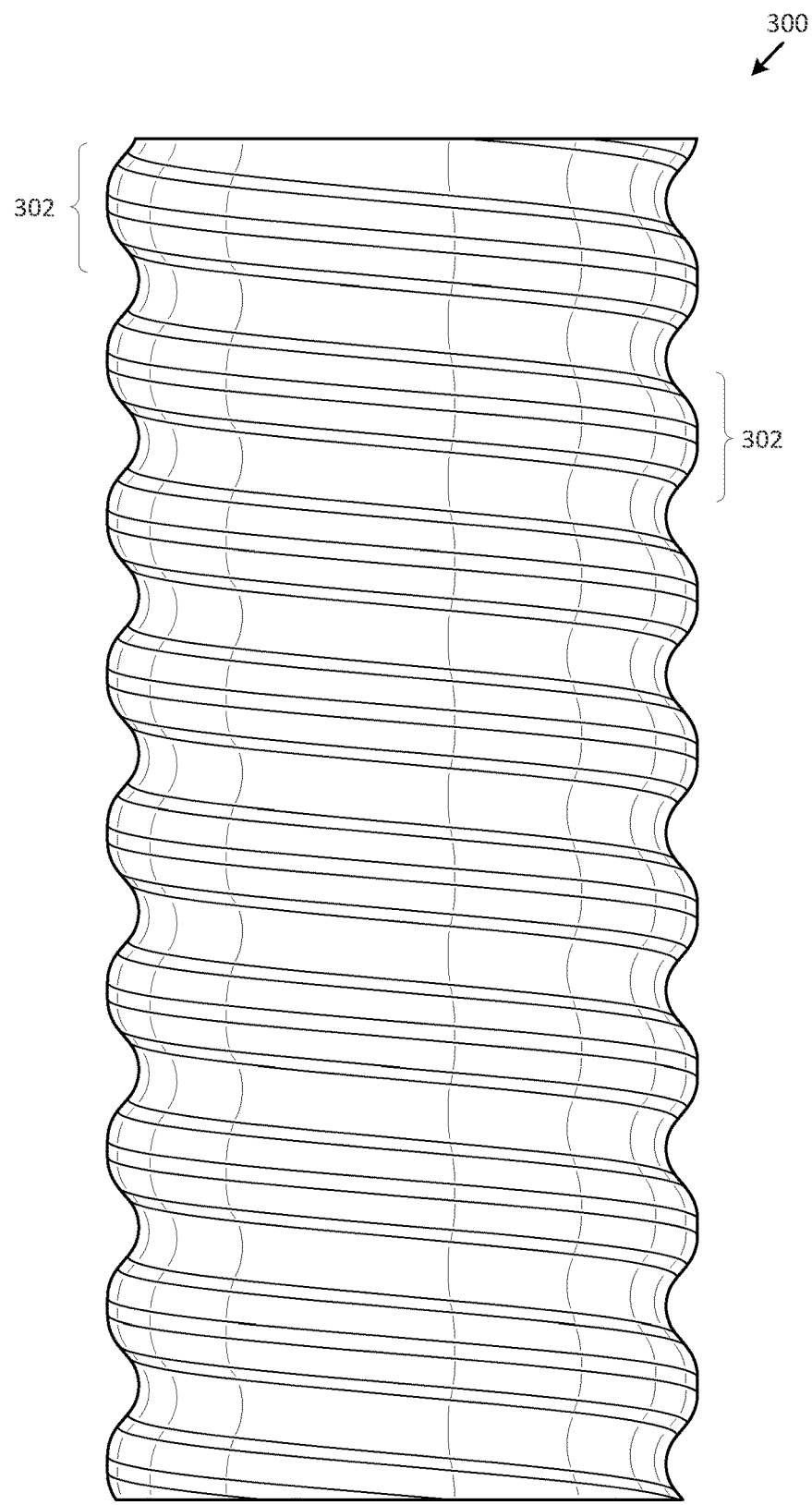
Figure 3C:
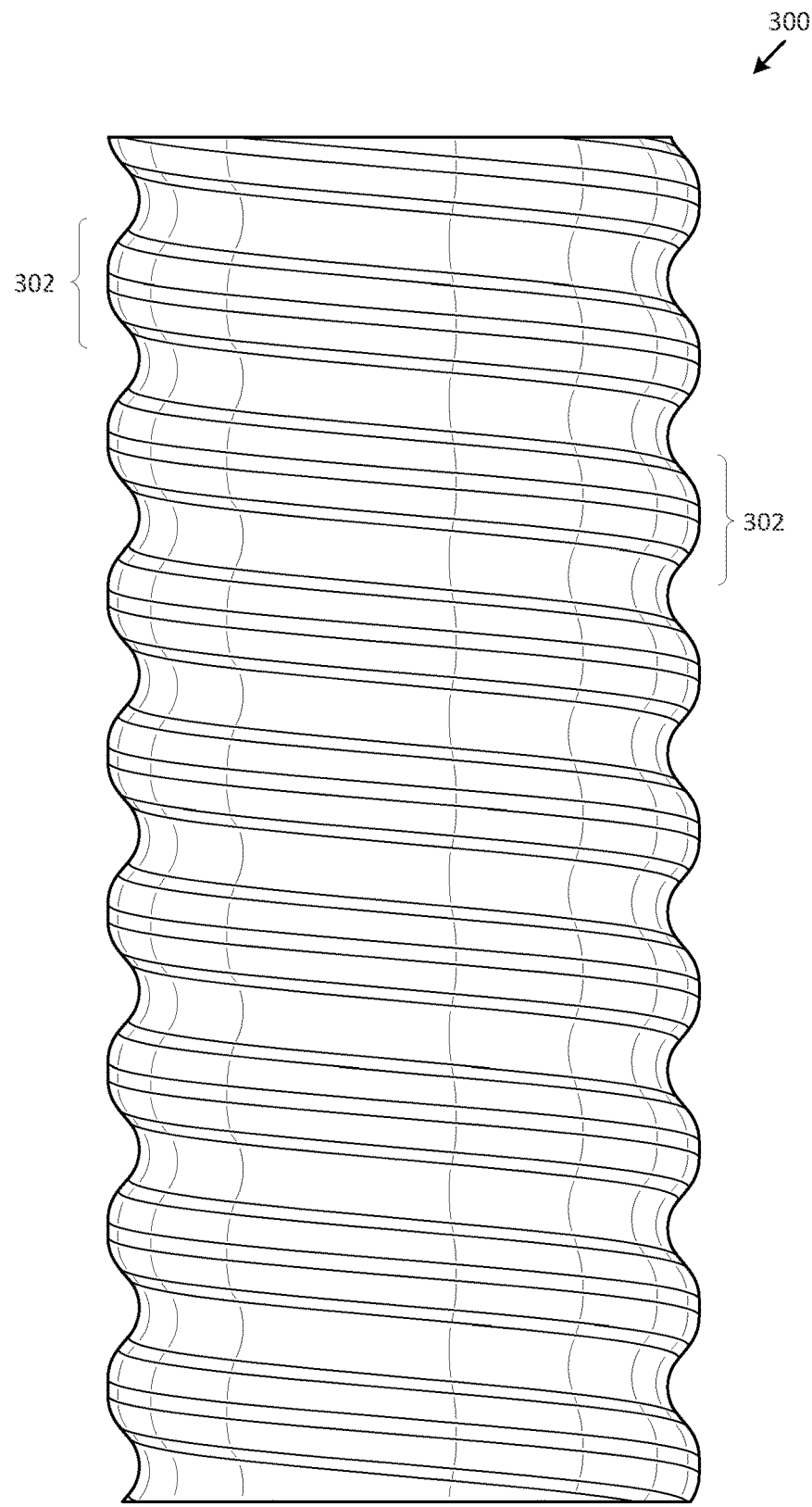
Figure 3D:
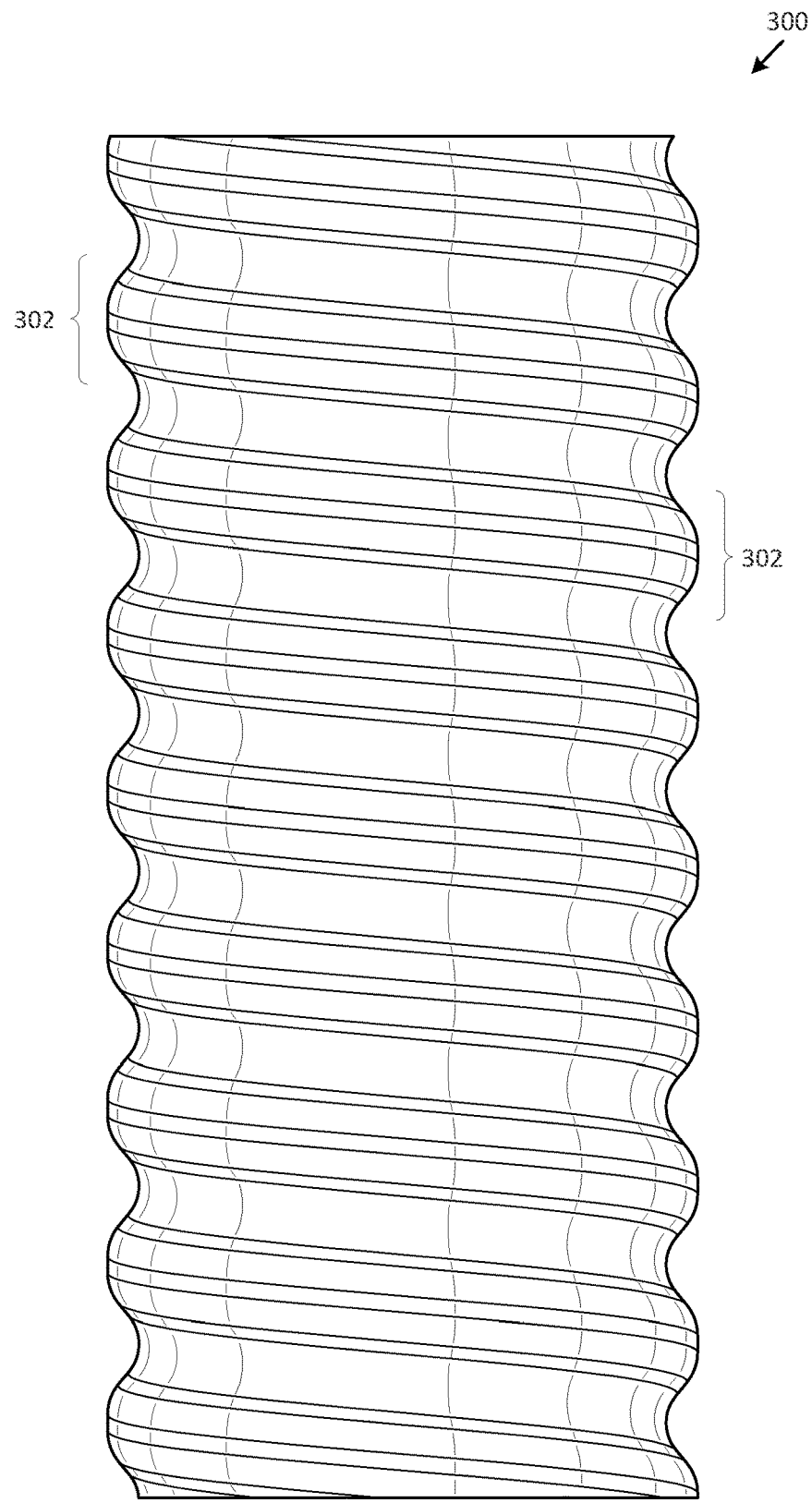
Figure 3E:
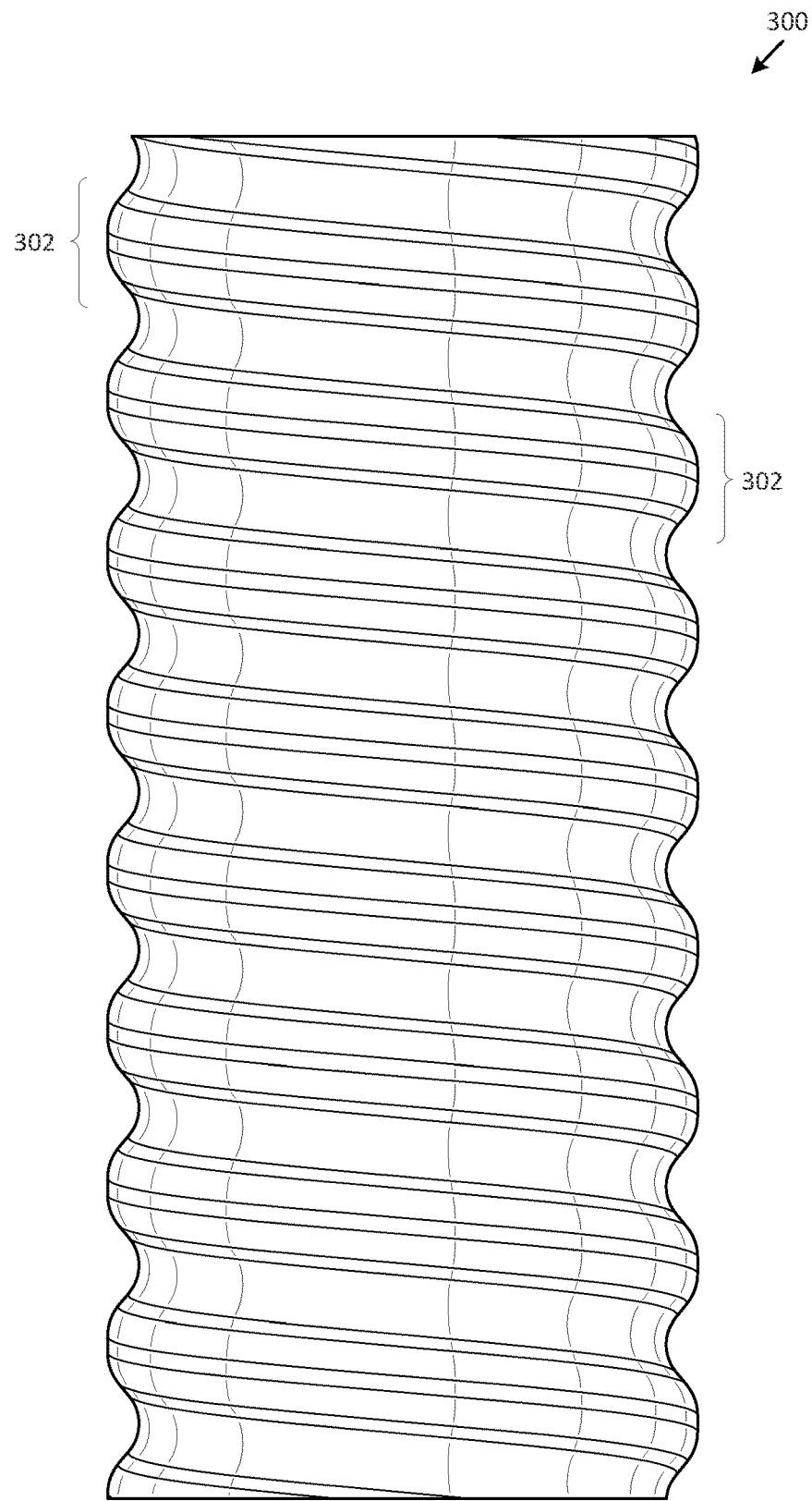
Figure 3F:
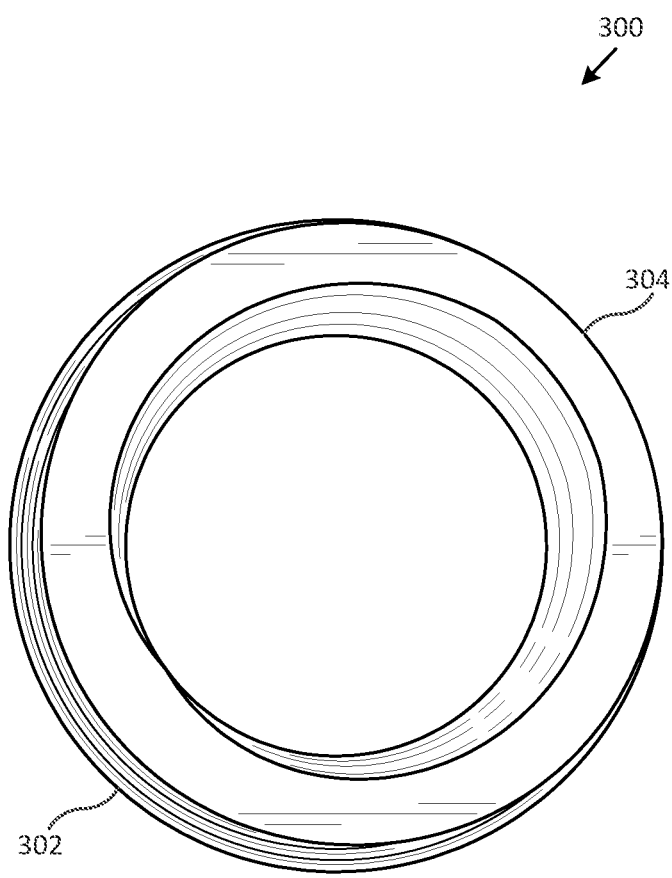
Figure 3G:
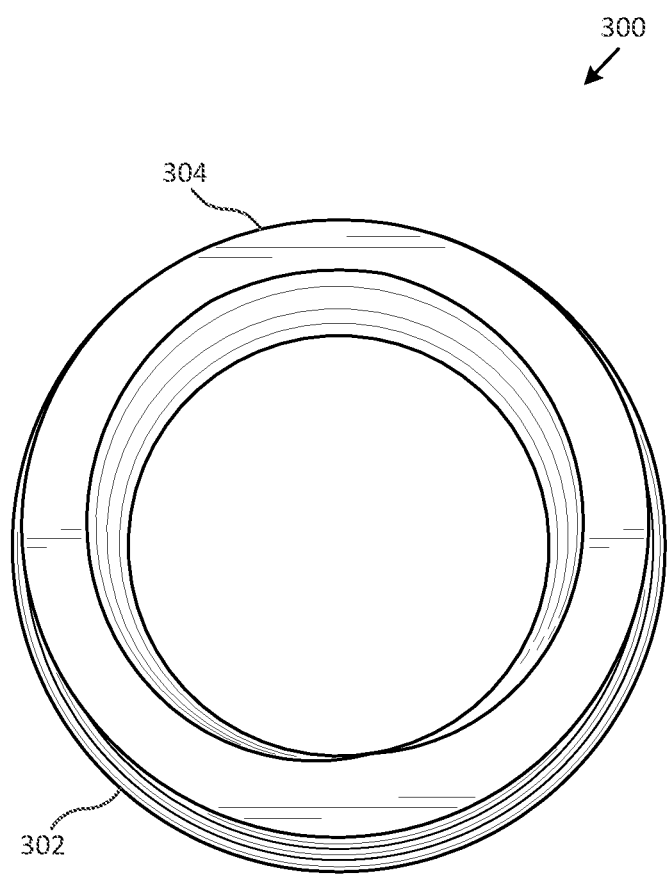
Figure 4A:
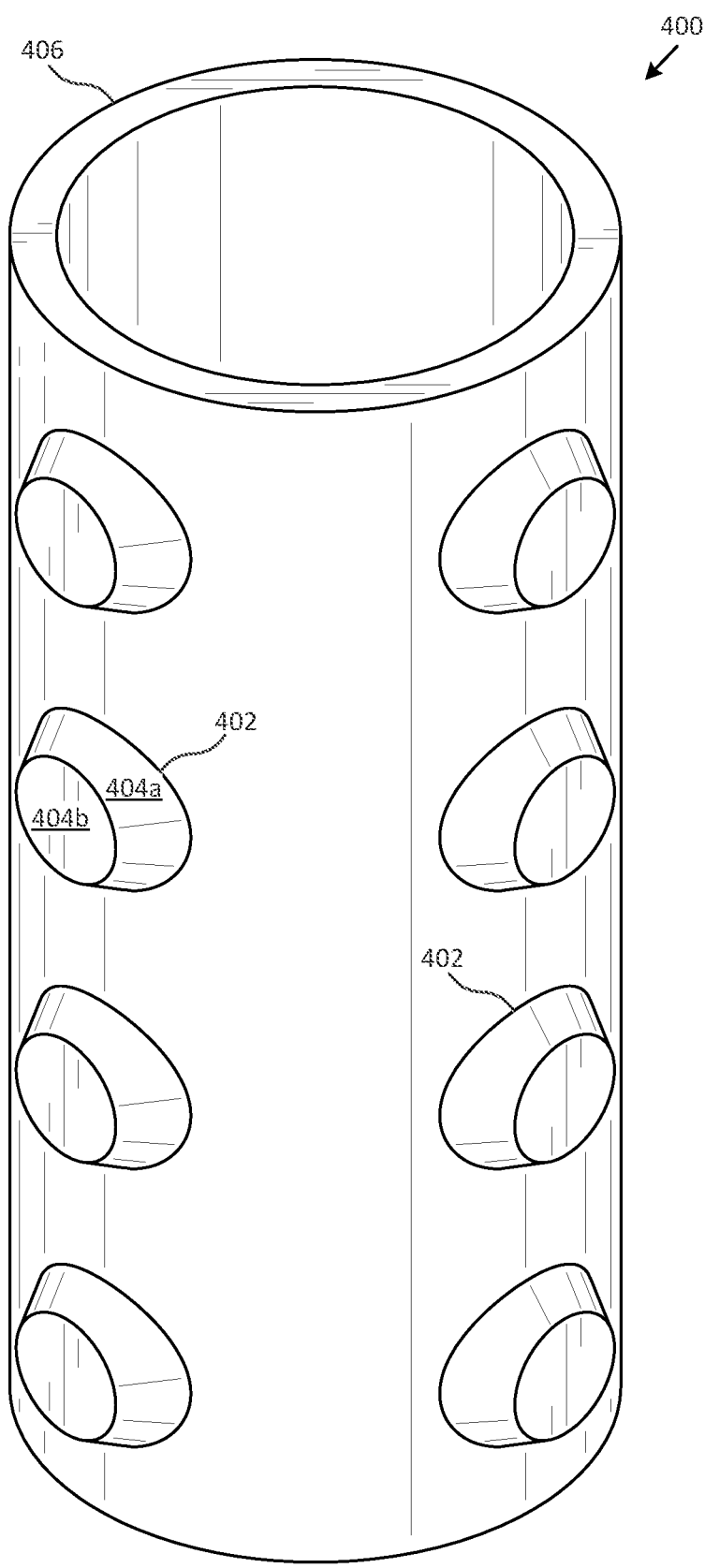
FIG. 4 (including FIGS. 4A-4G) illustrates an exemplary studded stent, according to one embodiment of the present disclosure.
Figure 4B:
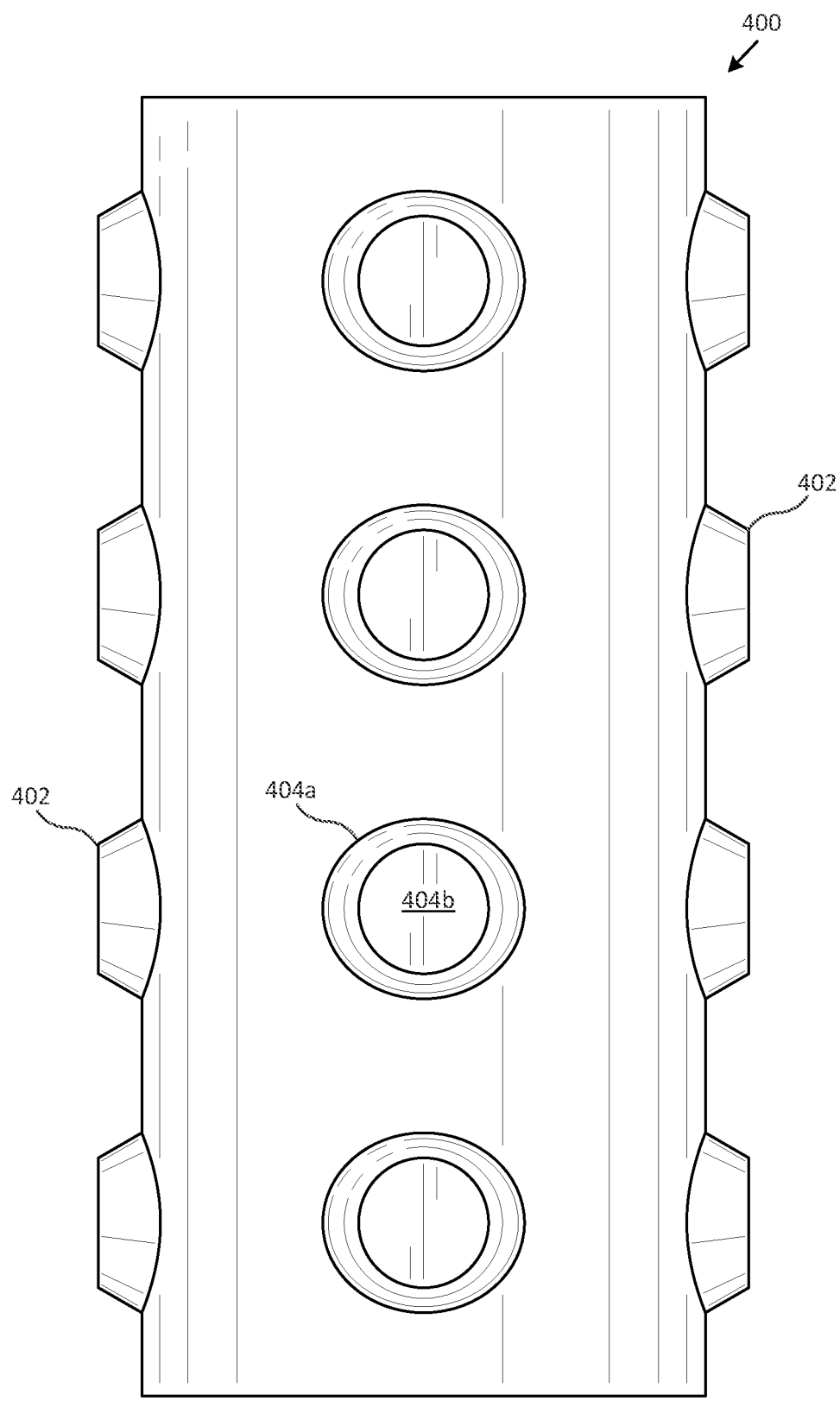
Figure 4C:
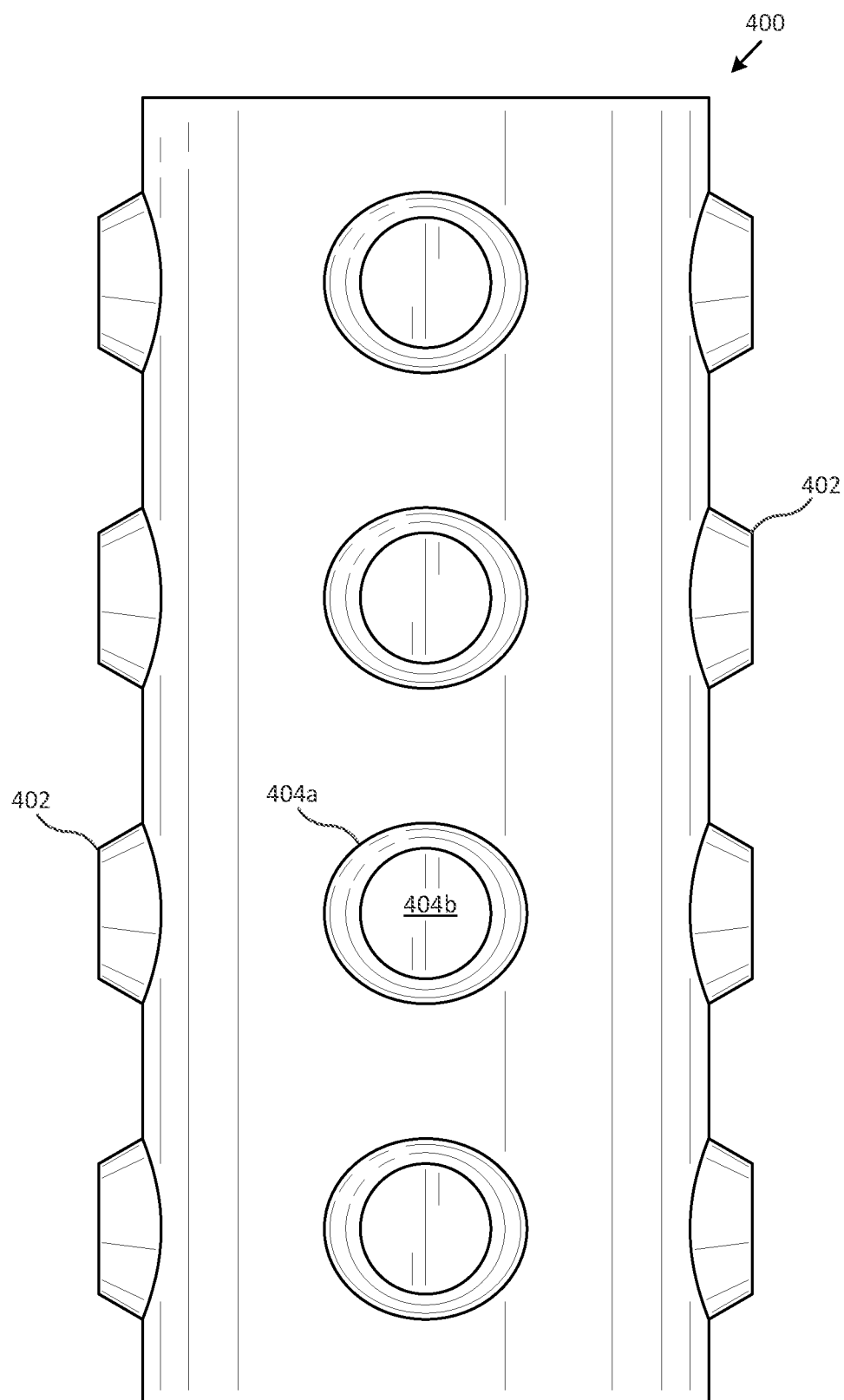
Figure 4D:
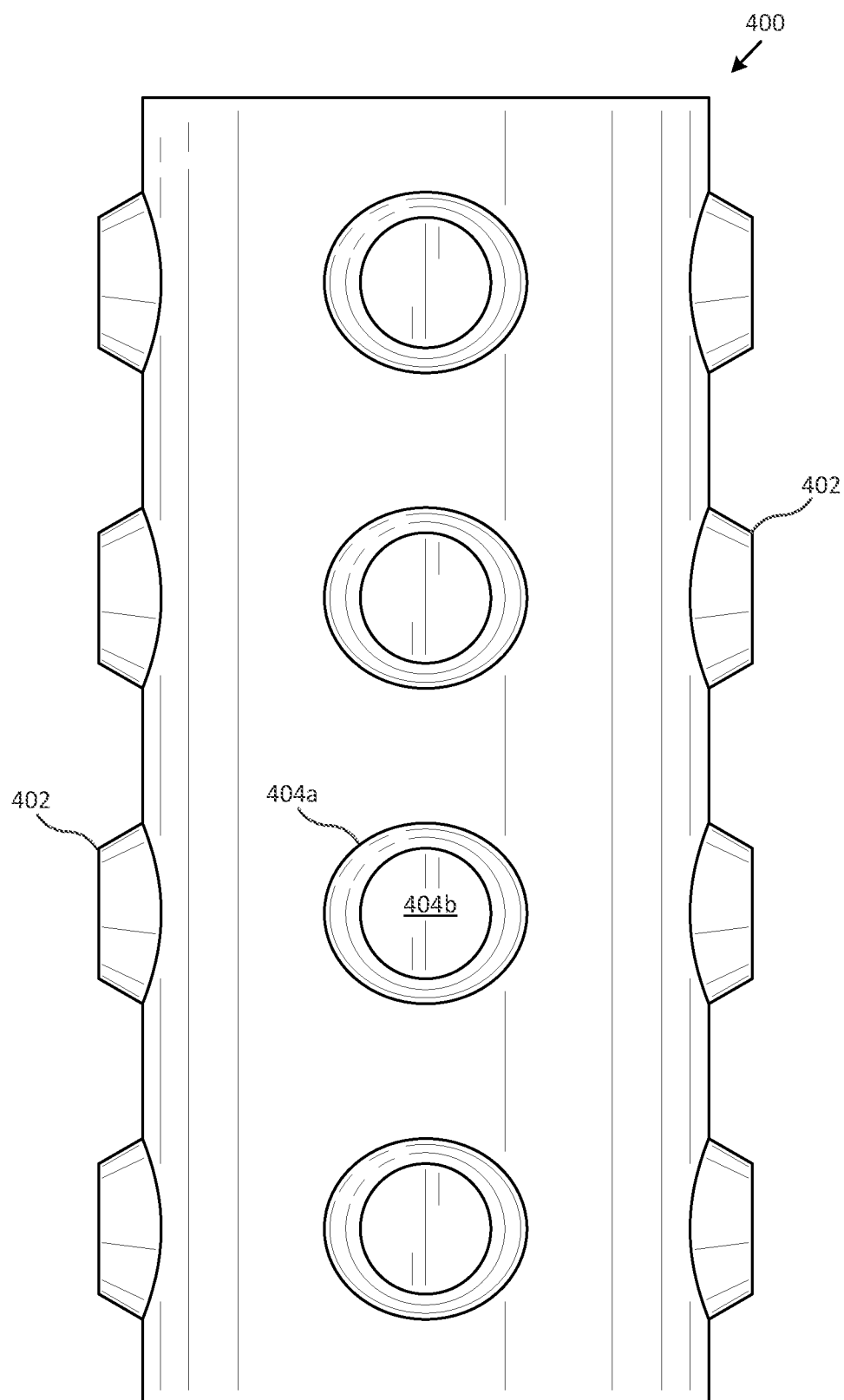
Figure 4E:
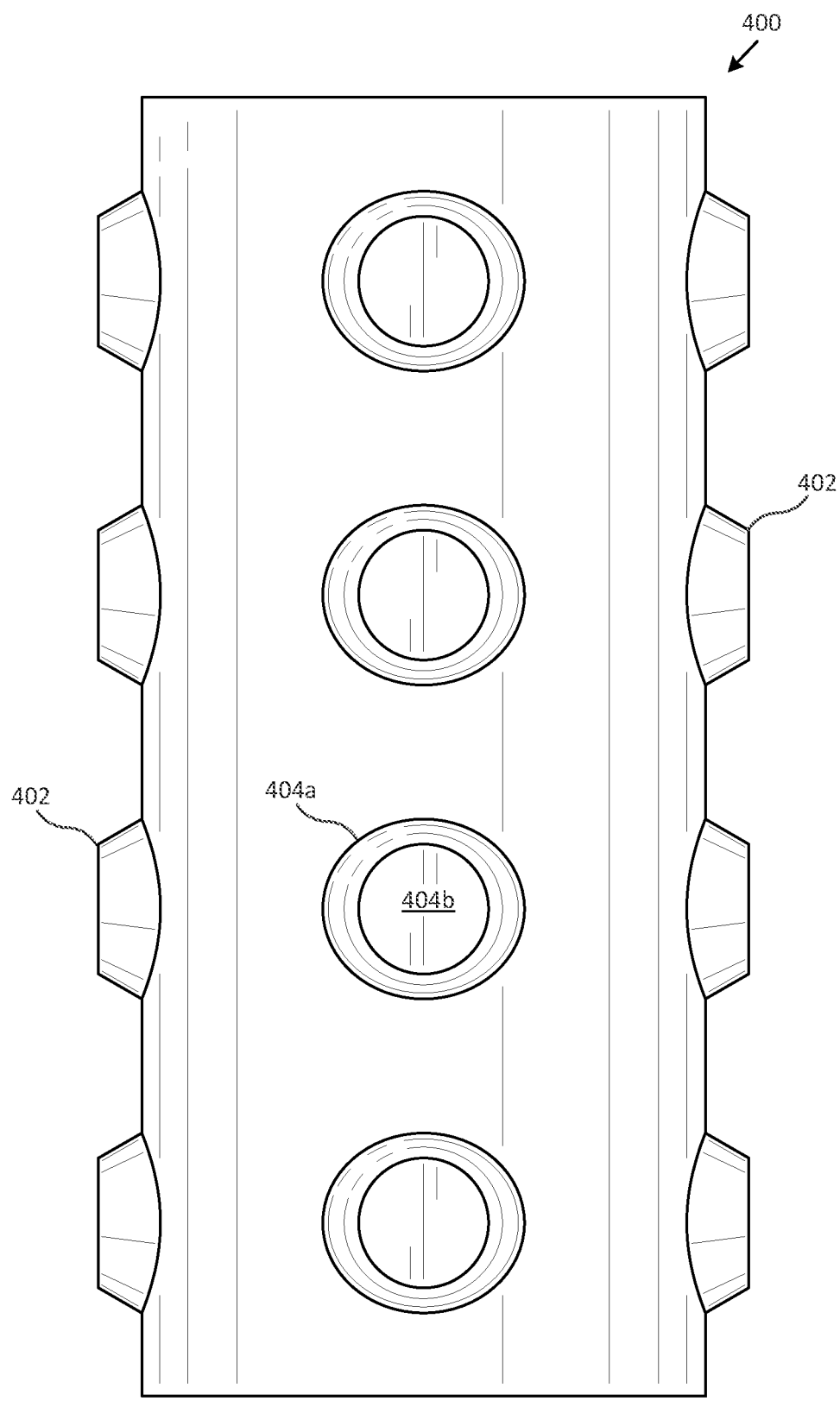
Figure 4F:
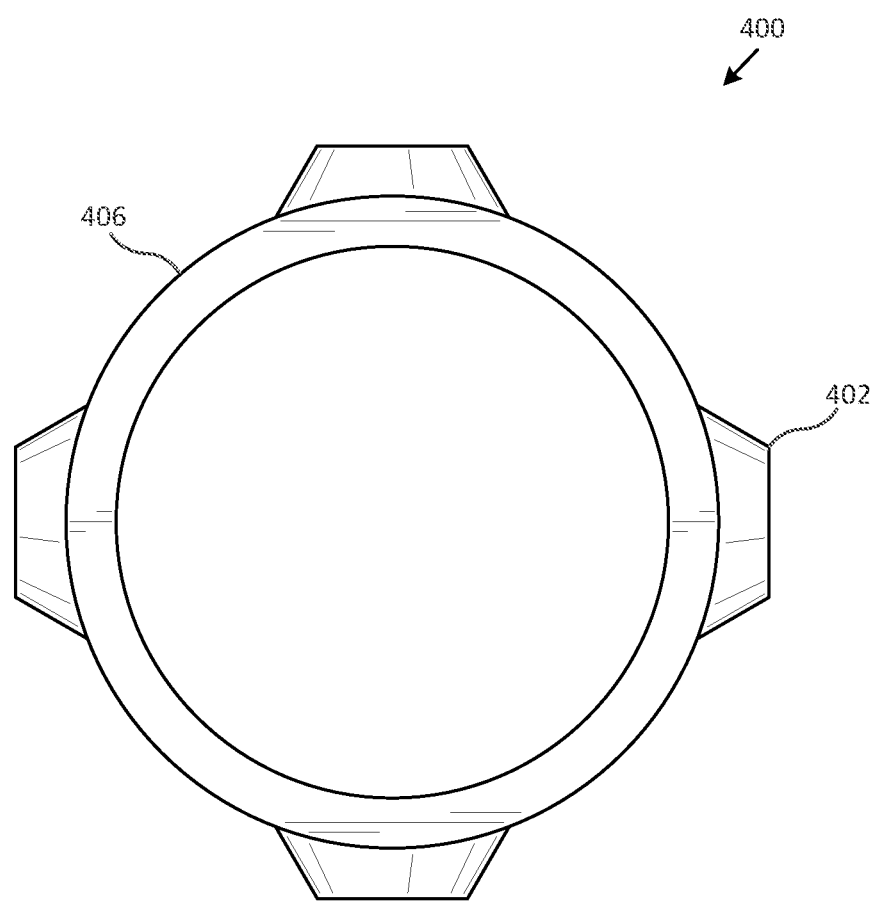
Figure 4G:
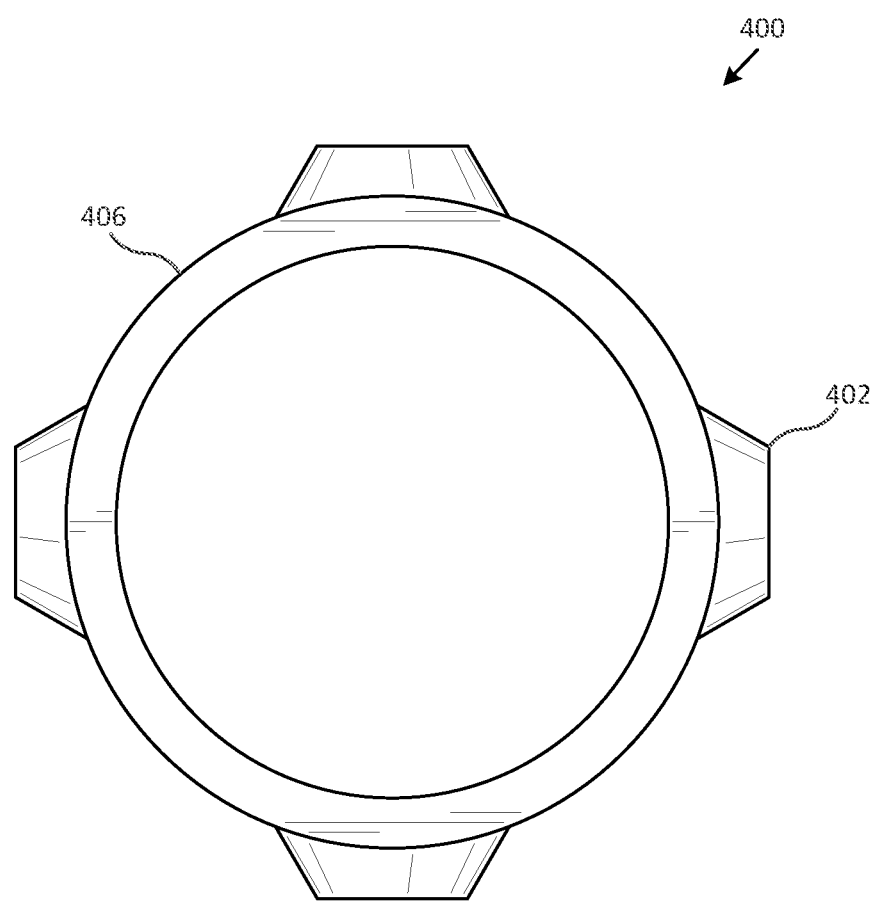
Figure 5A:
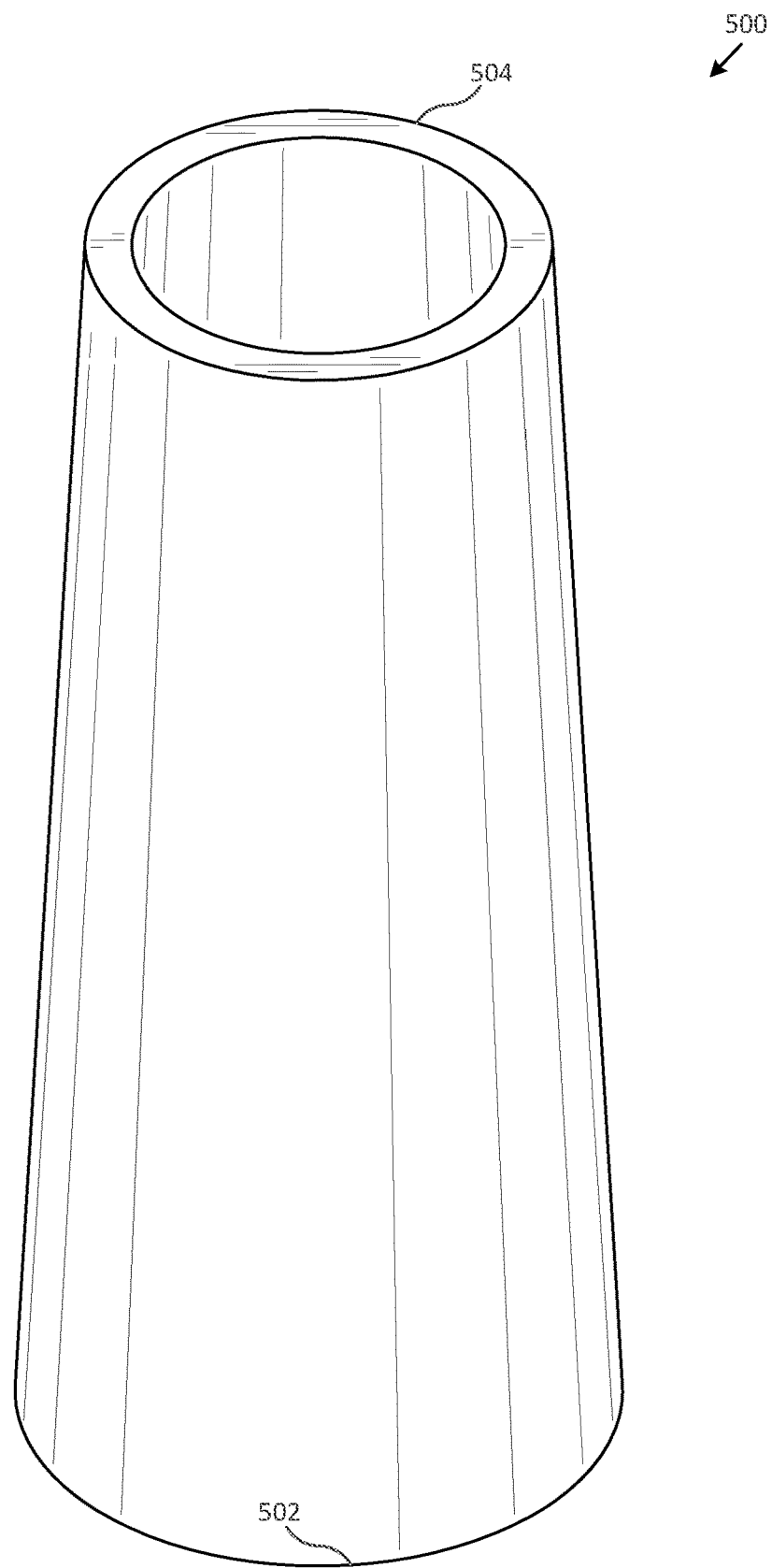
FIG. 5 (including FIGS. 5A-5G) illustrates an exemplary tapered stent, according to one embodiment of the present disclosure.
Figure 5B:
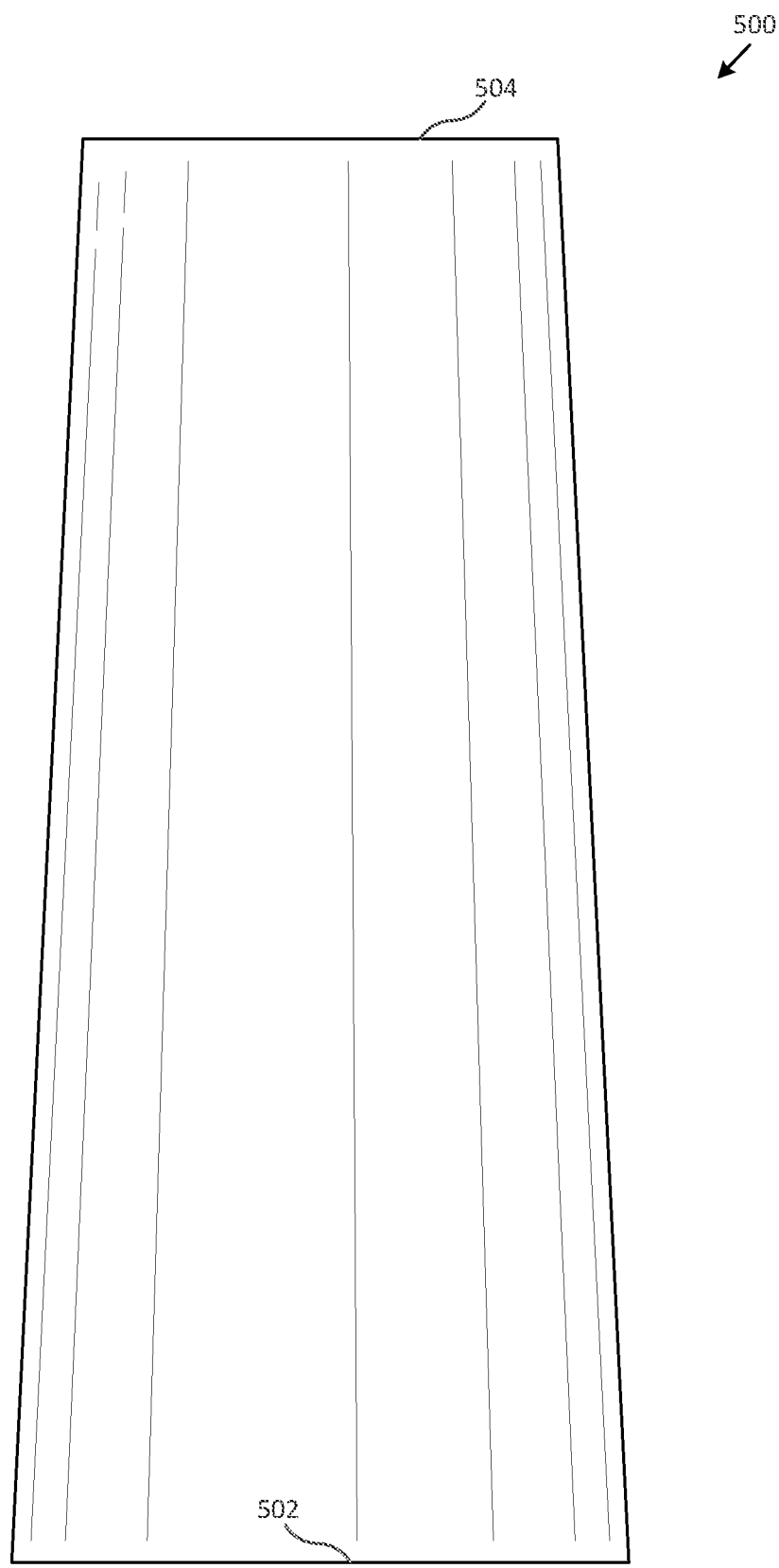
Figure 5C:
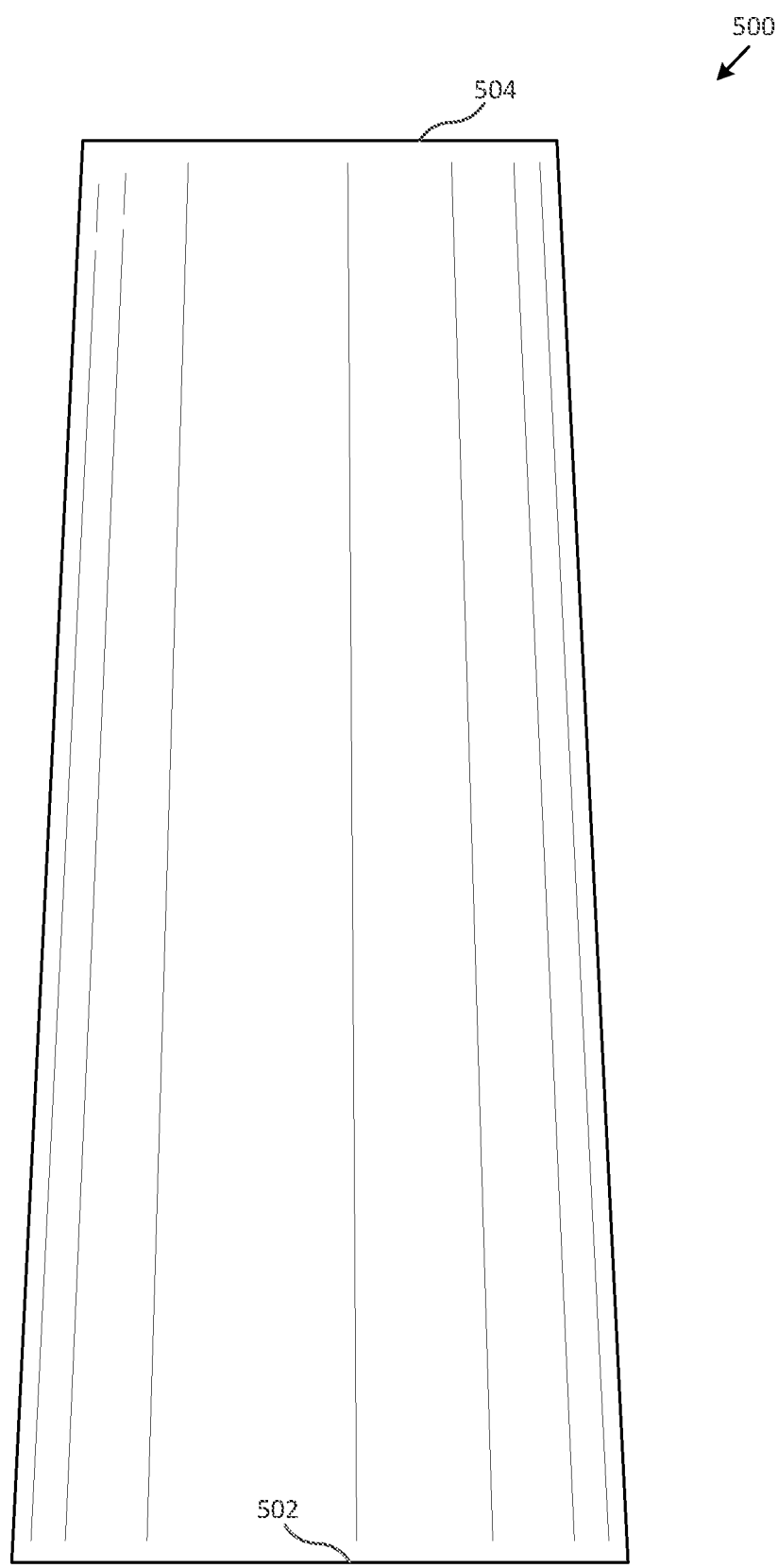
Figure 5D:
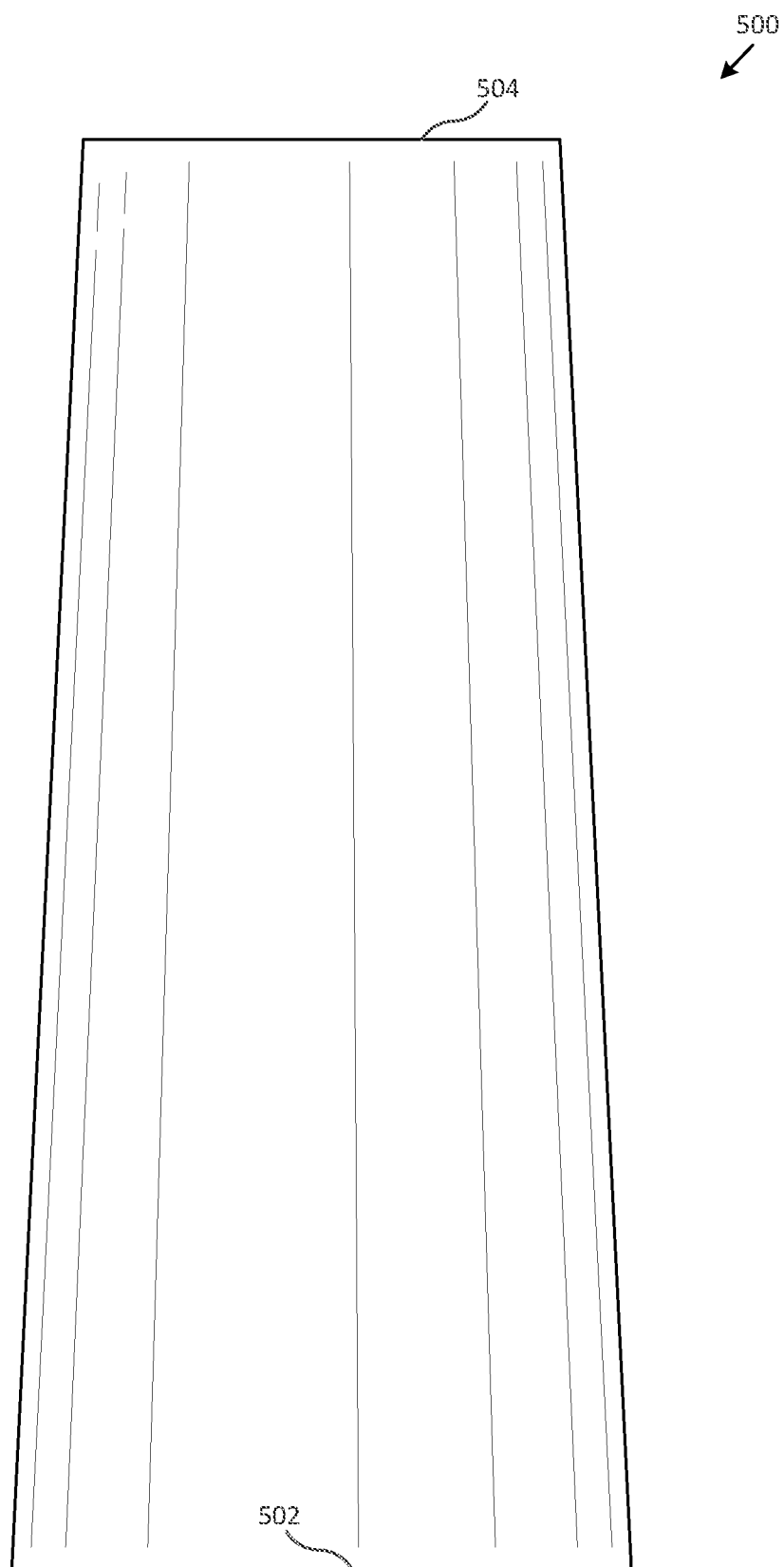
Figure 5E:
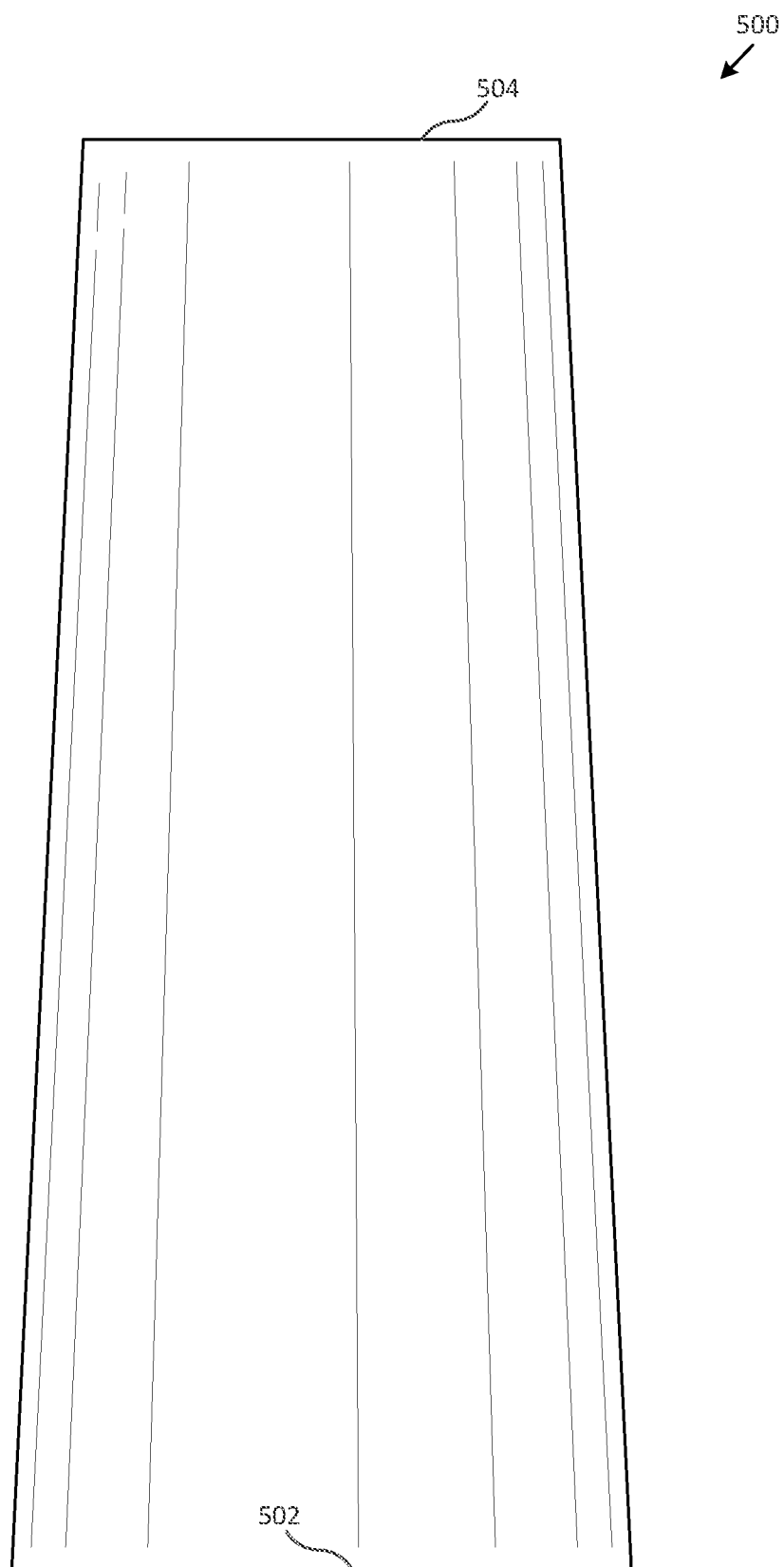
Figure 5F:
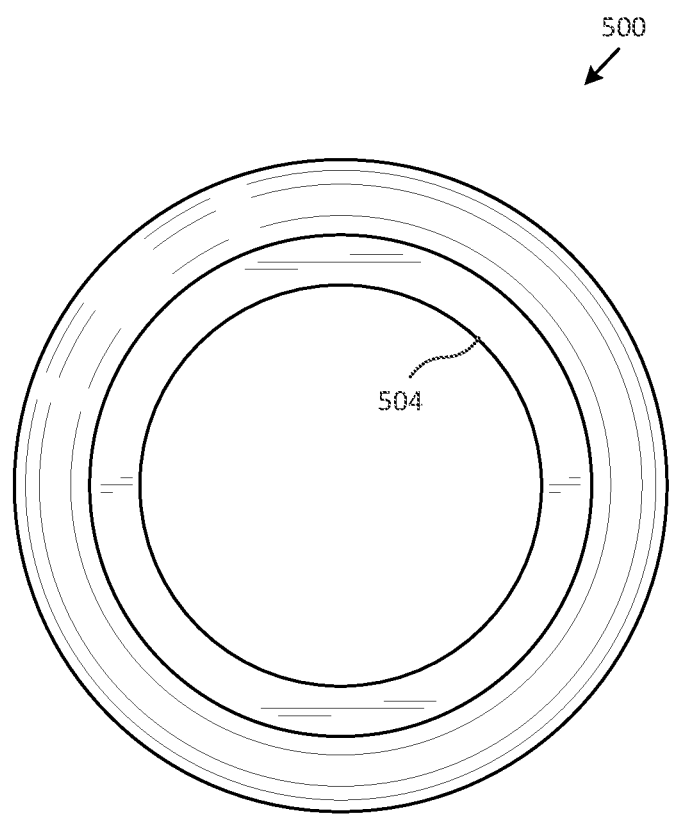
Figure 5G:
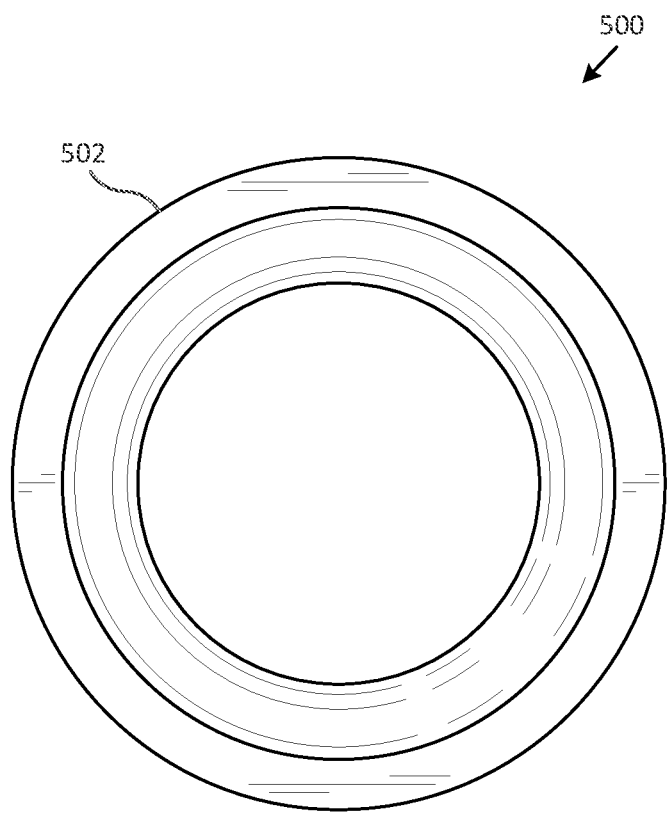

Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Furthermore, it should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems, methods, and apparatuses. In addition, some steps may be carried out simultaneously, contemporaneously, or in synchronization with other steps.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

In certain embodiments, the present systems and methods leverage fused deposition modeling ("FDM") and polycarbonate urethane ("PCU") to produce custom medical devices, including airway stents. FDM has traditionally been overlooked for medical device (and other complex devices/parts) applications because this process is somewhat limited on the complexity of shapes it can print. However, high-quality devices and parts can be FDM printed using techniques that leverage the novel methods described herein.

The present disclosure further relates to particular types of airway stents, including, but not limited to, accordion stents, cutout stents, spiral stents, studded stents, and tapered stents. As will be further discussed herein, each of these general stent configurations may be produced in a standard size (e.g., standard length) and/or may be produced based on a measurement and/or scan of a patient's airway. In at least one embodiment, the present disclosure related to airway stents that include multiple branches (e.g., substantially in a "Y" shape, substantially in a partial "V" shape, etc.). In some embodiments, the airway stents shown and described herein may be produced by the methods discussed herein (including FDM printing) or by other suitable processes.

The airway stents disclosed herein may include any suitable material, including polycarbonate urethane ("PCU"). PCU may provide a number of advantages for airway stents, including, but not limited to, a thinner wall thickness needed for an acceptable radial stiffness of the airway stent compared to other materials, including silicone. In one embodiment, a PCU airway stent created by an FDM printing method (such as those discussed herein) may require a thinner wall thickness compared to silicone stents. In at least one embodiment, PCU airway stents herein have a 0.75 mm wall thickness and a radial stiffness of 8-20 N/mm (measured at about 37 degrees Celsius), determined following the protocol of Ratnovsky et al. (discussed in Anat Ratnovsky et al., *Mechanical Properties of Different Airway Stents*, MED. ENG'G. PHYSICS, March 2011, at 408., available at http://www.medengphys.com/article/S1350-4533(15)00042-9/fulltext, incorporated herein by reference in its entirety), where the radial stiffness is calculated as the slope of the linear portion of the load-displacement curve following the initial ramp period. As will be understood, airway stents made of silicone may require a wall thickness of 1.0 mm to achieve approximately the same approximate radial stiffness (or radial stiffness range).

Previous research has been conducted in potentially related areas, as discussed in Andrew T. Miller et al., *Fatigue of Injection Molded and 3D Printed Polycarbonate Urethane in Solution*, 108 POLYMER 121 (2017), and Andrew T. Miller et al., *Deformation and Fatigue of Tough 3D Printed Elastomer Scaffolds Processed by Fused Deposition Modeling and Continuous Liquid Interface Production*, 75 J. MECHANICAL BEHAVIOR BIOMEDICAL MATERIALS 1 (2017), incorporated herein by reference in their entirety.

The airway stents (and/or medical devices, parts, etc.) discussed herein may be produced by any suitable means, including but not limited to, via FDM printing processes as will be further discussed herein.

Exemplary Medical Devices

Referring now to the figures, for the purposes of example and explanation of the fundamental processes and components of the disclosed systems and methods, reference is made to FIG. 1 (including FIGS. 1A-1G), which illustrates an exemplary accordion stent 100, according to one embodiment of the present disclosure. Generally, FIG. 1A includes a perspective view of the accordion stent 100, FIG. 1B includes a front view of the accordion stent 100, FIG. 1C includes a back view of the accordion stent 100, FIG. 1D includes a left side view of the accordion stent 100, FIG. 1E includes a right side view of the accordion stent 100, FIG. 1F includes a top view of the accordion stent 100, and FIG. 1G includes a bottom view of the accordion stent 100. In various embodiments, the accordion stent 100 is an airway stent that is placed against the interior surface of an airway (e.g., trachea, bronchi, etc.) to hold the airway open, permit the flow of fluids (e.g., air, oxygen, water, etc.) through the airway, etc.

In various embodiments, the accordion stent 100 is a hollow, generally-tubular shape that includes multiple protrusions 102 that are generally formed by pairs of abutting, juxtaposed frustums 104 (e.g., an inwardly-sloping frustum 104a and an outwardly-sloping frustum 104b, wherein the inward/outward perspective is determined from the central, longitudinal axis of the accordion stent 100, as would be 3D-printed from bottom to top—extending outward to form outwardly-sloping frustum 104b and then returning inward to form inwardly-sloping frustum 104a). Generally, the body of the accordion stent 100 includes a wall, with an exterior surface and an interior surface that extends between a top surface 106 and bottom surface (as will be understood, the top and bottom surface of a particular stent may be substantially the same in some embodiments). In various embodiments, the accordion stent 100 is custom-shaped such that it fits compatibly (e.g., perfectly, within a particular tolerance range, etc.) within the airway of a particular subject (e.g., human, animal, etc.). In one embodiment, the accordion stent 100 includes multiple tubular branches. The protrusions 102, in one embodiment, generally encompass the wall of the accordion stent 100 such that the accordion stent 100 is shaped like the extended bellows of an accordion.

The protrusions 102 generally are of a minimum diameter at the tops of the frustums 104 and a maximum diameter at the bottoms of the frustums 104. In one embodiment, the protrusions 102 are the same size and shape such that the accordion stent 100 is of roughly the same maximum and minimum exterior diameters throughout its length (e.g., the bases of the frustums 104 are of the same size and the tops of the frustums 104 are of the same size). In some embodiments, the protrusions 102 gradually increase in size and shape such that the accordion stent 100 increases in maximum and minimum exterior diameters along its length (e.g., the bases of the frustums 104 and the tops of the frustums 104 increase in diameter along the length of the accordion stent 100). In one or more embodiments, the protrusions 102 gradually decrease in size and shape such that the accordion stent 100 decreases in maximum and minimum exterior diameters along its length (e.g., the bases of the frustums 104 and the tops of the frustums 104 decrease in diameter along the length of the accordion stent 100). In one embodiment, the protrusions 102 vary in size and shape such that the accordion stent 100 varies in maximum and minimum exterior diameters along its length (e.g., the bases of the frustums 104 and the tops of the frustums 104 vary in diameter along the length of the accordion stent 100). The accordion stent 100, in various embodiments, may be between 6 mm and 24 mm in exterior diameter. In a particular embodiment, the accordion stent 100 may be between 9 mm and 20 mm in exterior diameter.

In one embodiment, the interior surface of the accordion stent 100 is of about the same diameter throughout the length of the accordion stent 100. In some embodiments, the interior surface of the accordion stent 100 is parallel to the exterior surface of the accordion stent 100 such that the diameter of the interior surface varies with the diameter of the protrusions 102. In one or more embodiments, the interior surface of the accordion stent 100 is not parallel to the exterior surface of the accordion stent 100 and the interior surface varies in diameter throughout the length of the accordion stent 100. The accordion stent 100, in various embodiments, may be between 2 mm and 23 mm in interior diameter.

Generally, the wall of the accordion stent 100 is of a thickness that is sufficient to withstand the pressure placed upon the exterior surface of the accordion stent 100 to keep it from collapsing (e.g., 0.5 mm, 1 mm, 1.5 mm, 2 mm, between 0.5-2 mm, etc.). In one embodiment, the accordion stent 100 is made from a bioinert material (e.g., polycarbonate-based thermoplastic polyurethane, polycarbonate urethane, polycarbonate urethane-silicone hybrids, Lubrizol® Carbothanes™ AC-4075A, AC-4085A, or AC-4095A; DSM® Bionate®, Bionate II®, or Carbosil®; AdvanSource® Chronoflex C®, Chronoflex AL®, Chronoflex AR®, Chronoflex AR-LT®, or Chronosil®, etc.). The accordion stent 100, in various embodiments, may be between 20 mm and 120 mm in length. In various embodiments, the wall of the accordion stent 100 is smooth and both the interior and exterior surfaces are seamless.

Now referring to FIG. 2 (including FIGS. 2A-2G), which illustrates an exemplary cutout stent 200, according to one embodiment of the present disclosure. Generally, FIG. 2A includes a perspective view of the cutout stent 200, FIG. 2B includes a front view of the cutout stent 200, FIG. 2C includes a back view of the cutout stent 200, FIG. 2D includes a left side view of the cutout stent 200, FIG. 2E includes a right side view of the cutout stent 200, FIG. 2F includes a top view of the cutout stent 200, and FIG. 2G includes a bottom view of the cutout stent 200. In various embodiments, the cutout stent 200 is an airway stent that is placed against the interior surface of an airway (e.g., trachea, bronchi, etc.) to hold the airway open, permit the flow of fluids (e.g., air, oxygen, water, etc.) through the airway, etc.

In various embodiments, the cutout stent 200 is a hollow, generally-tubular shape that includes multiple cutouts 202 and/or notches 204. Generally, the body of the cutout stent 200 includes a wall, with an exterior surface and an interior surface, that extends between a top surface 206 and a bottom surface. In various embodiments, the cutout stent 200 is custom-shaped such that it fits compatibly (e.g., perfectly, within a particular tolerance range, etc.) within the airway of a particular subject (e.g., human, animal, etc.). In one embodiment, the cutout stent 200 includes multiple tubular branches.

In various embodiments, cutouts 202 extend through the wall of the cutout stent 200, from the exterior surface through to the interior surface. In one embodiment, the cutouts 202 do not extend all the way through from the exterior surface to the interior surface. The cutouts 202, in various embodiments, may be diamond-shaped, circle-shaped, oval-shaped, etc. In various embodiments, the cutouts 202 may vary in size and shape throughout the length of the cutout stent 200. In some embodiments, the cutouts 202 may increase in size and shape throughout the length of the cutout stent 200. In one or more embodiments, the cutouts 202 may decrease in size and shape throughout the length of the cutout stent 200. In various embodiments, the cutouts 202 may be of the same size and shape throughout the length of the cutout stent 200. In some embodiments, the cutouts 202 may be uniformly spaced throughout the length of the cutout stent 200. In various embodiments, the cutouts 202 may be spaced randomly or at varying distances throughout the length of the cutout stent 200.

In one embodiment, the notches 204 extend downward from the top surface 206 and upwards from the bottom surface. In some embodiments, the notches 204 include partial cutouts 202 (e.g., half of a cutout 202, a quarter of a cutout 202, etc.). The notches 204, in various embodiments, may be triangle-shaped, rectangle-shaped, semi-circle-shaped, etc. In various embodiments, the notches 204 may vary in size and shape. In various embodiments, the notches 204 may be of the same size and shape. In one or more embodiments, the notches 204 may be of a different shape than the cutouts 202 (e.g., semi-circle-shaped notches 204 and diamond-shaped cutouts 202, etc.).

In one embodiment, the exterior surface of the cutout stent 200 is of the same diameter throughout the length of the cutout stent 200. In one or more embodiments, the exterior surface of the cutout stent 200 is of increasing diameter throughout the length of the cutout stent 200. In some embodiments, the exterior surface of the cutout stent 200 is of decreasing diameter throughout the length of the cutout stent 200. In one embodiment, the exterior surface of the cutout stent 200 is of varying diameter throughout the length of the cutout stent 200. The cutout stent 200, in various embodiments, may be between 6 mm and 24 mm in exterior diameter. In a particular embodiment, the cutout stent 200 may be between 9 mm and 20 mm in exterior diameter.

In one embodiment, the interior surface of the cutout stent 200 is of the same diameter throughout the length of the cutout stent 200. In one or more embodiments, the interior surface of the cutout stent 200 is parallel to the exterior surface of the cutout stent 200 such that the diameter of the interior surface varies with the diameter of the exterior surface. In some embodiments, the interior surface of the cutout stent 200 is not parallel to the exterior surface of the cutout stent 200 and the interior surface varies in diameter throughout the length of the cutout stent 200. The cutout stent 200, in various embodiments, may be between 2 mm and 23 mm in interior diameter.

Generally, the wall of the cutout stent 200 is of a thickness that is sufficient to withstand the pressure placed upon the exterior surface of the cutout stent 200 to keep it from collapsing (e.g., 0.5 mm, 1 mm, 1.5 mm, 2 mm, between 0.5-2 mm, etc.). In one embodiment, the cutout stent 200 includes a bioinert material (e.g., polycarbonate-based thermoplastic polyurethane, polycarbonate urethane, polycarbonate urethane-silicone hybrids, Lubrizol® Carbothanes™ AC-4075A, AC-4085A, or AC-4095A; DSM® Bionate®, Bionate II®, or Carbosil®; AdvanSource® Chronoflex C®, Chronoflex AL®, Chronoflex AR®, Chronoflex AR-LT®, or Chronosil®, etc.). The cutout stent 200, in various embodiments, may be between 20 mm and 120 mm in length. In various embodiments, the wall of the cutout stent 200 is smooth and both the interior and exterior surfaces are seamless.

Referring now to FIG. 3 (including FIGS. 3A-3G), which illustrates an exemplary spiral stent 300, according to one embodiment of the present disclosure. Generally, FIG. 3A includes a perspective view of the spiral stent 300, FIG. 3B includes a front view of the spiral stent 300, FIG. 3C includes a back view of the spiral stent 300, FIG. 3D includes a left side view of the spiral stent 300, FIG. 3E includes a right side view of the spiral stent 300, FIG. 3F includes a top view of the spiral stent 300, and FIG. 3G includes a bottom view of the spiral stent 300. In various embodiments, the spiral stent 300 is an airway stent that is placed against the interior surface of an airway (e.g., trachea, bronchi, etc.) to hold the airway open, permit the flow of fluids (e.g., air, oxygen, water, etc.) through the airway, etc.

In various embodiments, the spiral stent 300 is a hollow, generally-tubular shape that includes multiple protrusions 302 that are generally formed by helical ridges. Generally, the body of the spiral stent 300 includes a wall, with an exterior surface and an interior surface, that extends between a top surface 304 and a bottom surface. In various embodiments, the spiral stent 300 is custom-shaped such that it fits compatibly (e.g., perfectly, within a particular tolerance range, etc.) within the airway of a particular subject (e.g., human, animal, etc.). In one embodiment, the spiral stent 300 includes multiple tubular branches. The protrusions 302, in one embodiment, generally encompass the wall of the spiral stent 300 such that the spiral stent 300 is a single, continuous helical ridge.

The protrusions 302 generally are of a minimum diameter at the bottom of the ridge and a maximum diameter at the top of the ridge. In one embodiment, the protrusions 302 are the same size and shape such that the spiral stent 300 is of roughly the same maximum and minimum exterior diameters throughout its length (e.g., the ridges are of the same size and shape). In one or more embodiments, the protrusions 302 gradually increase in size and shape such that the spiral stent 300 increases in maximum and minimum exterior diameters along its length (e.g., the ridges are of increasing size and shape). In some embodiments, the protrusions 302 gradually decrease in size and shape such that the spiral stent 300 decreases in maximum and minimum exterior diameters along its length (e.g., the ridges are of decreasing size and shape). In one embodiment, the protrusions 302 vary in size and shape such that the spiral stent 300 varies in maximum and minimum exterior diameters along its length (e.g., the ridges are of varying size and shape). The spiral stent 300, in various embodiments, may be between 6 mm and 24 mm in exterior diameter. In a particular embodiment, the spiral stent 300 may be between 9 mm and 20 mm in exterior diameter.

In one embodiment, the interior surface of the spiral stent 300 is of substantially the same diameters throughout the length of the spiral stent 300. In some embodiments, the interior surface of the spiral stent 300 is parallel to the exterior surface of the spiral stent 300 such that the diameter of the interior surface varies with the diameter of the protrusions 302. In one embodiment, the interior surface of the spiral stent 300 is not parallel to the exterior surface of the spiral stent 300 and the interior surface varies in diameter throughout the length of the spiral stent 300. The spiral stent 300, in various embodiments, may be between 2 mm and 23 mm in interior diameter.

Generally, the wall of the spiral stent 300 is of a thickness that is sufficient to withstand the pressure placed upon the exterior surface of the spiral stent 300 to keep it from collapsing (e.g., 0.5 mm, 1 mm, 1.5 mm, 2 mm, between 0.5-2 mm, etc.). In one embodiment, the spiral stent 300 is made of a bioinert material (e.g., polycarbonate-based thermoplastic polyurethane, polycarbonate urethane, polycarbonate urethane-silicone hybrids, Lubrizol® Carbothanes™ AC-4075A, AC-4085A, or AC-4095A; DSM® Bionate®, Bionate II®, or Carbosil®; AdvanSource® Chronoflex C®, Chronoflex AL®, Chronoflex AR®, Chronoflex AR-LT®, or Chronosil®, etc.). The spiral stent 300, in various embodiments, may be between 20 mm and 120 mm in length. In various embodiments, the wall of the spiral stent 300 is smooth and both the interior and exterior surfaces are seamless.

Now referring to FIG. 4 (including FIGS. 4A-4G), which illustrates an exemplary studded stent 400, according to one embodiment of the present disclosure. Generally, FIG. 4A includes a perspective view of the studded stent 400, FIG. 4B includes a front view of the studded stent 400, FIG. 4C includes a back view of the studded stent 400, FIG. 4D includes a left side view of the studded stent 400, FIG. 4E includes a right side view of the studded stent 400, FIG. 4F includes a top view of the studded stent 400, and FIG. 4G includes a bottom view of the studded stent 400. In various embodiments, the studded stent 400 is an airway stent that is placed against the interior surface of an airway (e.g., trachea, bronchi, etc.) to hold the airway open, permit the flow of fluids (e.g., air, oxygen, water, etc.) through the airway, etc.

In various embodiments, the studded stent 400 is a hollow, generally-tubular shape that includes multiple studs 402, with sloping surfaces 404a and flat surfaces 404b. Generally, the body of the studded stent 400 includes a wall, with an exterior surface and an interior surface that extends between a top surface 406 and a bottom surface. In various embodiments, the studded stent 400 is custom-shaped such that it fits compatibly (e.g., perfectly, within a particular tolerance range, etc.) within the airway of a particular subject (e.g., human, animal, etc.). In one embodiment, the studded stent 400 includes multiple tubular branches.

In various embodiments, studs 402 include a sloping surface 404a that extends away from the exterior surface at an acute angle and a flat surface 404b that is substantially parallel to the exterior surface. In one embodiment, the studs 402 are hollow. In some embodiments, the studs 402 are solid. The studs 402, in various embodiments, may be frustum-shaped, circle-shaped, oval-shaped, etc. The flat surface 404b may be circle-shaped, oval-shaped, etc. In various embodiments, the studs 402 may vary in size and shape throughout the length of the studded stent 400. In one or more embodiments, the studs 402 may increase in size and shape throughout the length of the studded stent 400. In various embodiments, the studs 402 may decrease in size and shape throughout the length of the studded stent 400. In various embodiments, the studs 402 may be of the same size and shape throughout the length of the studded stent 400. In one embodiment, the studs 402 are uniformly spaced throughout the length of the studded stent 400. In various embodiments, the studs 402 may be spaced randomly or at varying distances throughout the length of the studded stent 400.

In one embodiment, the exterior surface of the studded stent 400 is of the same diameter throughout the length of the studded stent 400. In one or more embodiments, the exterior surface of the studded stent 400 is of increasing diameter throughout the length of the studded stent 400. In some embodiments, the exterior surface of the studded stent 400 is of decreasing diameter throughout the length of the studded stent 400. In one embodiment, the exterior surface of the studded stent 400 is of varying diameter throughout the length of the studded stent 400. The studded stent 400, in various embodiments, may be between 6 mm and 24 mm in exterior diameter. In a particular embodiment, the studded stent 400 may be between 9 mm and 20 mm in exterior diameter.

In one embodiment, the interior surface of the studded stent 400 is of the same diameter throughout the length of the studded stent 400. In one or more embodiments, the interior surface of the studded stent 400 is parallel to the exterior surface of the studded stent 400 such that the diameter of the interior surface varies with the diameter of the exterior surface. In some embodiments, the interior surface of the studded stent 400 is not parallel to the exterior surface of the studded stent 400 and the interior surface varies in diameter throughout the length of the studded stent 400. The studded stent 400, in various embodiments, may be between 2 mm and 23 mm in interior diameter.

Generally, the wall of the studded stent 400 is of a thickness that is sufficient to withstand the pressure placed upon the exterior surface of the studded stent 400 to keep it from collapsing (e.g., 0.5 mm, 1 mm, 1.5 mm, 2 mm, between 0.5-2 mm, etc.). In one embodiment, the studded stent 400 is made of a bioinert material (e.g., polycarbonate-based thermoplastic polyurethane, polycarbonate urethane, polycarbonate urethane-silicone hybrids, Lubrizol® Carbothanes™ AC-4075A, AC-4085A, or AC-4095A; DSM® Bionate®, Bionate II®, or Carbosil®; AdvanSource® Chronoflex C®, Chronoflex AL®, Chronoflex AR®, Chronoflex AR-LT®, or Chronosil®, etc.). The studded stent 400, in various embodiments, may be between 20 mm and 120 mm in length. In various embodiments, the wall of the studded stent 400 is smooth and both the interior and exterior surfaces are seamless.

Referring now to FIG. 5 (including FIGS. 5A-5G), which illustrates an exemplary tapered stent 500, according to one embodiment of the present disclosure. Generally, FIG. 5A includes a perspective view of the tapered stent 500, FIG. 5B includes a front view of the tapered stent 500, FIG. 5C includes a back view of the tapered stent 500, FIG. 5D includes a left side view of the tapered stent 500, FIG. 5E includes a right side view of the tapered stent 500, FIG. 5F includes a top view of the tapered stent 500, and FIG. 5G includes a bottom view of the tapered stent 500. In various embodiments, the tapered stent 500 is an airway stent that is placed against the interior surface of an airway (e.g., trachea, bronchi, etc.) to hold the airway open, permit the flow of fluids (e.g., air, oxygen, water, etc.) through the airway, etc.

In various embodiments, the tapered stent 500 is a hollow, generally-tubular shape. Generally, the body of the tapered stent 500 includes a wall, with an exterior surface and an interior surface, that extends between a bottom surface 502 and a top surface 504. In some embodiments, the tapered stent 500 is custom-shaped such that it fits compatibly (e.g., perfectly, within a particular tolerance range, etc.) within the airway of a particular subject (e.g., human, animal, etc.). In one embodiment, the tapered stent 500 includes multiple tubular branches. In various embodiments, the wall of the tapered stent 500 is smooth and both the interior and exterior surfaces are seamless.

In one embodiment, the exterior surface of the tapered stent 500 is of the same diameter throughout the length of the tapered stent 500 (e.g., from the bottom surface 502 to the top surface 504). In one or more embodiments, the exterior surface of the tapered stent 500 is of increasing diameter throughout the length of the tapered stent 500 (e.g., with larger diameter at the bottom surface 502 than at the top surface 504). In some embodiments, the exterior surface of the tapered stent 500 is of decreasing diameter throughout the length of the tapered stent 500 (e.g., with smaller diameter at the bottom surface 502 than at the top surface 504). In one embodiment, the exterior surface of the tapered stent 500 is of varying diameter throughout the length of the tapered stent 500. The tapered stent 500, in various embodiments, may be between 6 mm and 24 mm in exterior diameter. In a particular embodiment, the tapered stent 500 may be between 9 mm and 20 mm in exterior diameter.

In one embodiment, the interior surface of the tapered stent 500 is of the same diameter throughout the length of the tapered stent 500. In one or more embodiments, the interior surface of the tapered stent 500 is parallel to the exterior surface of the tapered stent 500 such that the diameter of the interior surface varies with the diameter of the external surface. In some embodiments, the interior surface of the tapered stent 500 is not parallel to the exterior surface of the tapered stent 500 and the interior surface varies in diameter throughout the length of the tapered stent 500. The tapered stent 500, in various embodiments, may be between 2 mm and 23 mm in interior diameter.

Generally, the wall of the tapered stent 500 is of a thickness that is sufficient to withstand the pressure placed upon the exterior surface of the tapered stent 500 to keep it from collapsing (e.g., 0.5 mm, 1 mm, 1.5 mm, 2 mm, between 0.5-2 mm, etc.). In one embodiment, the tapered stent 500 is made of a bioinert material (e.g., polycarbonate-based thermoplastic polyurethane, polycarbonate urethane, polycarbonate urethane-silicone hybrids, Lubrizol® Carbothanes™ AC-4075A, AC-4085A, or AC-4095A; DSM® Bionate®, Bionate II®, or Carbosil®; AdvanSource® Chronoflex C®, Chronoflex AL®, Chronoflex AR®, Chronoflex AR-LT®, or Chronosil®, etc.). The tapered stent 500, in various embodiments, may be between 20 mm and 120 mm in length.

Exemplary Environment

Figure 6:
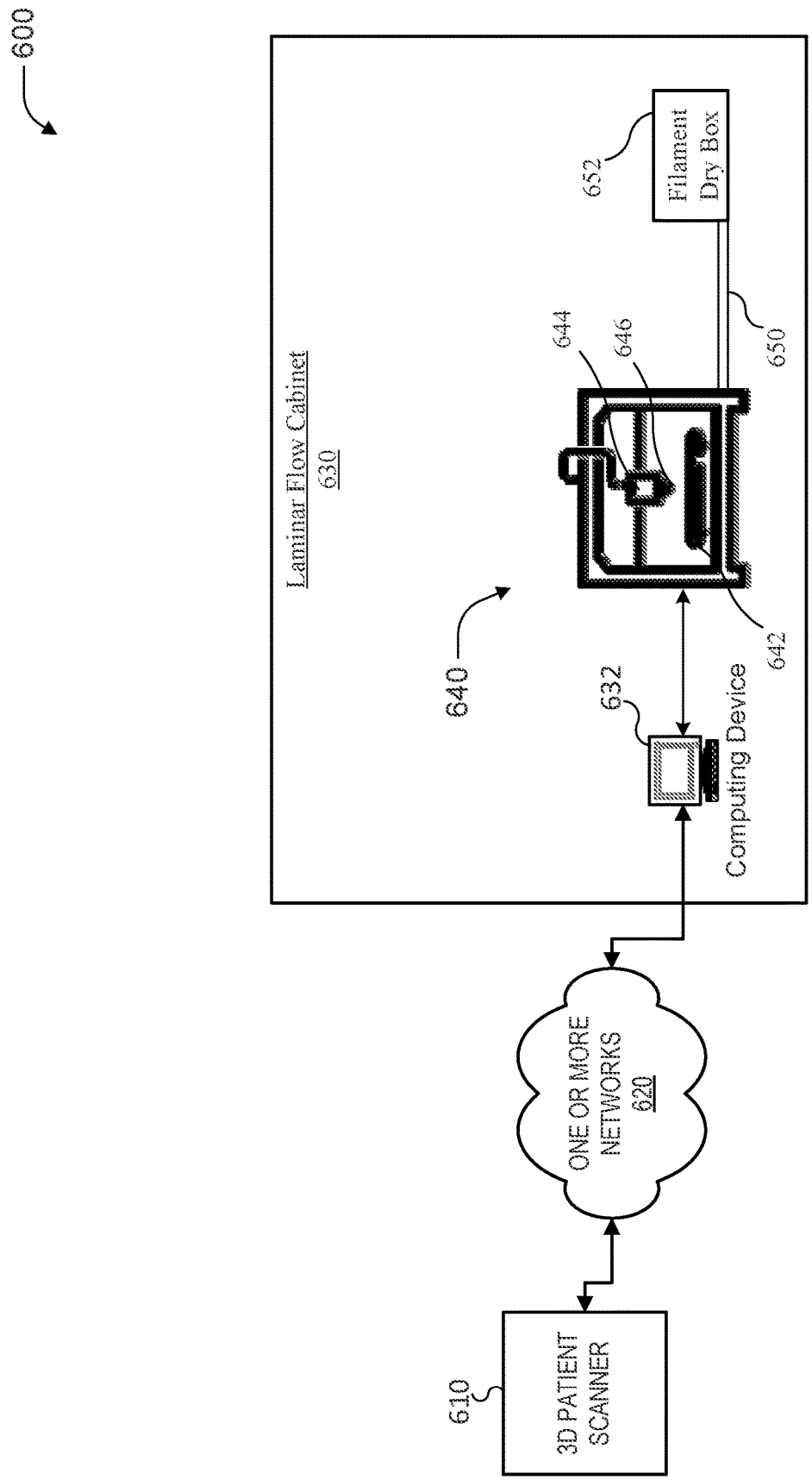
FIG. 6 shows an exemplary medical device 3D-printing environment according to one embodiment of the present disclosure.

Turning now to FIG. 6, an exemplary system environment 600 is shown according to one embodiment of the present disclosure. In the embodiment shown in FIG. 6, the system includes a 3D patient scanner 610 operatively connected to a computing device 632 via one or more networks 620. As shown in the embodiment of FIG. 6, the system further includes a laminar flow cabinet 630 housing the computing device 632 operatively connected to a 3D printer 640, which is connected to a dry filament box 652 by tubing 650.

As discussed herein, the present systems and methods create medical devices for implantation within a patient. In some embodiments, the system takes or receives a scan of a portion of the patient via 3D patient scanner 610 to create a medical device that is customized to the patient (e.g., in some embodiments, the system takes or receives a scan of a patient's airway and then creates an airway stent that is based on the dimensions of the patient's actual airway). An exemplary process of creating a customized medical device for a particular patient is further discussed below in relation to FIG. 7. In further embodiments, the system may utilize a standard medical device geometry for creating a medical device for a particular patient (e.g., the medical device is not based on dimensions of the actual patient, but is instead based on a standard geometry, which may be based on, for example, a height and weight of the particular patient).

The components of the exemplary system shown in FIG. 6 may be arranged in the same or different locations. In particular embodiments, the 3D patient scanner 610 and components shown enclosed in the laminar flow cabinet 630 may be geographically arranged in the same location (e.g., a hospital, clinic, or the like). In these embodiments (and others), the one or more networks 620 may represent a local network (e.g., a local WiFi network) or a hard-wired system (e.g., the 3D patient scanner is hard-wired to the computing device 632). According to further embodiments, the 3D patient scanner 610 and other components may be arranged in geographically different locations (e.g., the 3D patient scanner 610 is located a clinic where a patient's airway is scanned and the 3D printer 640 and/or other components are located in a separate manufacturing facility).

Returning to FIG. 6, the exemplary system includes a laminar flow cabinet 630 for preventing contamination of medical devices (or other devices) produced by the 3D printer 640 and/or other equipment stored within. In some embodiments, the laminar flow cabinet 630 takes in air from the surrounding room, filters it, and passes it through the cabinet to keep a positive pressure inside the cabinet which prevents debris and dust from entering, thereby preventing contamination of the medical devices produced by the 3D printer 640 by debris, dust, and other particulates. In further embodiments, the laminar flow cabinet includes a UV light bulb for sterilizing the interior of the laminar flow cabinet. According to particular embodiments, the laminar flow cabinet 630 may be an Air Science® Purair® Cabinet Model VLF-72-SS or other suitable laminar flow cabinet.

In embodiment shown in FIG. 6, the laminar flow cabinet 630 encloses the 3D printer 640. According to particular embodiments, the 3D printer 640 includes a print bed 642, a print head 644, and nozzle 646, among other components. As discussed herein, in various embodiments, the systems and methods herein are related to fused deposition modeling ("FDM"). FDM includes feeding a filament into a heated nozzle (e.g., nozzle 646) and creating a device (or part) by tracing a profile of the device or part on a surface (e.g., print bed 642). One type of printer that may be suitable for the system and methods herein, as a non-limiting example is a Lulzbot® TAZ 6 Model FDM printer. This printer, in particular embodiments, leverages new and customized parts and processes to create medical-device quality devices/parts.

In various embodiments, to maintain quality of devices produced by the 3D printer 640, a custom print bed 642 is used. In particular embodiments, the print bed 642 is a non-stick print surface (to help keep portions of the printed device/part from sticking to the print surface and reducing quality control issues and post-printing work on the device/part). A non-limiting example of a non-stick print bed is a 3D Universe Lokbuild™ print surface. In some embodiments, the system is configured to heat the print bed 642 as further discussed below (also to help keep portions of the printed device/part from sticking to the print bed and reducing quality control issues and post-printing work on the device/part).

In the embodiment shown in FIG. 6, the 3D printer 640 includes the print head 644. In particular embodiments, the print head 644 is designed for flexible materials. As a non-limiting example, a suitable print head 644 may be a Lulzbot® Flexystruder V2 model print head.

As will be understood from discussions herein, the 3D printer 640 may include a gear that feeds filament through the print head 644 to the print nozzle 646. In at least one embodiment, the distance between the gear that feeds the filament into the print nozzle 646 is minimized to avoid buckling of the filament (e.g., because the filament is flexible). In some embodiments, the distance between the gear and the print nozzle 644 is about 60.0 mm to 90.0 mm.

In particular embodiments, the space between the gear that feeds the filament into the print nozzle 646 and the print nozzle 646 contains a tubing to support the filament. In various embodiments, the inner diameter of this tubing is slightly larger than the diameter of the filament.

According to various embodiments, the 3D printer 640 includes the print nozzle 646, which may include any suitable output diameter. In some embodiments, the print nozzle 646 includes an output diameter of between 0.2 and 1.2 mm. In particular embodiments, the print nozzle 646 includes an output diameter of between 0.3 to 0.6 mm. As a non-limiting example, the print nozzle 646 is a Mirco Swiss brand plated nozzle.

As discussed above, in particular embodiments, the 3D printer 640 is fed material for printing. In the embodiment shown in FIG. 6, filament (or other print material) is stored in a filament dry box 652 and is fed to the 3D printer 640 via the tubing 650. As mentioned herein, the system may be configured to print thermoplastics, including polycarbonate urethane ("PCU"). PCU (and other materials) may collect moisture from the ambient air and such moisture may affect part quality (e.g., printing the material with absorbed moisture may result in the 3D printer turning the absorbed moisture to steam in the printer nozzle, which may produce small bubbles in the melted material coming out of the nozzle, which can adversely affect part quality). As such, in particular embodiments, the system includes a dry box (e.g., filament dry box 652) and tubing 650 to prevent the print material from collecting moisture from the ambient air. In further embodiments, the systems and/or methods herein may include drying the print material (e.g., via a vacuum oven or the like) prior to printing/creating a device or part.

Returning to the embodiment shown in FIG. 6, the system includes the filament dry box 652. The filament dry box 652, in particular embodiments, includes an outer case (e.g., Pelican™ Case Model 1430) with a hole in the side for connecting the tubing 650. The filament dry box 652, in various embodiments, includes a humidity monitor (e.g., AcuRite® 01083), a desiccant (e.g., Eva-Dry® E-333; to keep humidity levels down inside the dry filament box) and components for holding and dispensing printing material within the dry filament box 652. In some embodiments, the filament dry box 652 may include fittings to suspend a spool of filament within and allow free rotation of the spool, such as for example, a length of plastic (e.g., PVC) pipe, a mechanism for suspending the pipe (e.g., two shower curtain rod holders), and an adhesive for attaching the suspending mechanism to side walls of the filament dry box 652 (e.g., two 3M® Command™ Strips).

As further discussed herein, the system, in certain embodiments, may include a vacuum oven. In one or more embodiments, the vacuum oven is located within the laminar flow cabinet. In some embodiments, the vacuum oven is located outside the laminar flow cabinet (or at a different facility, location, or the like).

In various embodiments, the filament is dried in the vacuum oven prior to use/printing (in lieu of, or addition to, the filament being stored in the filament dry box 652). According to particular embodiments, a portion of filament (e.g., a portion to be printed and/or an entire spool of filament) is dried in the vacuum oven for about 30 minutes at 100 degrees Celsius and at a vacuum pressure of about −20 inHg. According to further embodiments, the portion of filament may be dried for any length of time (e.g., 5 minutes, 10, minutes, 60 minutes, etc.) at any suitable temperature (e.g., 50 degrees Celsius, 75 degrees Celsius, 125 degrees Celsius, etc.) and at any suitable pressure for drying the portion of filament (e.g., removing substantially all moisture from the portion of filament).

In particular embodiments, the system includes tubing 650 and related components for keeping the printing material dry as the printing material is fed from the filament dry box 652 to the 3D printer 640. In one embodiment, the tubing 650 includes tubing that is about 3/16 inches outer diameter and 1/8 inches inner diameter and made of Teflon, although any tubing of a suitable size and material may be used. In various embodiments, the system includes one or more plumbing fittings including push-to-connect tube fittings, O-rings, and an end cap, for connecting the tubing 650 to the filament dry box 652 and to provide an airtight seal. In one or more embodiments, the system includes a removable end cap on the end of the tubing 650 for accessing the material for feeding into the 3D printer 640.

As discussed herein, in particular embodiments, the exemplary components described above are used with certain methods for producing medical devices and/or other parts. These exemplary processes are further described below in relation to FIGS. 7-11.

Exemplary Processes

The present disclosure is related to various methods of producing medical devices and/or other parts or devices. The present disclosure is related to particular methods for creating a custom file used for printing a medical device (or other part) that is specific to a particular patient (or other dimension-varying item), as discussed in FIG. 7. The present disclosure is also related to creating a medical device via particular 3D printing processes shown in FIGS. 8-9 (in some embodiments, the processes discussed in FIGS. 8-9 leverage the custom file created via the process shown in FIG. 7. FIGS. 10-11 depict the movement of an exemplary 3D printer when following the process discussed in FIG. 9 (and/or other process(es)).

Figure 7:
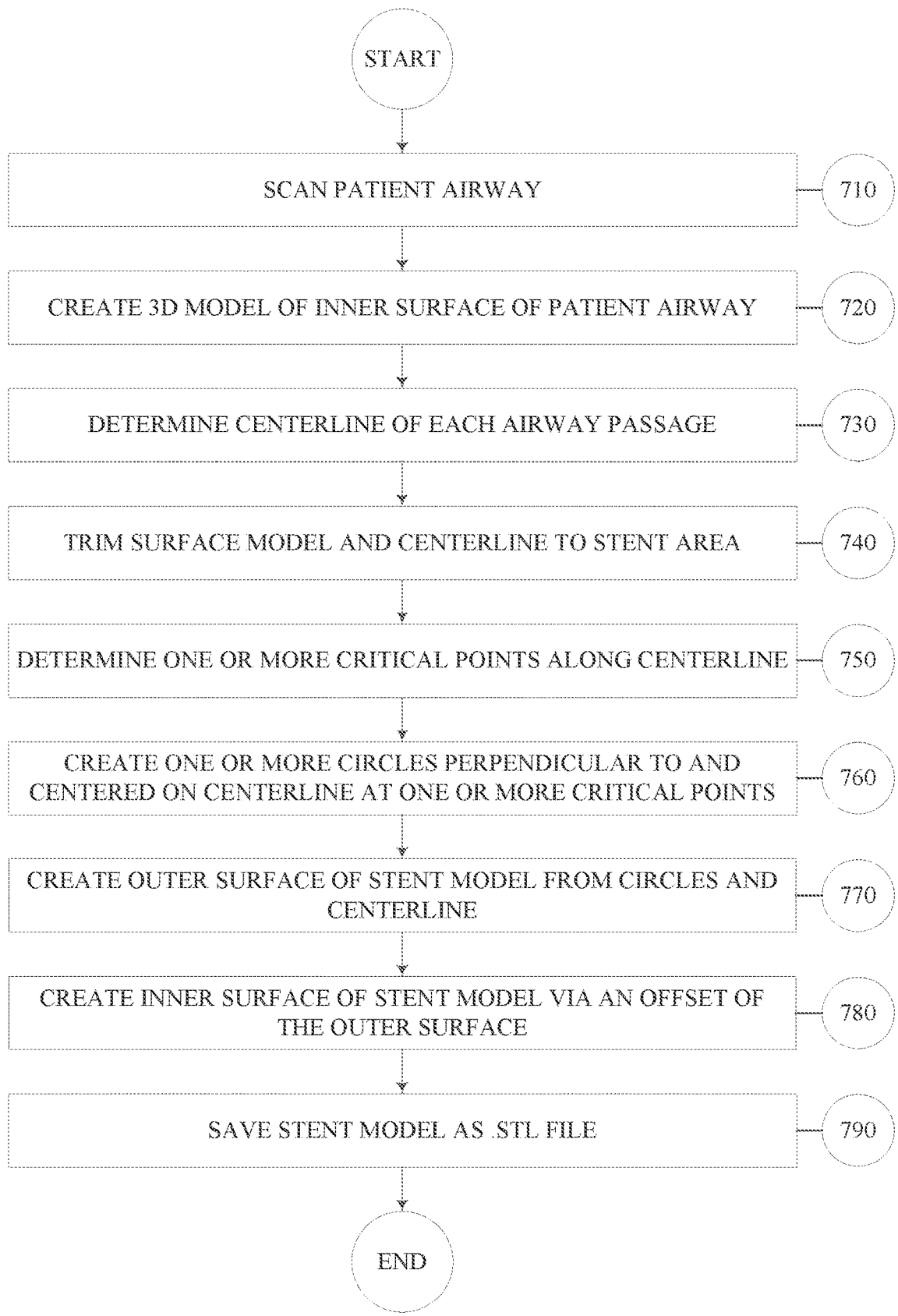
FIG. 7 is a flowchart of an exemplary 3D model creation process according to one embodiment of the present disclosure.

Turning now to FIG. 7, the exemplary process begins with scanning a patient airway with an airway scanning device (e.g. CT scan, MM, etc.) at step 710. The scan may be performed automatically by the system or manually through a separate device operated by a surgeon (or other qualified medical practitioner). In at least one embodiment, the airway scanning device is operatively connected to a computing device operatively connected to a 3D printer (as shown in FIG. 6). In some embodiments, the airway scanning device is not connected to the 3D printer and the file, including the scan of the patient's airway, may be received by the system via the Internet or another suitable mechanism.

In particular embodiments, the system is configured to receive the scan of the patient airway (e.g., from step 710) and create a 3D model of an inner surface of the patient airway at step 720. The system may be configured to receive the scan of the patient airway in any suitable way, including, but not limited to via email, through a direct connection between the scanning device and a computing device (e.g., computing device 632 shown in FIG. 6), via an automatic (or substantially automatic) download from a website (e.g., an FTP site), via an encrypted portal, etc.

As will be understood, the scan of the patient's airway may include a multitude of information, including, but not limited to, an inner surface of the patient's airway. In some embodiments, the system detects, isolates, and creates a 3D model of an inner surface of the patient's airway, which may include the patient's trachea, bronchi and smaller branches.

In various embodiments, the system creates the 3D model of a patient airway by calculating the inner-most points in a plane (or planes) and isolating these points. In some embodiments, the 3D model includes an indication of the inner surface of the patient's airway (e.g., different areas of the scan are "tagged") and the system is configured to isolate the inner surface based on the indication included with the 3D model.

At step 730, the system is configured to determine a centerline of each airway passage. In various embodiments, the system determines the centerline of the airway passage by determining a midpoint of a distance between each opposite point on the inner surface of the 3D model of the patient airway and by connecting the midpoints. According to particular embodiments, the system determines the centerline of the airway passage by slicing the airway passage into planes and finding a center point of each plane and then connecting each center point. In further embodiments, the system determines the centerline of the each airway passage by slicing the airway passage into one or more planes, connecting each opposing point on each plane, and determining an intersection point of each connection between opposing points. In still further embodiments, the system determines the centerline of each airway passage by another suitable calculation/mechanism.

At step 740, the system is configured to trim the surface model and the centerline to a particular stent area. As will be understood, the stent may be used in a surgical procedure to treat one or more indications of a particular patient and the length of the stent may not need to be the entire length of the patient's airway. In various embodiments, the system is configured to trim the surface model and the centerline to a standard stent size. In particular embodiments, the system is configured to trim the surface model to a customized stent size as determined by the procedure/indication (e.g., certain indications may call for standard stent sizes based on the dimensions of the patient and/or other factors). In some embodiments, the system is configured to trim the surface model and the centerline to a stent size that is based on input (e.g., a surgeon or other operator inputs the stent area). In further embodiments, as will be understood from discussions herein, the stent may include one or more branches and each branch of the stent may be trimmed to different lengths (or the same length).

At step 750, the system is configured to determine one or more critical points along the centerline. In various embodiments, the one or more critical points are points along the centerline where the centerline changes direction, bends, is an end point of the (trimmed) centerline, a diameter change of the airway stent, or another suitable point. As will be understood, the system is configured to determine the one or more critical points in any suitable way, including, but not limited to, by determining that points of the centerline do not lie in the same plane (e.g., there is a bend or change in direction in the centerline), or via selection by a user.

At step 760, the system is configured to create one or more substantially circular shapes (or other suitable shape, such as oval, elliptical, etc.) perpendicular to and centered on the centerline at each of the one or more critical points. In various embodiments, the diameter of the one or more substantially circular shapes is substantially similar to the inner diameter of the patient's airway (e.g., of the 3D model of the inner surface of the patient's airway). In particular embodiments, the diameter of the one or more substantially circular shapes is either oversized or undersized to account for various factors, including, but not limited to, patient specific factors (e.g., in one embodiment, the diameter of the one or more substantially circular shapes may be oversized if the patient's airway is especially weak to produce a tight fit). In at least one embodiment, the circular shape is created from a measurement of the inner perimeter of the airway at the location of the shape (e.g., in some cases, a patient's airway may be compressed by tumor and the area of the airway may appear different on a CT scan, but the perimeter of the same may remain the same).

At step 770, the system is configured to create an outer surface of the stent model from the one or more substantially circular shapes and the centerline. In various embodiments, the system is configured to create the outer surface of the stent model by connecting the outer edge of each of the one or more substantially circular shapes (centered along the centerline), thereby creating a surface of the stent model that changes directions, bends, changes diameter, etc. at each of the critical points.

At step 780, the system is configured to create an inner surface of the stent model via an offset of the outer surface (e.g., created at step 770). In various embodiments, the system is configured to create the inner surface of the stent model by offsetting the outer surface of the stent model a predetermined distance (which may be a standard or customizable distance). In some embodiments, the offset is between approximately 0.5 and 1 mm (e.g., approximately 0.0.8 mm, etc.). As will be understood, the offset may be uniform or include variations (e.g., for different diameters along the airway). As will also be understood, the offset distance represents a thickness of the stent once created.

At step 790, the system is configured to save the stent model as a 3D printable file (e.g., a .STL file), which may then be used to print or otherwise produce the stent. As will be understood, other suitable files and file types may be used and a .STL file is merely exemplary. Further, in some embodiments, the stent model may be sent directly to a computing system and/or printer, which may then print or otherwise create the stent (e.g., with or without saving the stent model as a particular file type).

Figure 8:
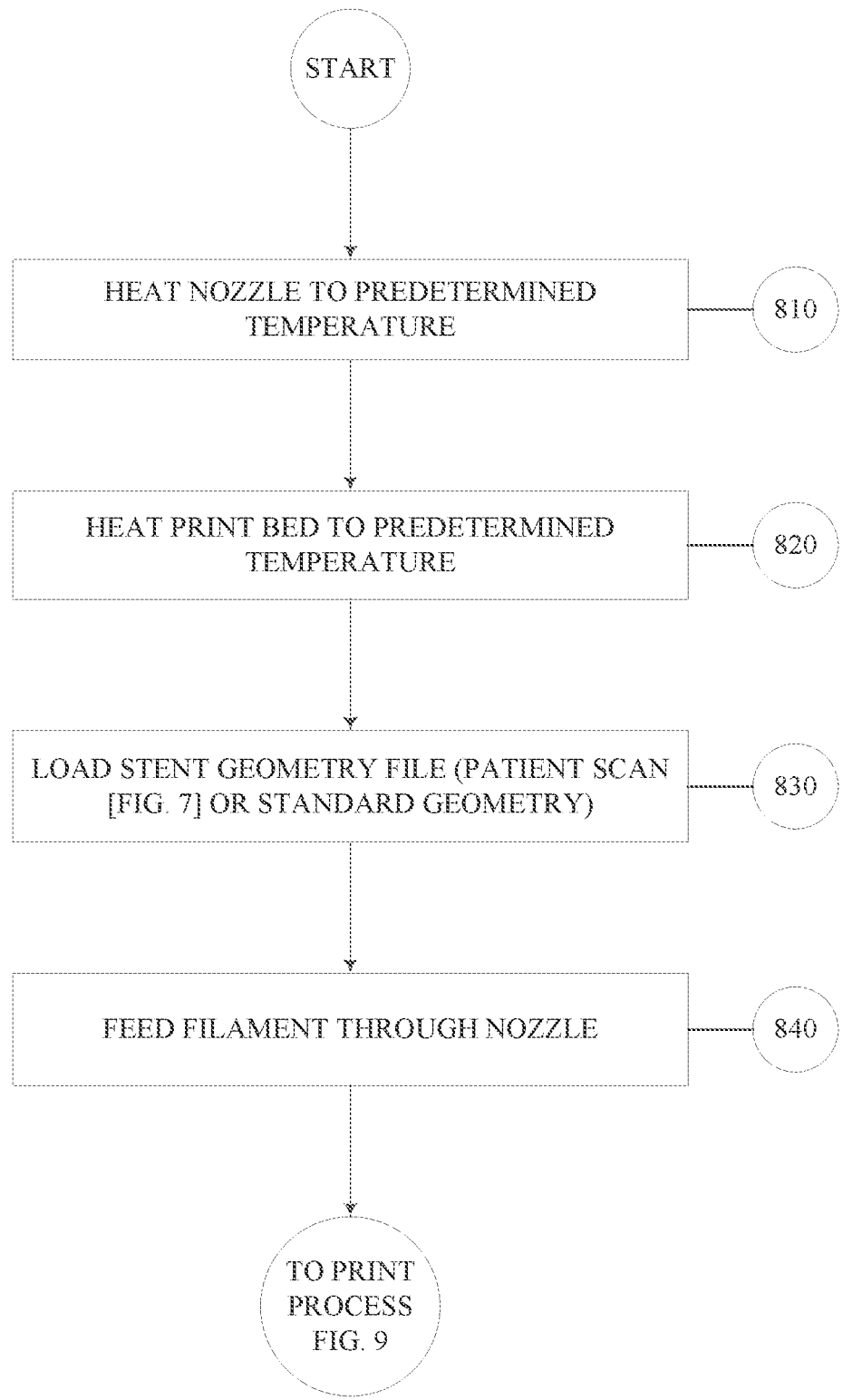
FIG. 8 is a flowchart of an exemplary medical device 3D-printing process according to one embodiment of the present disclosure.

Turning now to FIG. 8, an exemplary 3D-printing set-up process begins at step 810. At step 810, the system is configured to heat the nozzle to a predetermined temperature. The system may be configured to heat the nozzle in any suitable way, including, but not limited to, via resistance heating.

As discussed herein, the predetermined temperature may be any suitable temperature to change a printing material from a solid to a state (e.g., melted, partially melted, glass transition temperature, etc.) such that it can be passed through the nozzle (e.g., extruded). In some embodiments, the predetermined temperature is approximately a melt-point of the printing material. In at least one embodiment, the predetermined temperature is approximately 225 degrees Celsius. In other embodiments, the predetermined temperature of the nozzle is between about 220 degrees and 230 degrees Celsius. In particular embodiments, the predetermined temperature is within (e.g., higher or lower) approximately three degrees of the melt point of the printing material (e.g., filament).

A step 820, the system is configured to heat the print bed to a predetermined temperature. In various embodiments, the system is configured to heat the print bed to the predetermined temperature by any suitable mechanism, including, but not limited to, resistance heating.

In particular embodiments, the predetermined temperature is any suitable temperature that helps prevent the printing material (e.g., filament) stick or adhere to the print surface. In various embodiments, the predetermined temperature is at least partially dependent upon the material used for printing (e.g., the predetermined temperature is a suitable temperature for preventing the specific printing material from adhering to the print bed). In further embodiments, the system may be configured to vary the predetermined temperature on a layer-by-layer basis (e.g., the system may be configured to change the predetermined temperature during the stent/part/device creation/printing process). In some embodiments, the predetermined temperature is about 65 degrees Celsius. According to at least one embodiment, the predetermined temperature is any suitable temperature between about 35 degrees Celsius to about 95 degrees Celsius.

At step 830, the system is configured to load a geometry file (e.g., .STL file) for printing. As discussed above, the system may receive the geometry (also called stent model) file by any suitable mechanism and may access the information therein for creating the associated stent/part/device. As also discussed above, the geometry file may be a standard geometry file (e.g., a predetermined geometry that is not based on a specific patient) or the geometry file may be fully or at least partially customized based on a particular patient.

At step 840, the system is configured to begin feeding printing material (e.g., filament) through the (heated) nozzle. In various embodiments, the system is configured to feed the printing material through the nozzle automatically (e.g., substantially automatically) via a tubing and filament dry box (as discussed above in relation to FIG. 6). In some embodiments, a user may begin feeding the printing material through the nozzle by hand (then the system is configured to continue feeding the printing material through the nozzle substantially automatically).

Figure 9:
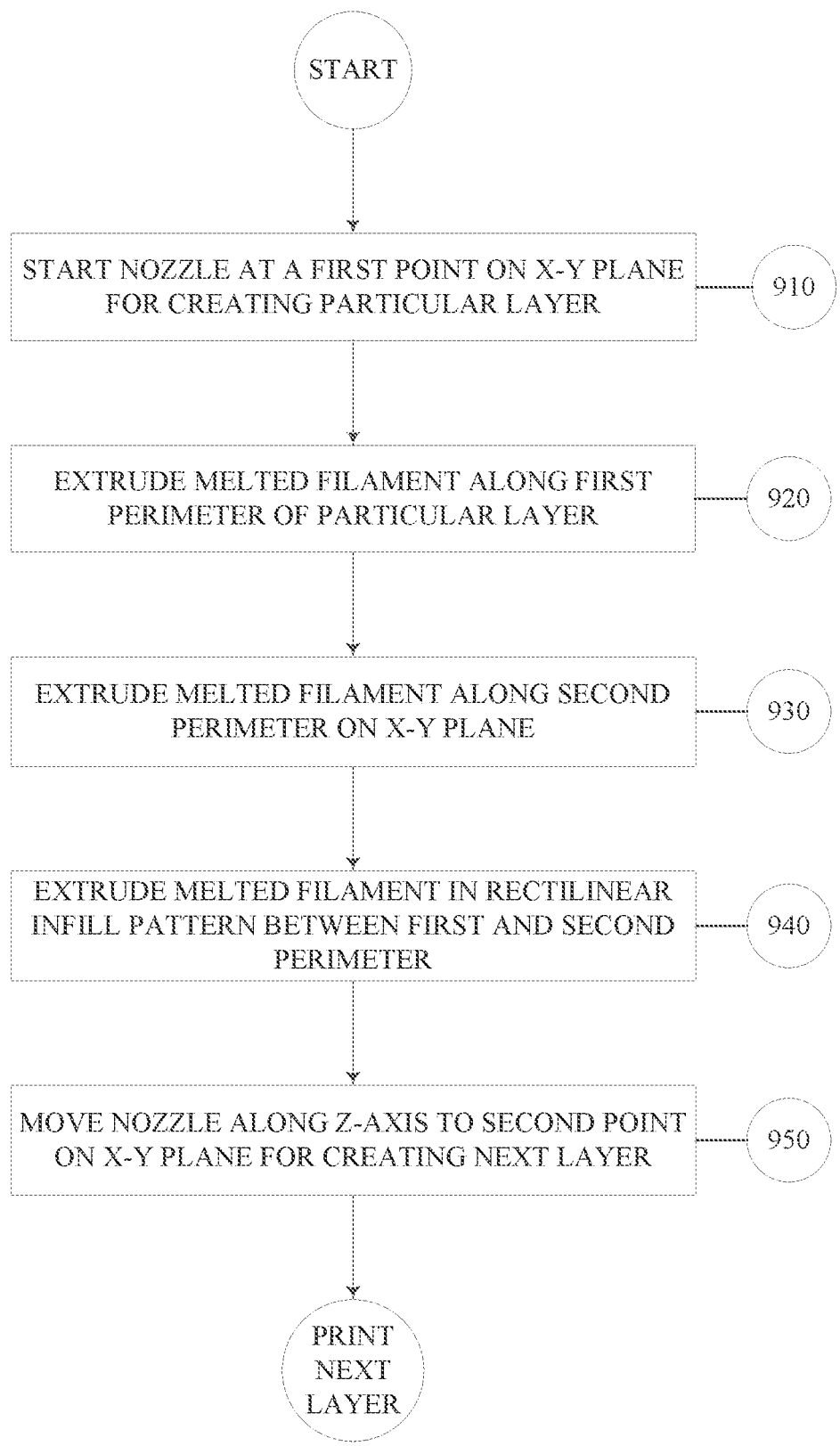
FIG. 9 is a flowchart of an exemplary medical device 3D-printing process according to one embodiment of the present disclosure.

As discussed herein, the system may be configured to print devices/parts/stents according to various techniques, each of which may affect device quality and may be advantageous for use in printing/creating various shapes of parts. As shown in FIGS. 9-11, the system may use a particular pattern of printing, but other methods may be used, including a "vase" method, which is also discussed herein.

Turning now to FIG. 9, an exemplary 3D-printing process is shown. The steps of this process are further depicted in FIGS. 10A-11, which are discussed below. Beginning at step 910, the system is configured to start a nozzle at a first point on an x-y plane for creating a particular layer. In various embodiments, the system begins extruding printing material (e.g., filament; PCU) through the heated nozzle at a particular point on the (heated) print bed.

The first point on the x-y plane (e.g., on the surface of the print bed) may be any suitable point. In various embodiments, the first point on the x-y plane is chosen by the system at random. In particular embodiments, the first point on the x-y plane is chosen by a user. In further embodiments, the first point on the x-y plane corresponds to a particular feature of a part/device to be printed/created (e.g., a portion of the part/device that is a solid wall and not a cut-out, stud, or the like). As further discussed below, the system may be configured to start the nozzle at a second point on the x-y plane (and a new location on the z (vertical) plane) such that the second point is not located directly above the first point for creating a seamless part.

At step 920, the system is configured to extrude melted printing material (e.g., filament) along a first perimeter of the particular layer. In various embodiments, the first perimeter is an outer perimeter of a stent or medical device (or other part), such as for example, if the stent/device/part is being printed from the outside-in. In some embodiments, the first perimeter is an inner perimeter of a stent or medical device (or other part), such as for example, if the stent/device/part is being printed from the inside-out.

At step 930, the system is configured to extrude melted printing material (e.g., filament) along a second perimeter of the particular layer. In various embodiments, the second perimeter is an opposite perimeter as the perimeter printed at step 920 (e.g., if the outer perimeter is printed at step 920, then the system, in various embodiments, is configured to print the inner perimeter at step 930). In some embodiments, the second perimeter of the particular layer may be offset from the first perimeter by a particular distance (e.g., the thickness of a wall of the device/part/stent). In further embodiments, the second perimeter may be directly next to and at least partially contacting the first perimeter printed at step 920.

In various embodiments, as discussed above, the system is configured to print a first perimeter and a second perimeter that form the inner and outer walls of a particular device/part/stent. In these embodiments (and others), there is a predetermined distance between the first and second perimeters. At step 940, the system is configured to extrude melted printing material (e.g., filament) in a rectilinear infill pattern between the first and second perimeters of the particular layer. In particular embodiments, the system is configured to "fill in" the area between the first and second perimeters by moving the nozzle (while extruding material) in a rectilinear pattern (e.g., from an edge of one perimeter to an edge of the other perimeter and back, as shown in exemplary FIG. 10).

In some embodiments, the system is configured to extrude melted printing material in an infill pattern other than rectilinear. For example, in one embodiment, the system is configured to extrude melted printing material in a pattern that is similar to the shape of the first or second perimeter (e.g., the system creates additional perimeter-shaped lines of material moving from one perimeter to another until the layer is completed).

Once the layer is completed (e.g., the perimeters are created and the layer is filled-in), at step 950, the system moves the nozzle along a z-axis, vertically, (and along the x-y axis) to a second point on a x-y plane for creating a next layer. As will be understood from discussions herein, seams in devices can affect quality of the device. As such, beginning a second layer at a new/second point may prevent seams from being formed on an inner and/or outer perimeter of the part/device/stent.

The system then continues the process by printing the next layer and repeating the process discussed about at steps 910-950.

As discussed above, FIGS. 10-11 depict 3D-printing process steps 910-950 shown in FIG. 9, according to one embodiment of the present disclosure. Generally, FIGS. 10A-10L show an exemplary 3D-printer, which may, in at least one embodiment, be located within a laminar flow cabinet. FIGS. 10A-10L show different steps of printing a substantially circular implantable airway stent (or other device or part), according to one embodiment of the present disclosure. For example, the printing process shown in FIGS. 10-11 may be suitable for printing a studded airway stent, such as the exemplary airway stent shown in FIG. 4.

In various embodiments, the exemplary 3D printer shown in FIGS. 10-11 includes a print bed 1000, which may be any suitable, substantially flat surface that can serve as a base for the 3D-printed implantable stent. In at least one environment, the print bed 1000 is heated to a temperature of about 65 degree Celsius or other suitable temperature prior to the system beginning to print the implantable stent.

In various embodiments, the 3D printer includes a 3D-printer with a Micro Swiss plated extruder (nozzle) 1010, or other suitable nozzle for 3D-printing PCU (e.g., Lubrizol® Carbothane™ AC-4095A; an exemplary "printing material"). In particular embodiments, an extruder, or nozzle, ejects material in liquid or semi-liquid form in order to deposit it in successive layers within the 3D printing process.

In at least one embodiment, the nozzle 1010 has a diameter, or opening in the nozzle, of about 0.5 mm, which, in some embodiments, results in a width of an extruded line of about 0.5 mm. In one embodiment, the system may be configured to apply an extrusion multiplier, which changes the volumetric rate of material extrusion by a percentage. In these embodiments (and others), the system may be configured to add an extrusion multiplier of about 1.05 (e.g., an increase in the material extrusion rate of 5%) to the amount of material to be extruded to account for variances in the actual amount of material extruded, that may be caused by a variety of factors (e.g., material buildup inside the nozzle, fluctuations in temperature, etc.). In particular embodiments, the system may be configured to apply an extrusion multiplier in excess of 1.05 (e.g., 1.06, 1.10, etc.). In further embodiments, the system may be configured to apply an extrusion multiplier less than 1.05 (e.g., 0.95, 0.97, 0.99, 1.03, etc.).

In particular embodiments, the diameter, the width, and the extrusion multiplier of the nozzle may be adjusted based on a variety of factors (e.g., material, temperature settings, type of stent, etc.). In various embodiments, the nozzle 1010 is heated to a temperature of about 225 degrees Celsius, or any other suitable temperature.

Figure 10A:
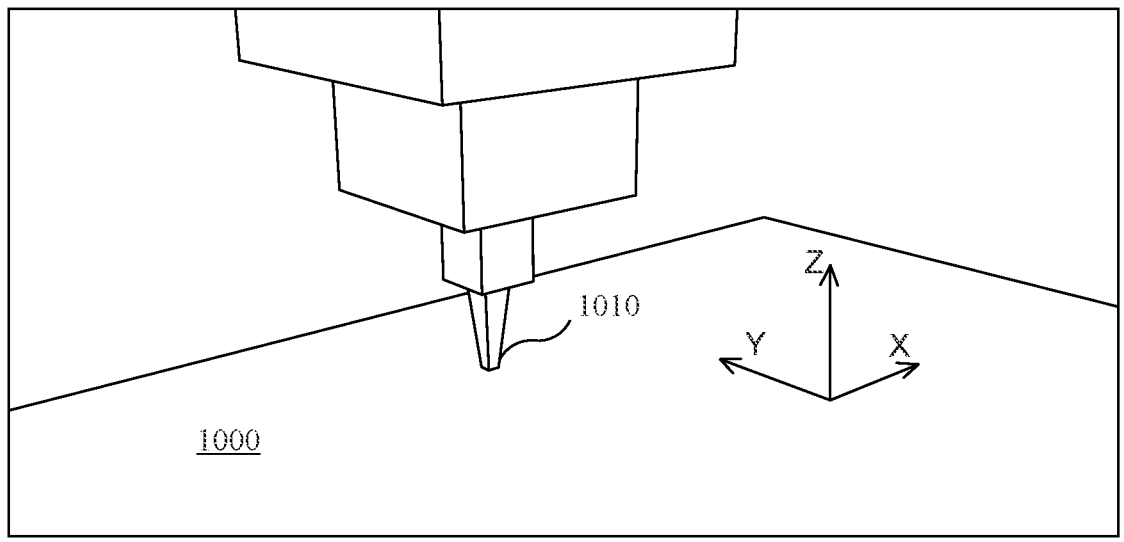
FIG. 10 (including FIGS. 10A-10L) shows steps of an exemplary 3D-printing process for printing a single layer of a medical device according to one embodiment of the present disclosure.
Figure 11:
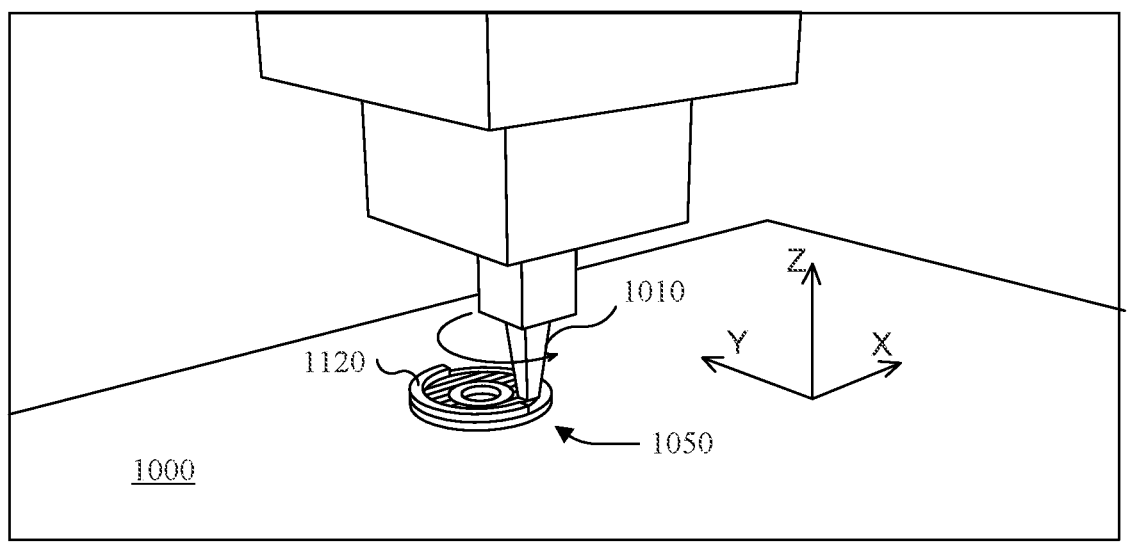
FIG. 11 shows a portion of an exemplary 3D-printing process for printing a medical device according to one embodiment of the present disclosure.

Beginning with FIG. 10A, the system is configured to start the nozzle at a first point on the x-y plane (e.g., on the print bed 1000, which may be heated to a predetermined temperature). As discussed herein, the first point on the x-y plane may be a random point.

Figure 10B:
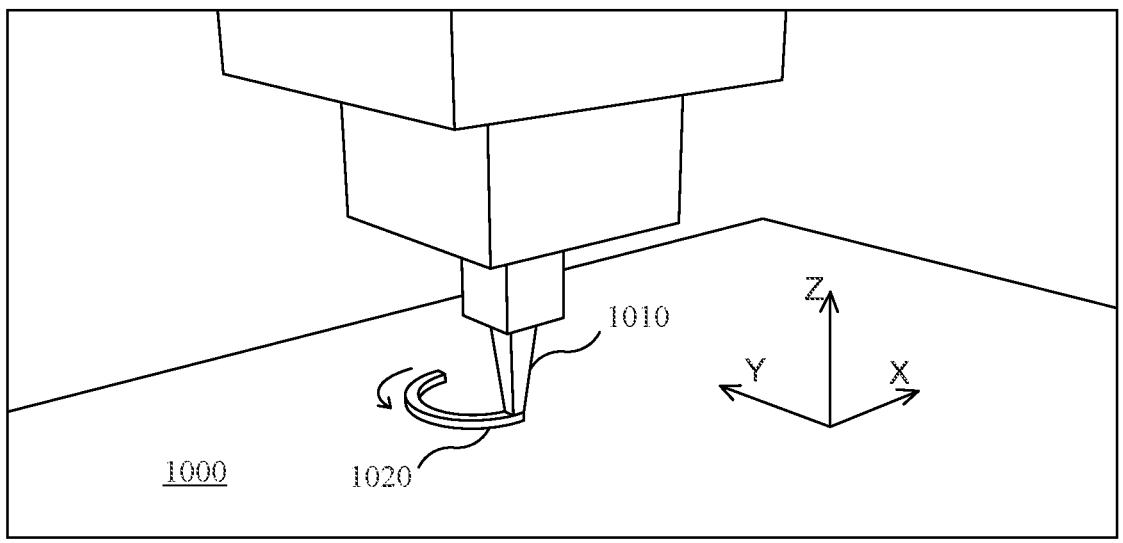

As shown in FIG. 10B, according to one embodiment of the present disclosure, the 3D-printing process continues with the nozzle 1010 depositing the printing material in a counterclockwise direction at a speed of about 3.0 mm/s to begin forming an outer perimeter 1020 of a first layer of an outer surface of an exemplary implantable airway stent. In at least one embodiment, the system deposits material in the first layer at a substantially low speed (e.g., approximately 3.0 mm/s) to facilitate adhesion to the print bed 1000 (as will be understood, sometimes the first layer does not adhere to the print bed quickly and a lower speed helps facilitate adhesion).

In some embodiments, the system is configured to deposit printing material at a height of about 0.1500 mm and a width of about 0.45 mm (90% of the extrusion width) to obtain stability of the implantable airway stent. In at least one embodiment, the extrusion width is lower for a first layer to account for possible flaring at the bottom of the implantable stent wall due to increased proximity between the nozzle 1010 and the print bed 1000. In particular embodiments, the system is configured to deposit material in any other suitable width between approximately 75% and 200% of the nozzle diameter, and any other suitable height between approximately 0.1 mm and 0.6 mm (e.g., 0.15 mm, 0.2 mm, 0.15-0.5 mm, etc.). In particular embodiments, the system is configured to deposit material at a width generally at least as wide as the height (e.g., if the height is 0.2 mm, the width, in some embodiments, is at least 0.2 mm).

In at least one embodiment, the 3D-printing process continues with the nozzle moving in a clockwise direction to create an outer perimeter of the implantable airway stent. In some embodiments, the nozzle may move at a speed of approximately 3.0 mm/s while extruding material at a width of about 0.45 mm and a height of about 0.1500 mm, but may move at other suitable speeds, up to and including 15 mm/s (e.g., 6.0 mm/s, 5.5 mm/s, 10.0 mm/s, etc.), depending on a variety of factors (e.g., material, temperature settings, type of stent, etc.). In various embodiments, as discussed herein, the 3D printer creates an outer perimeter 1020 of the implantable airway stent, which corresponds to the diameter of the outer surface of the implantable airway stent, which may be determined by the selection of critical points based on a CT scan of the patient requiring the implantable stent (as discussed above).

Figure 10C:
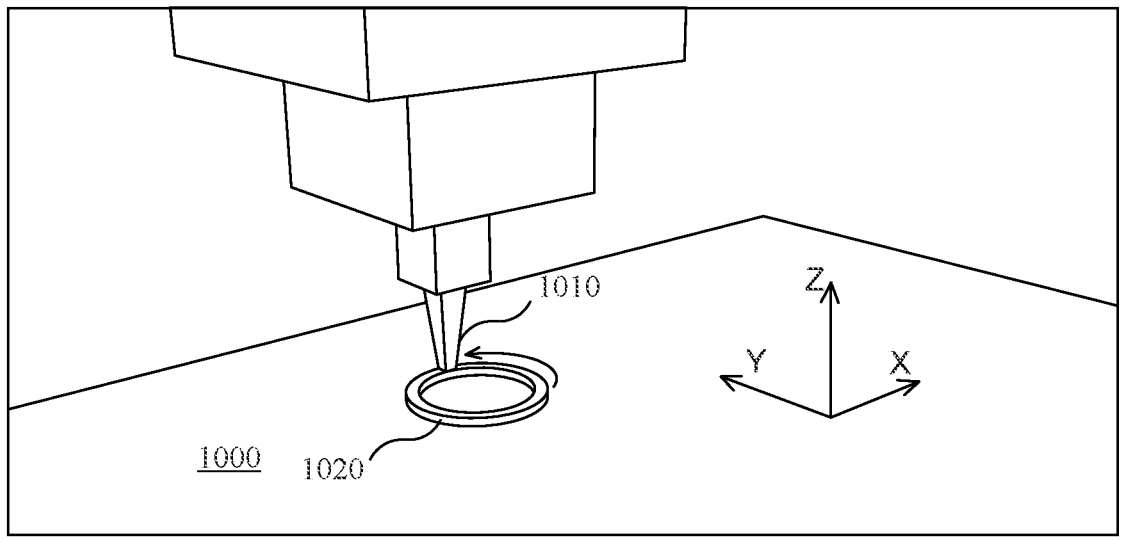

FIG. 10C shows the completion of the outer perimeter 1020, according to one embodiment of the present disclosure. In various embodiments, once the system completes creation of the outer perimeter 1020, the system begins creation of the inner perimeter 1030 of the stent, which may be a set distance equal to the desired wall thickness of the stent. In at least one embodiment, the desired wall thickness is between about 0.5 mm and about 1.0 mm.

Figure 10D:
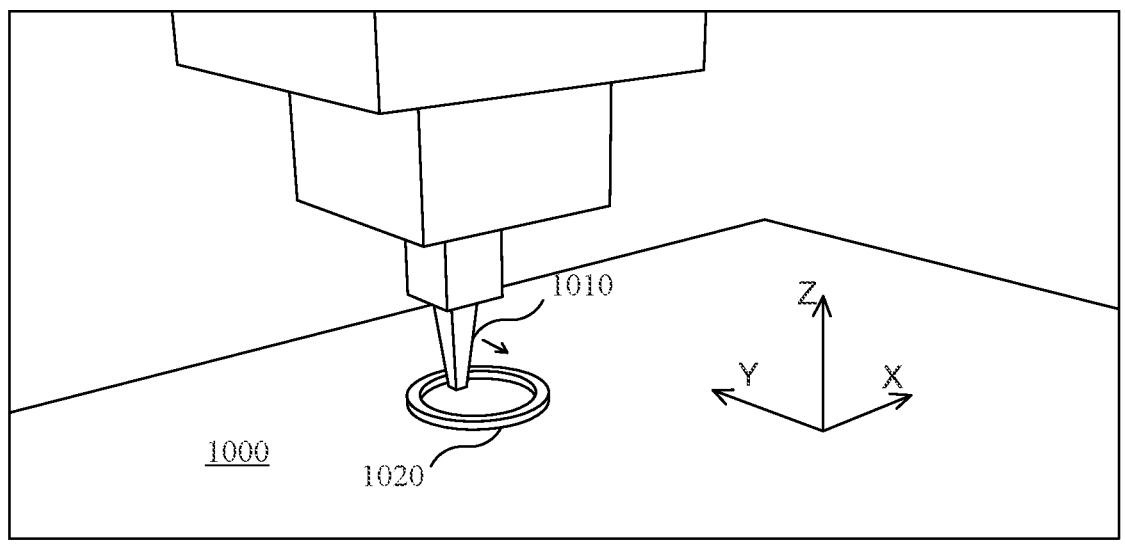

As shown in FIG. 10D, and according to one embodiment, the system is configured to move the nozzle 1010 to a first point to begin creation of the inner perimeter 1030 of the implantable airway stent. In various embodiments, a random start point is generated for the creation of the inner perimeter 1030 in order to eliminate the possibility of generating a seam running vertically along an inner surface of the implantable airway stent. In at least one embodiment, the start point for the creation of the inner perimeter is manually preselected.

Figure 10E:
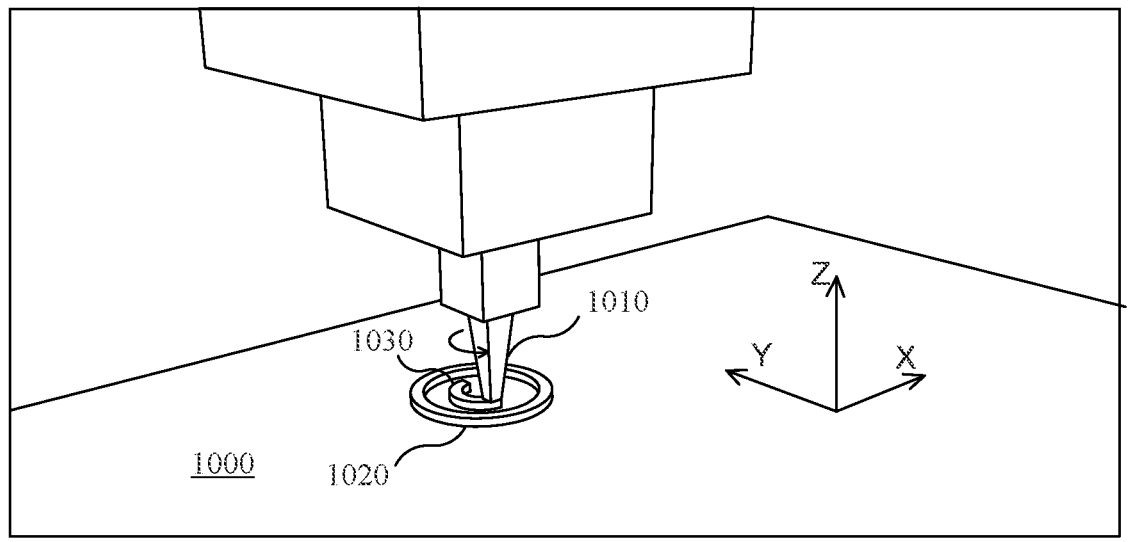

As shown in FIG. 10E, the system is configured to move the nozzle 1010 in a counterclockwise direction to create the inner perimeter 1030. As will be understood, in at least one embodiment, the system may be configured to use substantially similar settings (e.g., speed and height settings) for creating the inner perimeter 1030 as the system used for creation of the outer perimeter 1020. In further embodiments, the system may use different speed, height, and width settings for creation of the inner perimeter 1030 than the system used for the creation of the outer perimeter 1020.

Figure 10F:
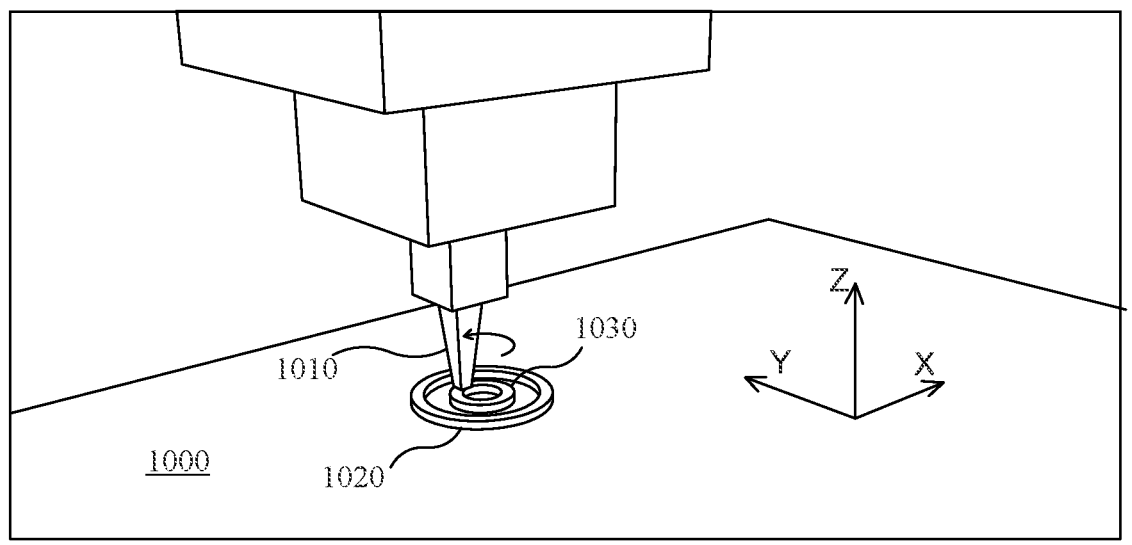
Figure 10G:
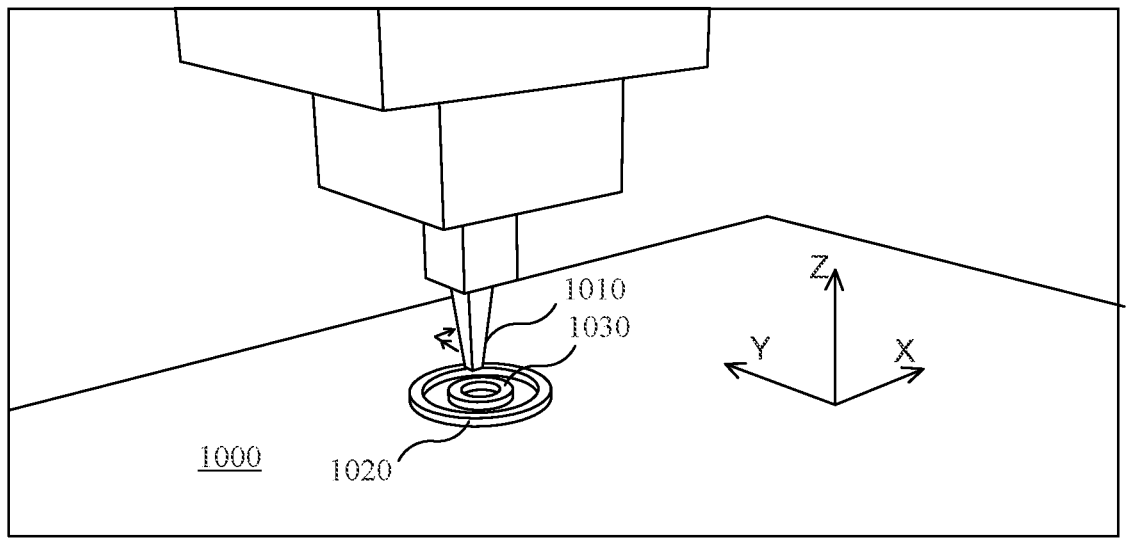
Figure 10H:
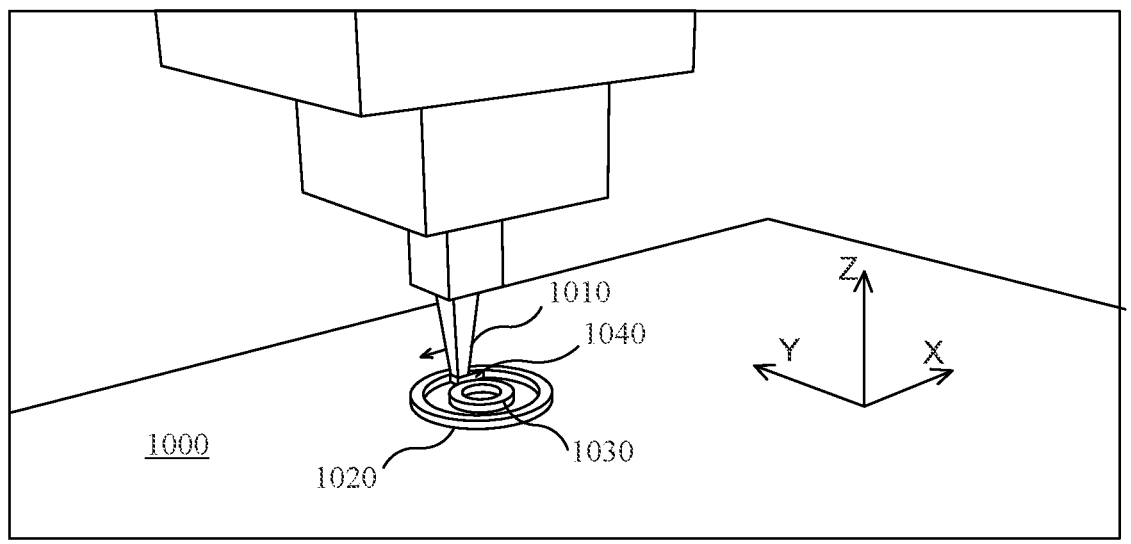
Figure 10I:
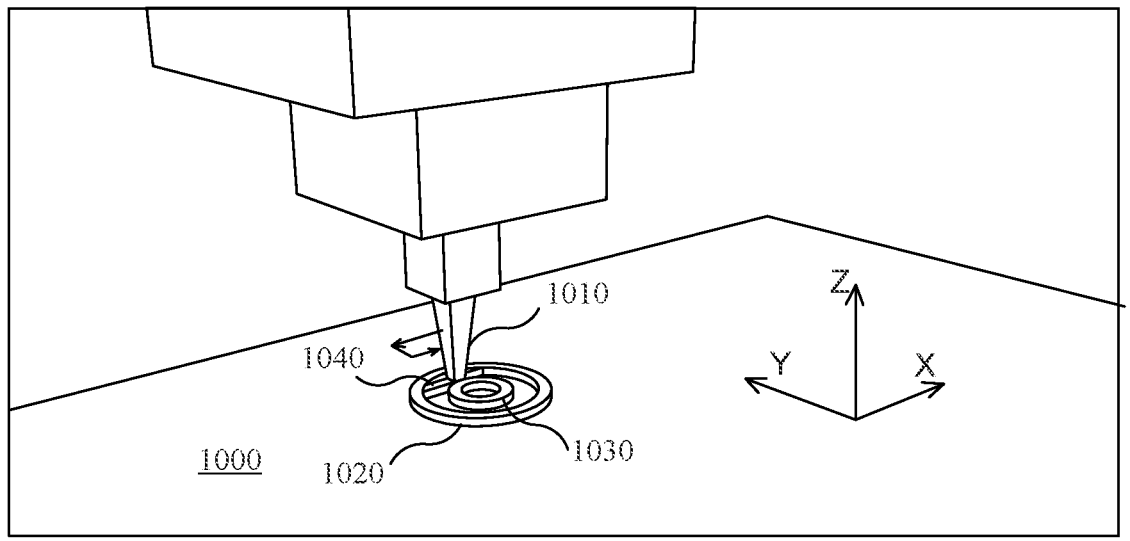
Figure 10J:
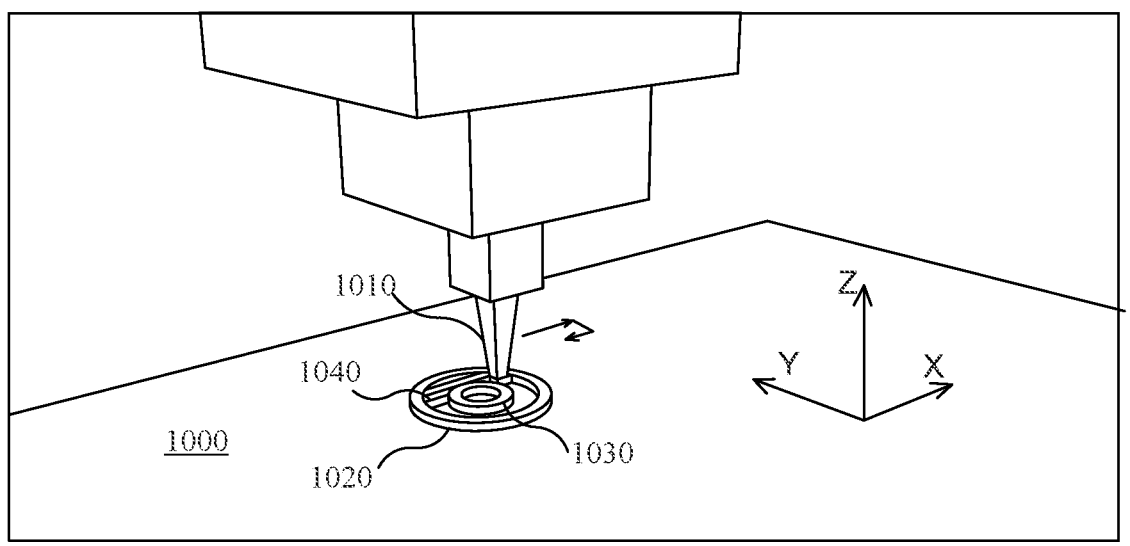
Figure 10K:
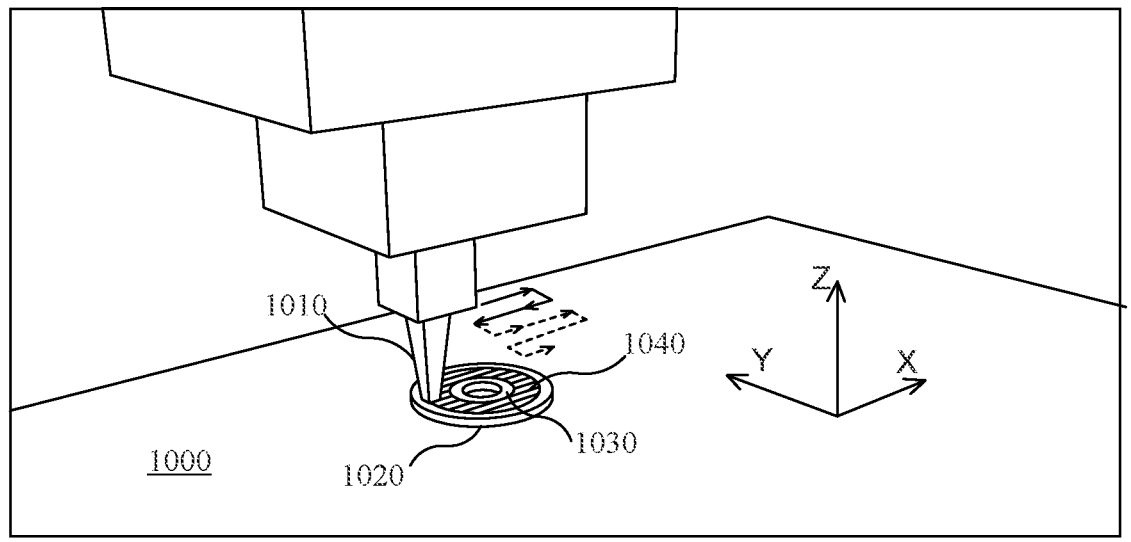

FIG. 10F shows the completion of the inner perimeter 1030, according to one embodiment of the present disclosure. In various embodiments, upon completion of the outer perimeter 1020 and the inner perimeter 1030, the layer is completed by filling in the space between the outer perimeter 1020 and the inner perimeter 1030. In at least one embodiment, the nozzle creates the infill 1040 by moving back and forth in a rectilinear pattern along the x-axis (and y-axis) between the outer perimeter 1020 and the inner perimeter 1030 as shown in FIGS. 10G and 10I. In some embodiments, the nozzle creates the infill by moving in a diagonal pattern between the outer surface and the inner perimeter. In particular embodiments, the nozzle creates the infill by moving in a pattern along the y-axis (and x-axis, in some embodiments) between the outer perimeter 1020 and the inner perimeter 1030. In at least one embodiment, about 100% of the space between the outer perimeter 1020 and the inner perimeter 1030 is filled in. In some embodiments, less than 100% of the space between the outer perimeter 1020 and the inner perimeter 1030 is filled in. In particular embodiments, the infill 1040 overlaps the outer perimeter 1020 and/or the inner perimeter 1030. In at least one embodiment, the infill overlaps about 15% of the outer surface and the inner perimeter.

Figure 10L:
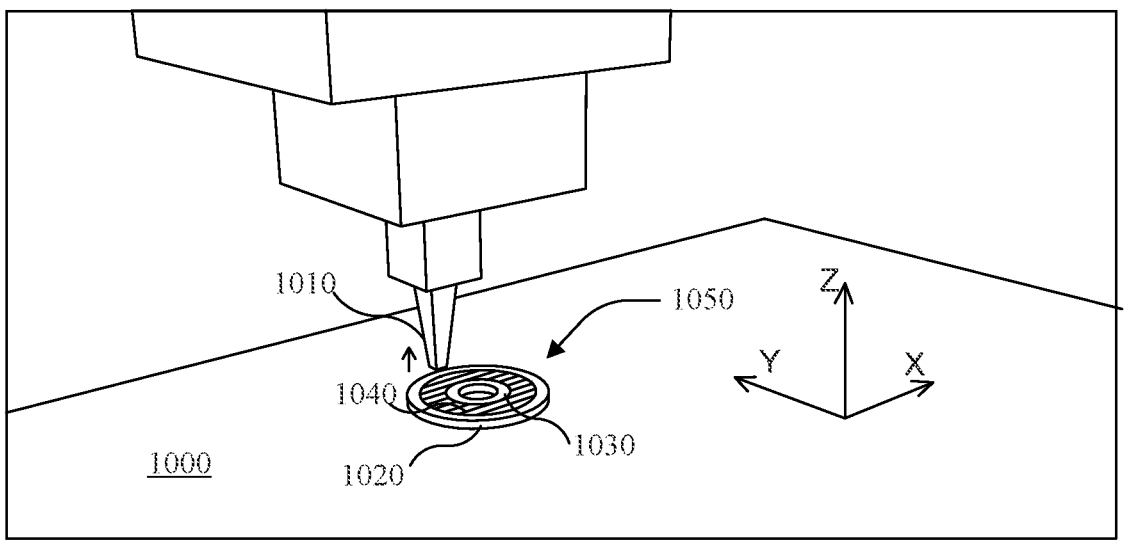

FIG. 10L shows a completed first layer 1050 (e.g., a first layer of a wall of an exemplary implantable airway stent), according to one embodiment of the present disclosure. In the embodiment shown in FIG. 10L, the system is configured to move the nozzle 1010 to a second point in a x-y plane to begin printing the second layer of the exemplary implantable airway stent, where the second point is a different point than the first point (e.g., where the system begin printing the first layer), such that a seamless implantable airway stent is created.

Referring now to FIG. 11, which illustrates the beginning of the 3D-printing process for printing a second layer of the implantable airway stent, according to one embodiment of the present disclosure. In various embodiments, the nozzle 1010 deposits a second layer 1120 of the printing material directly on top, and in line with, the outer perimeter 1020 of the first layer 1050 in a counterclockwise direction. In at least one embodiment, the nozzle deposits the second layer in a clockwise direction. As will be understood from discussions herein, in at least one embodiment, the system then prints the remainder of the exemplary implantable airway stent layer-by-layer essentially repeating the steps described above.

Sensors/Computing System

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can include various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions include, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the embodiments of the claimed systems may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed system are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically includes one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the system is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems will be readily discernible from the description herein, by those of ordinary skill in the art. Many embodiments and adaptations of the disclosure and claimed systems other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Alternate Embodiments

Alternative embodiments of the system may include features that are, in some respects, similar to the various components described above. Selected distinguishing features of these alternative embodiments are discussed below.

Vase Method

In various embodiments, the spiral vase method begins with the nozzle depositing material in a counterclockwise (or clockwise) direction at a set height (and width) to create the first layer of the perimeter. In some embodiments, the height is determined by the device/part requirements. Continuing with this embodiment (and in other embodiments), once the perimeter is completed, the nozzle continues moving around in the same direction while slowly and continually incrementing its position along the z-axis, such that subsequent layers of the perimeter are printed. In this embodiment, the stent, or other printed part/device, is printed as a long spiral, without any discrete layers other than the first layer. The nozzle, in this embodiment, is continuously printing while in motion, which may reduce the possibility of imperfections in the completed part/device.

As will be understood from discussions herein, the nozzle does not make any non-printing movements using the vase method of printing, and, in some embodiments, a part is printed in one unbroken spiral shaped line, which may produce a very "clean" part. As will further be understood, any time a nozzle makes non-printing movements, or sharp directional changes, there is a chance an imperfection like a void may be included in a part.

The vase printing method may work well for stents (or other parts) with uniform wall thickness throughout (the width of the single line is set to the wall thickness), so stents like the accordion, threaded stent, tapered stent, etc. But for the studded stents, for example, the studs essentially create non-uniform wall thickness due to their height, and printing a studded stent using the vase method may result in the studs being hollow (not infilled), which may cause quality issues.

Additional Medical Devices

This disclosure is not limited to implantable airway stents. Several other applications of the systems and methods described herein have been contemplated, including, but not limited to: prosthetics (e.g., rib prosthetic, leg prosthetic, arm prosthetic, etc.); bearing surfaces for joint reconstruction implants (e.g., radial head replacement); craniomaxillofacial reconstruction plates; cardiovascular, biliary, esophageal, urinary, prostatic, duodenal, colonic, and pancreatic stents; custom catheters; and/or deformable material in a spinal disc replacement device, such as a Freedom® lumbar disc or other like devices.

Additional Scanning Technologies

In addition to a CT scan as described above, this disclosure contemplates several means of obtaining the dimensional requirements of the device/part to be printed, including, but not limited to: positron emission tomography (PET) scans, PET/CT scans, X-rays, handheld 3D medical scanners, ultrasounds, dual-energy X-ray absorptiometry (DXA) scans, magnetic resonance imaging (MM), near-infrared spectroscopy (NIR), functional near-infrared spectroscopy (FNIR), magnetic particle imaging (MPI), photoacoustic imaging, elastography, tactile imaging, and the like.

Additional Materials

This disclosure is not limited to the use of PCU for printing implantable airway stents and other devices/parts. The systems and methods described herein have contemplated the use of several other materials, including, but not limited to: polyether-ether-ketone (PEEK), polyether urethane, polyether urethane and silicone hybrids, polyisobutylene-based thermoplastic elastomers, and other thermoplastics, and other like materials.

Combination of Stent Designs

Multiple implantable airway stent designs may be printed apart from those described above, particularly where the stent designs described above may be used in combination with each other. For example, in various alternate embodiments, the notches 204 of the cutout stent 200 may be applied to the accordion stent 100, the spiral stent 300, the studded stent 400, or the tapered stent 500. In some embodiments, the studs 402 of the studded stent 400 may be applied to the accordion stent, the spiral stent, or the tapered stent. In particular embodiments, the increasing or decreasing feature of the length of the tapered stent 500, may be applied to the accordion stent 100, the cutout stent 200, the spiral stent 300, or the studded stent 400. Furthermore, in at least one embodiment, the protrusions of the spiral stent 300 may be applied to the accordion stent 100.

In further embodiments, stents that include multiple sections and/or branches may include portions that are printed as different designs. For example, a particular substantially y-shaped (or v-shaped, or other suitably shaped) stent includes a first branch that includes studs and a second branch that is tapered. As another example, a second particular stent includes a first branch that includes an accordion design and a second portion that includes a spiral stent design.

Printing Multiple Materials

In addition to printing a device/part using one material, such as PCU as described above, this disclosure also contemplates the use of multiple materials. In one embodiment, the system may be configured to print different grades of PCU (e.g., different grades of PCU may be fed through the print head (in a single print nozzle or multiple print nozzles)) such that one area of the resulting stent (or other suitable part) may be very stiff and other areas may be less stiff, based on the grade of PCU.

In various embodiments, water soluble materials (e.g., polyvinyl alcohol, "PVA") may be used in conjunction with PCU, or other material, such that supports and other removable parts can be printed in PVA and then dissolved away in water, leaving behind the PCU (or other material) component. In some embodiments, material for printing a separate device/part may be used in conjunction with PCU, such that the separate device/part and the implantable stent can be combined in a single printing (via a single print nozzle, multiple print heads, multiple print nozzles, and/or multiple print heads).

In at least one embodiment, the systems and methods herein may relate to printing parts/medical devices that include both PEEK and PCU, which may be printed through a single nozzle or multiple nozzles.

This disclosure contemplates multiple purpose devices (e.g., implantable stents with built in electronic circuitry for real-time monitoring; implantable stents with time-released medicinal compartments, etc.).

CONCLUSION

The foregoing description of the exemplary embodiments has been presented only for the purposes of illustration and description and is not intended to be exhaustive or to limit the systems to the precise forms disclosed. Many modifications and variations are possible in light of the above teaching.

The embodiments were chosen and described in order to explain the principles of the systems and their practical application so as to enable others skilled in the art to utilize the systems and various embodiments and with various modifications as are suited to the particular use contemplated. Alternative embodiments will become apparent to those skilled in the art to which the present systems pertain without departing from their spirit and scope.

What is claimed is:

1. A method for producing a seamless polycarbonate urethane airway stent comprising the steps of:
   substantially drying polycarbonate urethane (PCU) filament;
   feeding the substantially dry PCU filament through a nozzle, wherein the nozzle melts the substantially dry PCU filament;

creating a first layer of the seamless polycarbonate urethane airway stent by:
  starting the nozzle at a first point on a first x-y plane and extruding melted PCU filament along a first path at a first speed, creating an outer perimeter of the first layer;
  extruding melted PCU filament along a second path, creating an inner perimeter of the first layer; and
  extruding melted PCU in a first infill pattern along the first x-y plane between the inner and outer perimeters of the first layer, wherein the distance between an exterior of the outer perimeter and an interior of the inner perimeter is about 0.5 mm to 1.0 mm;
moving the nozzle along a z-axis; and
creating a second layer of the seamless polycarbonate urethane airway stent by:
  starting the nozzle at a second point on a second x-y plane and extruding melted PCU filament along a third path at a second speed approximately double the first speed, creating an outer perimeter of the second layer;
  extruding melted PCU filament along a fourth path creating an inner perimeter of the second layer; and
  extruding melted PCU in a second infill pattern along the second x-y plane between the inner and outer perimeters of the second layer, wherein the first point and the second point are different points, thereby creating the seamless polycarbonate urethane airway stent, wherein the seamless polycarbonate urethane airway stent comprises a hollow interior.

2. The method of claim 1, wherein the distance between the exterior of the outer perimeter and the interior of the inner perimeter is about 0.75 mm to 0.85 mm.

3. The method of claim 1, wherein the method further comprises the step of creating at least one layer prior to creating the first layer.

4. The method of claim 1, wherein the first speed is approximately 3.0 mm per second.

5. The method of claim 1, wherein the nozzle is configured to print along the perimeter of the hollow interior.

6. The method of claim 1, wherein the nozzle does not cross the hollow interior of the seamless polycarbonate urethane airway stent while printing.

7. The method of claim 1, wherein the method further comprises storing the PCU filament in a dry box.

8. The method of claim 1, wherein the seamless polycarbonate urethane airway stent comprises one or more studs.

9. The method of claim 1, wherein the seamless polycarbonate urethane airway stent comprises a plurality of frustum-shaped protrusions that comprise a sloping surface that extends away from an exterior surface of the seamless polycarbonate urethane airway stent at an acute angle and a flat, circular surface substantially parallel to the exterior surface, wherein the sloping surface extends between the exterior surface and the flat, circular surface.

10. The method of claim 1, wherein the seamless polycarbonate urethane airway stent comprises a radial stiffness of between 8 to 20 N/mm tested at about 37 degrees Celsius, the exterior surface shaped to fit compatibly against the interior surface of an airway.

11. A method for producing a polycarbonate urethane stent comprising the steps of:
  substantially drying polycarbonate urethane filament;
  heating a print bed to approximately 65 degrees Celsius;
  feeding the substantially dry PCU filament through a nozzle, wherein the nozzle melts the substantially dry PCU filament; and
  extruding melted PCU filament in discrete vertical layers, wherein each discrete vertical layer is created by: a) extruding melted PCU filament along an outer perimeter of the medical device in an x-y plane, and b) extruding melted PCU in an infill pattern along the x-y plane to fill-in the discrete vertical layer of the polycarbonate urethane stent from the outer perimeter to an inner perimeter, thereby creating the polycarbonate urethane stent comprising a wall thickness of 0.5 mm to 1.0 mm with a radial stiffness of between 8 to 20 N/mm tested at about 37 degrees Celsius, wherein the polycarbonate urethane stent comprises a hollow interior.

12. The method of claim 11, wherein:
the x-y plane is a first x-y plane corresponding to a first point on a z-axis; and
the method further comprises:
  creating a first discrete vertical layer by: a) extruding melted PCU filament along the outer perimeter of the medical device in the first x-y plane, and b) extruding melted PCU in a first infill pattern along the first x-y plane to fill-in the first discrete vertical layer of the polycarbonate urethane stent from the outer perimeter to the inner perimeter;
  moving the nozzle along the z-axis to a second x-y plane; and
  creating a second discrete vertical layer by: a) extruding melted PCU filament along the outer perimeter of the medical device in the second x-y plane, and b) extruding melted PCU in a second infill pattern along the second x-y plane to fill-in the second discrete vertical layer of the polycarbonate urethane stent from the outer perimeter to the inner perimeter.

13. The method of claim 12, wherein the first discrete vertical layer of the polycarbonate urethane stent is substantially tubular in shape with a first diameter.

14. The method of claim 13, wherein the second discrete vertical layer of the polycarbonate urethane stent comprises a second diameter.

15. The method of claim 14, wherein the second diameter is greater than the first diameter.

16. The method of claim 12, wherein a width of the first layer is about 10% less than a width of the second layer.

17. The method of claim 12, wherein the nozzle moves at a first speed when creating the first layer and a second speed when creating the second layer.

18. The method of claim 17, wherein the first speed is approximately 50% of the second speed.

19. The method of claim 12, wherein the method further comprises the step of creating at least one layer prior to creating the first layer.

20. The method of claim 11, wherein substantially drying the polycarbonate urethane comprises storing the PCU filament in a dry box.

21. The method of claim 11, wherein substantially drying the polycarbonate urethane comprises drying the PCU filament via a vacuum oven at a temperature of at least 99 degrees Celsius for a minimum of 30 minutes.

22. The method of claim 11, wherein the nozzle moves at approximately 6.0 millimeters per second.

23. The method of claim 11, wherein the nozzle is configured to print along the perimeter of the polycarbonate urethane stent.

24. The method of claim 11, wherein the nozzle is configured to not cross the hollow interior of the polycarbonate urethane stent.

25. The method of claim 11, wherein the nozzle begins at a different location on a x-axis or a y-axis for each discrete vertical layer, thereby creating a seamless polycarbonate urethane stent.

26. The method of claim 11, wherein the method further comprises the step of creating at least one layer that does not form part of the polycarbonate urethane stent.

27. The method of claim 11, wherein the polycarbonate urethane stent comprises one or more studs.

28. The method of claim 11, wherein the polycarbonate urethane stent comprises a plurality of frustum-shaped protrusions that comprise a sloping surface that extends away from an exterior surface of the polycarbonate urethane stent at an acute angle and a flat, circular surface substantially parallel to the exterior surface, wherein the sloping surface extends between the exterior surface and the flat, circular surface.

29. The method of claim 11, wherein the polycarbonate urethane stent comprises a smooth interior surface.

30. The method of claim 11, wherein the distance between an exterior of the outer perimeter and an interior of the inner perimeter is about 0.75 mm to 0.85 mm.

\* \* \* \* \*